US012569628B2

(12) United States Patent
Scholz et al.

(10) Patent No.: US 12,569,628 B2
(45) Date of Patent: Mar. 10, 2026

(54) DELIVERY OF MEDICINAL GAS IN A LIQUID MEDIUM

(71) Applicant: Third Pole, Inc., Waltham, MA (US)

(72) Inventors: Wolfgang Scholz, Beverly, MA (US); Gregory W. Hall, Belmont, MA (US); Jacob Naroian, Winchester, MA (US)

(73) Assignee: Third Pole, Inc., Waltham, MA (US)

( * ) Notice: Subject to any disclaimer, the term of this patent is extended or adjusted under 35 U.S.C. 154(b) by 0 days.

(21) Appl. No.: 18/301,118

(22) Filed: Apr. 14, 2023

(65) Prior Publication Data

US 2023/0330359 A1 Oct. 19, 2023

Related U.S. Application Data

(60) Provisional application No. 63/488,341, filed on Mar. 3, 2023, provisional application No. 63/375,446, filed
(Continued)

(51) Int. Cl.
*B01F 23/2373* (2022.01)
*A61M 3/00* (2006.01)
(Continued)

(52) U.S. Cl.
CPC .......... *A61M 13/003* (2013.01); *A61M 3/005* (2013.01); *A61M 11/00* (2013.01); *A61M 35/30* (2019.05); *B01F 23/237* (2022.01); *A61K 9/51* (2013.01); *A61M 2005/006* (2013.01); *A61M 2202/00* (2013.01); *A61M 2202/0007* (2013.01); *A61M 2202/0208* (2013.01);
(Continued)

(58) Field of Classification Search
CPC ........ B01F 25/50; B01F 25/53; B01F 23/231; B01F 23/2319; B01F 23/238; B01F 23/237; B01F 23/2373; B01F 23/2375; A61M 2202/0275; A61M 13/03; A61M 35/30
See application file for complete search history.

(56) References Cited

U.S. PATENT DOCUMENTS 709,867 A 9/1902 Bradley et al.
2,485,478 A 10/1949 Cotton
(Continued)

FOREIGN PATENT DOCUMENTS

CA 2413834 6/2004
CN 1099997 3/1995
(Continued)

OTHER PUBLICATIONS

Yasunari Maeda et al., Generation mechanism of micro-bubbles in a pressurized dissolution method, Available online Sep. 26, 2014, Experimental Thermal and Fluid Science, 60, 2015, pp. 201-207 (Year: 2015).*
(Continued)

*Primary Examiner* — Bhisma Mehta
*Assistant Examiner* — Anna E Goldberg-Richmeier
(74) *Attorney, Agent, or Firm* — Greenberg Traurig, LLP; David J. Dykeman; Jaime Burke

(57) ABSTRACT

Systems and methods for delivering a gas, such as nitric oxide, are provided. In some embodiments, systems and methods are provided for delivering a gas, such as nitric oxide, in the form of nanobubbles and/or a dissolved gas using a liquid medium.

21 Claims, 64 Drawing Sheets

Related U.S. Application Data on Sep. 13, 2022, provisional application No. 63/331,160, filed on Apr. 14, 2022.

(51) Int. Cl.

| | |
|---|---|
| *A61M 11/00* | (2006.01) |
| *A61M 13/00* | (2006.01) |
| *A61M 35/00* | (2006.01) |
| *B01F 23/237* | (2022.01) |
| *A61K 9/51* | (2006.01) |
| *A61M 5/00* | (2006.01) |

(52) U.S. Cl.
CPC .............. *A61M 2202/0216* (2013.01); *A61M 2202/0225* (2013.01); *A61M 2202/0233* (2013.01); *A61M 2202/0241* (2013.01); *A61M 2202/0266* (2013.01); *A61M 2202/0275* (2013.01); *A61M 2202/0283* (2013.01); *A61M 2202/0291* (2013.01); *A61M 2205/07* (2013.01); *A61M 2205/3606* (2013.01); *A61M 2206/20* (2013.01); *B01F 23/2373* (2022.01); *B01F 23/2376* (2022.01); *B01F 23/23765* (2022.01)

(56) References Cited

U.S. PATENT DOCUMENTS

| | | | |
|---|---|---|---|
| 2,485,481 A | 10/1949 | Cotton |
| 2,525,938 A | 10/1950 | Peck |
| 2,684,448 A | 7/1954 | Nilles |
| 3,047,370 A | 7/1962 | Aviges et al. |
| 3,225,309 A | 12/1965 | Phelps |
| 3,805,590 A | 4/1974 | Ringwall et al. |
| 4,287,040 A | 9/1981 | Alamaro |
| 4,500,563 A | 2/1985 | Ellenberger et al. |
| 4,505,795 A | 3/1985 | Alamaro |
| 4,680,694 A | 7/1987 | Huynh et al. |
| 4,695,358 A | 9/1987 | Mizuno et al. |
| 4,705,670 A | 11/1987 | O'Hare |
| 4,816,229 A | 3/1989 | JeRnsen et al. |
| 4,877,589 A | 10/1989 | Conrad |
| 5,285,372 A | 2/1994 | Huynh et al. |
| 5,378,436 A | 1/1995 | Endoh et al. |
| 5,396,882 A | 3/1995 | Zapol |
| 5,413,097 A | 5/1995 | Birenheide et al. |
| 5,471,977 A | 12/1995 | Olsson et al. |
| 5,485,827 A | 1/1996 | Zapol et al. |
| 5,531,218 A | 7/1996 | Krebs |
| 5,546,935 A | 8/1996 | Champeau |
| 5,558,083 A | 9/1996 | Bathe et al. |
| 5,573,733 A | 11/1996 | Salama |
| 5,674,381 A | 10/1997 | Dekker |
| 5,692,495 A | 12/1997 | Sheu |
| 5,732,693 A | 3/1998 | Bathe et al. |
| 5,749,937 A | 5/1998 | Detering et al. |
| 5,752,504 A | 5/1998 | Bathe |
| 5,827,420 A | 10/1998 | Shirazi et al. |
| 5,839,433 A | 11/1998 | Higenbottam |
| 5,845,633 A | 12/1998 | Psaros |
| 5,918,596 A | 7/1999 | Heinonen |
| 6,089,229 A | 7/2000 | Bathe et al. |
| 6,109,260 A | 8/2000 | Bathe |
| 6,125,846 A | 10/2000 | Bathe et al. |
| 6,164,276 A | 12/2000 | Bathe et al. |
| 6,186,140 B1 | 2/2001 | Hoague |
| 6,186,142 B1 | 2/2001 | Schmidt et al. |
| 6,197,091 B1 | 3/2001 | Ji et al. |
| 6,224,653 B1 | 5/2001 | Shvedchikov et al. |
| 6,250,302 B1 | 6/2001 | Rantala |
| 6,290,683 B1 | 9/2001 | Erez et al. |
| 6,296,827 B1 | 10/2001 | Castor et al. |
| 6,365,868 B1 | 4/2002 | Borowy et al. |
| 6,432,077 B1 | 8/2002 | Stenzler |
| 6,532,956 B2 | 3/2003 | Hill |
| 6,536,429 B1 | 3/2003 | Pavlov et al. |
| 6,581,599 B1 | 6/2003 | Stenzler |
| 6,612,306 B1 | 9/2003 | Mault |
| 6,668,828 B1 | 12/2003 | Figley et al. |
| 6,758,214 B2 | 7/2004 | Fine et al. |
| 6,920,876 B2 | 7/2005 | Miller et al. |
| 6,955,171 B1 | 10/2005 | Figley et al. |
| 6,955,790 B2 | 10/2005 | Castor et al. |
| 6,984,256 B2 | 1/2006 | Lamprecht et al. |
| 6,986,351 B2 | 1/2006 | Figley et al. |
| 7,025,869 B2 | 4/2006 | Fine et al. |
| 7,040,313 B2 | 5/2006 | Fine et al. |
| 7,122,018 B2 | 10/2006 | Stenzler et al. |
| 7,220,393 B2 | 5/2007 | Miller et al. |
| 7,255,105 B2 | 8/2007 | Figley et al. |
| 7,299,785 B1 | 11/2007 | Lee |
| 7,312,584 B2 | 12/2007 | Tamita et al. |
| 7,335,181 B2 | 2/2008 | Miller et al. |
| 7,485,324 B2 | 2/2009 | Miller et al. |
| 7,498,000 B2 | 3/2009 | Pekshev et al. |
| 7,516,742 B2 | 4/2009 | Stenzler et al. |
| 7,520,866 B2 | 4/2009 | Stenzler et al. |
| 7,523,752 B2 | 4/2009 | Montgomery et al. |
| 7,531,133 B2 | 5/2009 | Hole et al. |
| 7,560,076 B2 | 7/2009 | Rounbehler et al. |
| 7,589,473 B2 | 9/2009 | Suslov |
| 7,597,731 B2 | 10/2009 | Palmerton et al. |
| 7,618,594 B2 | 11/2009 | Rounbehler et al. |
| 7,744,812 B2 | 6/2010 | Witherspoon et al. |
| 7,861,516 B2 | 1/2011 | Allanson et al. |
| 7,861,717 B1 | 1/2011 | Krebs |
| 7,914,743 B2 | 3/2011 | Fine et al. |
| 7,947,227 B2 | 5/2011 | Fine et al. |
| 7,955,294 B2 | 6/2011 | Stenzler et al. |
| 8,030,849 B2 | 10/2011 | Suslov |
| 8,043,252 B2 | 10/2011 | Miller et al. |
| 8,057,742 B2 | 11/2011 | Rounbehler et al. |
| 8,066,904 B2 | 11/2011 | Fine et al. |
| 8,079,998 B2 | 12/2011 | Hole et al. |
| 8,083,997 B2 | 12/2011 | Rounbehler et al. |
| 8,091,549 B2 | 1/2012 | Montgomery et al. |
| 8,151,791 B2 | 4/2012 | Arlow et al. |
| 8,173,072 B2 | 5/2012 | Fine et al. |
| 8,187,544 B2 | 5/2012 | Fine et al. |
| 8,211,368 B2 | 7/2012 | Fine et al. |
| 8,221,800 B2 | 7/2012 | Fine et al. |
| 8,226,916 B2 | 7/2012 | Rounbehler et al. |
| 8,246,725 B2 | 8/2012 | Rounbehler et al. |
| 8,267,884 B1 | 9/2012 | Hicks |
| 8,268,252 B2 | 9/2012 | Fuller et al. |
| 8,277,399 B2 | 10/2012 | Hamilton et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,328,998 B2 | 12/2012 | Wada et al. |
| 8,344,627 B1 | 1/2013 | Hooke et al. |
| 8,371,296 B2 | 2/2013 | Fine et al. |
| 8,377,462 B2 | 2/2013 | DesNoyer et al. |
| 8,397,721 B2 | 3/2013 | Montgomery et al. |
| D679,366 S | 4/2013 | Fuller |
| 8,408,206 B2 | 4/2013 | Montgomery et al. |
| 8,431,163 B2 | 4/2013 | Baldassarre et al. |
| D688,352 S | 8/2013 | Montgomery et al. |
| 8,518,457 B2 | 8/2013 | Miller et al. |
| 8,573,209 B2 | 11/2013 | Bathe et al. |
| 8,573,210 B2 | 11/2013 | Bathe et al. |
| 8,574,531 B2 | 11/2013 | Miller et al. |
| 8,580,109 B2 | 11/2013 | Kruckenberg et al. |
| 8,607,785 B2 | 12/2013 | Fine et al. |
| 8,607,792 B2 | 12/2013 | Montgomery et al. |
| 8,609,026 B2 | 12/2013 | Fine et al. |
| 8,609,028 B2 | 12/2013 | Rounbehler et al. |
| 8,613,958 B2 | 12/2013 | Fine |
| 8,616,204 B2 | 12/2013 | Montgomery et al. |
| 8,646,445 B2 | 2/2014 | Fine et al. |
| D701,963 S | 4/2014 | Abarbanel et al. |
| 8,685,467 B2 | 4/2014 | Miller et al. |
| 8,701,657 B2 | 4/2014 | Fine et al. |
| 8,715,577 B2 | 5/2014 | Fine et al. |

(56) References Cited

U.S. PATENT DOCUMENTS

| | | |
|---|---|---|
| 8,717,733 B2 | 5/2014 | Gefter et al. |
| 8,720,440 B2 | 5/2014 | Montgomery et al. |
| 8,741,222 B2 | 6/2014 | Fine et al. |
| 8,757,148 B2 | 6/2014 | Montgomery et al. |
| 8,770,199 B2 | 7/2014 | Flanagan et al. |
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |
| 8,795,741 B2 | 8/2014 | Baldassarre |
| 8,808,655 B2 | 8/2014 | Solovyov et al. |
| 8,821,801 B2 | 9/2014 | Rounbehler et al. |
| 8,821,828 B2 | 9/2014 | Hilbig et al. |
| 8,846,112 B2 | 9/2014 | Baldassarre |
| 8,887,720 B2 | 11/2014 | Fine et al. |
| 8,887,721 B2 | 11/2014 | Zapol et al. |
| 8,893,717 B2 | 11/2014 | Montgomery et al. |
| 8,944,049 B2 | 2/2015 | Fine et al. |
| 9,035,045 B2 | 5/2015 | Chu et al. |
| 9,067,788 B1 | 6/2015 | Spielman et al. |
| 9,095,534 B2 | 8/2015 | Stenzler et al. |
| 9,108,016 B2 | 8/2015 | Acker et al. |
| 9,180,217 B2 | 11/2015 | Arnold et al. |
| 9,192,718 B2 | 11/2015 | Fine |
| 9,260,399 B2 | 2/2016 | Ruan et al. |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,351,994 B2 | 5/2016 | Montgomery et al. |
| 9,408,993 B2 | 8/2016 | Bathe et al. |
| 9,408,994 B2 | 8/2016 | Fine et al. |
| 9,522,249 B2 | 12/2016 | Rounbehler et al. |
| 9,550,039 B2 | 1/2017 | Flanagan et al. |
| 9,550,040 B2 | 1/2017 | Acker et al. |
| 9,562,113 B2 | 2/2017 | Ruan et al. |
| 9,573,110 B2 | 2/2017 | Montgomery et al. |
| 9,604,028 B2 | 3/2017 | Fine et al. |
| 9,701,538 B2 | 7/2017 | Fine et al. |
| 9,713,244 B2 | 7/2017 | Tabata et al. |
| 9,770,570 B2 | 9/2017 | Schnictman et al. |
| 9,795,756 B2 | 10/2017 | Flanagan et al. |
| 9,895,199 B2 | 2/2018 | Montgomery et al. |
| 9,896,337 B2 | 2/2018 | Montgomery et al. |
| 9,956,373 B2 | 5/2018 | Rounbehler et al. |
| 9,982,354 B2 | 5/2018 | Kim |
| 10,081,544 B2 | 9/2018 | Fine et al. |
| 10,086,352 B2 | 10/2018 | Fine et al. |
| 10,099,029 B2 | 10/2018 | Montgomery et al. |
| 10,124,142 B2 | 11/2018 | Rounbehler et al. |
| 10,179,222 B2 | 1/2019 | Fine et al. |
| 10,188,822 B2 | 1/2019 | Flanagan et al. |
| 10,213,572 B2 | 2/2019 | Gellman et al. |
| 10,226,592 B2 | 3/2019 | Acker et al. |
| 10,232,138 B2 | 3/2019 | Acker et al. |
| 10,239,038 B2 | 3/2019 | Zapol et al. |
| 10,279,139 B2 | 5/2019 | Zapol et al. |
| 10,286,176 B2 | 5/2019 | Zapol et al. |
| 10,293,133 B2 | 5/2019 | Zapol et al. |
| 10,328,228 B2 | 6/2019 | Zapol et al. |
| 10,398,820 B2 | 9/2019 | Potenziano et al. |
| 10,426,913 B2 | 10/2019 | Tolmie et al. |
| 10,434,276 B2 | 10/2019 | Zapol et al. |
| 10,532,176 B2 | 1/2020 | Zapol et al. |
| 10,548,920 B2 | 2/2020 | Montgomery et al. |
| 10,556,082 B2 | 2/2020 | Flanagan et al. |
| 10,556,086 B2 | 2/2020 | Goldstein et al. |
| 10,576,239 B2 | 3/2020 | Zapol et al. |
| 10,646,682 B2 | 5/2020 | Zapol et al. |
| 10,682,486 B1 | 6/2020 | Moon et al. |
| 10,695,523 B2 | 6/2020 | Zapol et al. |
| 10,737,051 B2 | 8/2020 | Gellman et al. |
| 10,750,606 B1 | 8/2020 | Liu et al. |
| 10,758,703 B2 | 9/2020 | Kohlmann et al. |
| 10,773,046 B2 | 9/2020 | Schnitman et al. |
| 10,773,047 B2 | 9/2020 | Zapol et al. |
| 10,780,241 B2 | 9/2020 | Fine et al. |
| 10,814,092 B2 | 10/2020 | Rounbehler et al. |
| 10,946,163 B2 | 3/2021 | Gillerman et al. |
| 11,007,503 B2 | 5/2021 | Zapol et al. |
| 11,033,705 B2 | 6/2021 | Zapol et al. |
| 11,045,620 B2 | 6/2021 | Hall et al. |
| 11,376,390 B2 | 7/2022 | Gillerman et al. |
| 11,478,601 B2 | 10/2022 | Hall et al. |
| 11,479,464 B2 | 10/2022 | Hall et al. |
| 11,524,134 B2 | 12/2022 | Zapol et al. |
| 11,554,240 B2 | 1/2023 | Hall et al. |
| 11,660,416 B2 | 5/2023 | McAuley et al. |
| 11,691,879 B2 | 7/2023 | Kondiboyina et al. |
| 11,754,538 B1 | 9/2023 | Fine |
| 11,827,989 B2 | 11/2023 | Silkoff et al. |
| 11,833,309 B2 | 12/2023 | Gillerman et al. |
| 11,877,378 B2 | 1/2024 | Wu et al. |
| 11,911,566 B2 | 2/2024 | Zapol et al. |
| 11,975,139 B2 | 5/2024 | Miles et al. |
| 2001/0031230 A1 | 10/2001 | Castor et al. |
| 2001/0035186 A1 | 11/2001 | Hill |
| 2002/0111748 A1 | 8/2002 | Kobayashi et al. |
| 2002/0185126 A1 | 12/2002 | Krebs |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsay |
| 2004/0050387 A1 | 3/2004 | Younes |
| 2004/0074493 A1 | 4/2004 | Seakins et al. |
| 2004/0149282 A1 | 8/2004 | Hickle |
| 2004/0168686 A1 | 9/2004 | Krebs |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0274381 A1 | 12/2005 | Deane et al. |
| 2005/0281465 A1 | 12/2005 | Marquart et al. |
| 2006/0025700 A1 | 2/2006 | Fallik |
| 2006/0090759 A1 | 5/2006 | Howes et al. |
| 2006/0172018 A1 | 8/2006 | Fine et al. |
| 2006/0173396 A1 | 8/2006 | Hatamian et al. |
| 2006/0207594 A1 | 9/2006 | Stenzler et al. |
| 2006/0276844 A1 | 12/2006 | Alon et al. |
| 2007/0051712 A1 | 3/2007 | Kooken et al. |
| 2007/0113851 A1 | 5/2007 | Delisle et al. |
| 2007/0151561 A1 | 7/2007 | Laurila |
| 2007/0181126 A1 | 8/2007 | Tolmie et al. |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0119754 A1 | 5/2008 | Hietala |
| 2008/0135044 A1 | 6/2008 | Freitag et al. |
| 2008/0176335 A1 | 7/2008 | Alberti et al. |
| 2008/0202509 A1 | 8/2008 | Dillon et al. |
| 2010/0030091 A1 | 2/2010 | Fine |
| 2010/0043789 A1 | 2/2010 | Fine et al. |
| 2010/0076325 A1 | 3/2010 | Cho et al. |
| 2010/0089392 A1 | 4/2010 | Fine et al. |
| 2010/0189808 A1 | 7/2010 | Gupta et al. |
| 2010/0275911 A1 | 11/2010 | Arlow et al. |
| 2010/0330193 A1 | 12/2010 | Baldassarre et al. |
| 2011/0140607 A1 | 6/2011 | Moore et al. |
| 2011/0240019 A1 | 10/2011 | Fine et al. |
| 2012/0093948 A1 | 4/2012 | Fine et al. |
| 2012/0279500 A1 | 11/2012 | Singvogel et al. |
| 2012/0285449 A1 | 11/2012 | Fine et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2013/0239963 A1 | 9/2013 | Goldstein et al. |
| 2013/0309328 A1 | 11/2013 | Watts et al. |
| 2014/0020685 A1 | 1/2014 | Szabo |
| 2014/0031668 A1 | 1/2014 | Mobasser et al. |
| 2014/0127081 A1 | 5/2014 | Fine et al. |
| 2014/0127330 A1 | 5/2014 | Fine et al. |
| 2014/0144436 A1 | 5/2014 | Fine et al. |
| 2014/0144444 A1 | 5/2014 | Fine et al. |
| 2014/0155684 A1 | 6/2014 | Ehrenreich |
| 2014/0158121 A1 | 6/2014 | Flanagan et al. |
| 2014/0166009 A1 | 6/2014 | Flanagan et al. |

(56) References Cited

U.S. PATENT DOCUMENTS

| 2014/0216452 A1 | 8/2014 | Miller et al. |
|---|---|---|
| 2014/0251787 A1 | 9/2014 | Montgomery et al. |
| 2014/0363525 A1 | 12/2014 | Montgomery et al. |
| 2014/0377378 A1 | 12/2014 | Baldassarre |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0075522 A1 | 3/2015 | Acker et al. |
| 2015/0090261 A1 | 4/2015 | Crosbie |
| 2015/0101600 A1 | 4/2015 | Miller et al. |
| 2015/0101604 A1 | 4/2015 | Crosbie |
| 2015/0174158 A1 | 6/2015 | Av-Gay et al. |
| 2015/0190565 A1* | 7/2015 | Ohdaira ............ B01F 23/23124 |
| | | 604/151 |
| 2015/0238248 A1 | 8/2015 | Thompson et al. |
| 2015/0272988 A1 | 10/2015 | Av-Gay et al. |
| 2015/0273176 A1 | 10/2015 | Acker et al. |
| 2015/0328430 A1 | 11/2015 | Miller et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0045685 A1 | 2/2016 | Hyde et al. |
| 2016/0106946 A1 | 4/2016 | Gellman et al. |
| 2016/0106949 A1 | 4/2016 | Kohlmann et al. |
| 2016/0121071 A1 | 5/2016 | Moon et al. |
| 2016/0151598 A1 | 6/2016 | Fine |
| 2016/0183841 A1 | 6/2016 | Duindam et al. |
| 2016/0191887 A1 | 6/2016 | Casas |
| 2016/0193336 A1 | 7/2016 | Nelson et al. |
| 2016/0228670 A1 | 8/2016 | Av-Gay et al. |
| 2016/0243328 A1 | 8/2016 | Tolmie et al. |
| 2016/0271169 A1 | 9/2016 | Potenziano et al. |
| 2016/0279165 A1 | 9/2016 | Av-Gay et al. |
| 2016/0310693 A1 | 10/2016 | Bathe et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0095634 A1 | 4/2017 | Miller et al. |
| 2017/0112871 A1 | 4/2017 | Nelson et al. |
| 2017/0128694 A1 | 5/2017 | Acker et al. |
| 2017/0143758 A1 | 5/2017 | Greenberg et al. |
| 2017/0165294 A1 | 6/2017 | Dasse et al. |
| 2017/0182088 A1 | 6/2017 | Dasse et al. |
| 2017/0232166 A1 | 8/2017 | Potenziano et al. |
| 2017/0239289 A1 | 8/2017 | Av-Gay et al. |
| 2017/0259025 A1 | 9/2017 | Fine et al. |
| 2017/0296463 A1 | 10/2017 | Minton et al. |
| 2017/0348503 A1 | 12/2017 | Westermark |
| 2018/0049622 A1 | 2/2018 | Ryan et al. |
| 2018/0071467 A1 | 3/2018 | Fine et al. |
| 2018/0104432 A1 | 4/2018 | Flanagan et al. |
| 2018/0125883 A1 | 5/2018 | Av-Gay et al. |
| 2018/0126111 A1 | 5/2018 | Moon et al. |
| 2018/0133246 A1 | 5/2018 | Av-Gay et al. |
| 2018/0169370 A1 | 6/2018 | Montgomery et al. |
| 2018/0228836 A1 | 8/2018 | Nelson et al. |
| 2018/0243527 A1 | 8/2018 | Zapol et al. |
| 2018/0243528 A1 | 8/2018 | Zapol et al. |
| 2018/0264032 A1 | 9/2018 | Jaffri et al. |
| 2018/0280920 A1 | 10/2018 | Zapol et al. |
| 2018/0296790 A1 | 10/2018 | Zapol et al. |
| 2018/0304038 A1 | 10/2018 | Jafri et al. |
| 2018/0311460 A1 | 11/2018 | Rounbehler et al. |
| 2018/0328842 A1 | 11/2018 | Kjaer |
| 2019/0038864 A1 | 2/2019 | Montgomery et al. |
| 2019/0083699 A1* | 3/2019 | Spohn .................. A61M 5/007 |
| 2019/0092639 A1 | 3/2019 | Fine et al. |
| 2019/0127223 A1 | 5/2019 | Montgomery et al. |
| 2019/0134574 A1* | 5/2019 | Tsuchiya .......... B01F 25/43231 |
| 2019/0135633 A1 | 5/2019 | Montgomery et al. |
| 2019/0143068 A1 | 5/2019 | Rounbehler et al. |
| 2019/0184116 A1 | 6/2019 | Acker et al. |
| 2019/0209993 A1 | 7/2019 | Fine et al. |
| 2019/0217042 A1 | 7/2019 | Zapol et al. |
| 2019/0217043 A1 | 7/2019 | Fine et al. |
| 2019/0233288 A1 | 8/2019 | Montgomery et al. |
| 2019/0233289 A1 | 8/2019 | Montgomery et al. |
| 2019/0276313 A1 | 9/2019 | Montgomery et al. |
| 2019/0314596 A1 | 10/2019 | Zapol et al. |
| 2019/0374739 A1 | 12/2019 | Tolmie et al. |
| 2020/0030553 A1 | 1/2020 | Keip et al. |
| 2020/0094011 A1 | 3/2020 | Zapol et al. |
| 2020/0139071 A1 | 5/2020 | Fine et al. |
| 2020/0139072 A1 | 5/2020 | Zapol et al. |
| 2020/0139073 A1 | 5/2020 | Tector et al. |
| 2020/0163989 A1 | 5/2020 | Montgomery et al. |
| 2020/0171259 A1 | 6/2020 | Flanagan et al. |
| 2020/0171264 A1 | 6/2020 | Goldstein et al. |
| 2020/0180958 A1 | 6/2020 | Fine et al. |
| 2020/0188319 A1 | 6/2020 | Quinn et al. |
| 2020/0197318 A1* | 6/2020 | Widgerow ............... A61K 9/08 |
| 2020/0254199 A1 | 8/2020 | Bassin |
| 2020/0282375 A1 | 9/2020 | Fine et al. |
| 2020/0308032 A1* | 10/2020 | Domrese ................. B01F 23/29 |
| 2020/0360647 A1 | 11/2020 | Quinn et al. |
| 2020/0360649 A1 | 11/2020 | Hall et al. |
| 2020/0360690 A1 | 11/2020 | Evans et al. |
| 2020/0361772 A1 | 11/2020 | Hall et al. |
| 2020/0361773 A1 | 11/2020 | Gillerman et al. |
| 2020/0390994 A1 | 12/2020 | Gillerman et al. |
| 2021/0214222 A1 | 7/2021 | Kondiboyia et al. |
| 2021/0220586 A1 | 7/2021 | Shah et al. |
| 2021/0268221 A1 | 9/2021 | Gillerman et al. |
| 2021/0330957 A1 | 10/2021 | Potenziano et al. |
| 2021/0353898 A1 | 11/2021 | Hall et al. |
| 2021/0386954 A1 | 12/2021 | Tamiya et al. |
| 2021/0395905 A1 | 12/2021 | Silkoff et al. |
| 2022/0047837 A1 | 2/2022 | Zapol et al. |
| 2022/0080147 A1 | 3/2022 | Shah et al. |
| 2022/0096535 A1 | 3/2022 | Shah et al. |
| 2022/0135406 A1 | 5/2022 | Apollonio et al. |
| 2022/0162070 A1 | 5/2022 | Silkoff et al. |
| 2022/0193623 A1* | 6/2022 | Nakao ..................... B01F 31/85 |
| 2022/0211967 A1 | 7/2022 | Hall et al. |
| 2022/0296845 A1 | 9/2022 | Jackson et al. |
| 2022/0298653 A1 | 9/2022 | Silkoff et al. |
| 2022/0339391 A1 | 10/2022 | Gillerman et al. |
| 2022/0395787 A1* | 12/2022 | Hamler ............... B01F 25/4413 |
| 2023/0001119 A1 | 1/2023 | Richardson et al. |
| 2023/0053201 A1 | 2/2023 | Miles et al. |
| 2023/0058407 A1* | 2/2023 | Hall .................. B01F 25/31241 |
| 2023/0098706 A1 | 3/2023 | Miles et al. |
| 2023/0112963 A1 | 4/2023 | Yuen et al. |
| 2023/0149556 A1 | 5/2023 | Hall et al. |
| 2023/0158064 A1 | 5/2023 | Shah |
| 2023/0158260 A1 | 5/2023 | Shah et al. |
| 2023/0158261 A1 | 5/2023 | Trias et al. |
| 2023/0201497 A1 | 6/2023 | Dekker |
| 2023/0263986 A1 | 8/2023 | Hall et al. |
| 2023/0330359 A1 | 10/2023 | Scholz et al. |
| 2024/0067523 A1 | 2/2024 | Hall et al. |
| 2024/0076185 A1 | 3/2024 | Hall et al. |
| 2024/0076186 A1 | 3/2024 | Kondiboyina et al. |
| 2024/0209521 A1 | 6/2024 | Silkoff et al. |
| 2024/0253990 A1 | 8/2024 | Apollonio et al. |
| 2024/0325672 A1 | 10/2024 | Gillerman et al. |
| 2025/0128946 A1 | 4/2025 | Silkoff et al. |

FOREIGN PATENT DOCUMENTS

| CN | 1730115 | 2/2006 |
|---|---|---|
| CN | 201037113 | 3/2008 |
| CN | 100404083 | 7/2008 |
| CN | 101036482 | 12/2010 |
| CN | 110662339 A | 1/2020 |
| CN | 110872714 | 3/2020 |
| DE | 101 51 270 | 10/2006 |
| EP | 621051 | 10/1994 |

(56) References Cited

FOREIGN PATENT DOCUMENTS

| EP | 0763500 | | 3/1997 |
|----|---------|---|--------|
| EP | 0878208 | | 11/1998 |
| EP | 1036758 | | 9/2000 |
| EP | 2151554 | | 2/2010 |
| EP | 1854494 | | 6/2012 |
| EP | 2565157 | | 10/2017 |
| EP | 3372267 | | 12/2018 |
| JP | H04132560 | | 5/1992 |
| JP | 2000102616 | | 4/2000 |
| JP | 2003339872 | A | 12/2003 |
| JP | 2004065636 | | 3/2004 |
| JP | 2006273677 | | 10/2006 |
| KR | 100841741 | | 6/2008 |
| KR | 20100087977 | | 8/2010 |
| RU | 2199167 | | 2/2003 |
| WO | WO199507610 | | 3/1995 |
| WO | WO2004032719 | | 4/2004 |
| WO | WO2005094138 | | 10/2005 |
| WO | WO2005110441 | | 11/2005 |
| WO | WO2008/019102 | | 2/2008 |
| WO | WO2008/112143 | | 9/2008 |
| WO | 2008116991 | A2 | 10/2008 |
| WO | WO2009018837 | | 2/2009 |
| WO | WO2010021944 | | 2/2010 |
| WO | WO2011/002606 | | 1/2011 |
| WO | WO2012014805 | | 2/2012 |
| WO | WO2012/034089 | | 3/2012 |
| WO | WO2012/094008 | | 7/2012 |
| WO | WO2012/155213 | | 11/2012 |
| WO | WO2013/052548 | | 4/2013 |
| WO | WO2013/070712 | | 5/2013 |
| WO | WO2013/181179 | | 12/2013 |
| WO | WO2014/085719 | | 6/2014 |
| WO | 2014144184 | A2 | 9/2014 |
| WO | WO2014/143842 | | 9/2014 |
| WO | WO2014/144151 | | 9/2014 |
| WO | WO2015/049783 | | 4/2015 |
| WO | WO2015/066278 | | 5/2015 |
| WO | WO2015/127085 | | 8/2015 |
| WO | 2015168517 | A1 | 11/2015 |
| WO | 2015172160 | A1 | 11/2015 |
| WO | WO2016/064863 | | 4/2016 |
| WO | WO2018/157172 | | 8/2018 |
| WO | WO2018/157175 | | 8/2018 |
| WO | WO2019/046413 | | 3/2019 |
| WO | WO2019/046415 | | 3/2019 |
| WO | WO2019/133776 | | 7/2019 |
| WO | WO2019/133777 | | 7/2019 |
| WO | WO2019/222640 | | 11/2019 |
| WO | WO2020/033768 | | 2/2020 |
| WO | WO2020/115473 | | 6/2020 |
| WO | WO2020/142658 | | 7/2020 |
| WO | WO2020/148155 | | 7/2020 |
| WO | WO2020/150195 | | 7/2020 |
| WO | WO2020/232414 | | 11/2020 |
| WO | WO2020/232419 | | 11/2020 |
| WO | WO2021/087382 | | 5/2021 |
| WO | WO2021/142472 | | 7/2021 |
| WO | 2021154833 | A1 | 8/2021 |
| WO | WO2021/245667 | | 12/2021 |
| WO | WO2021/258025 | | 12/2021 |
| WO | WO2022/123567 | | 6/2022 |
| WO | WO2022/123574 | | 6/2022 |
| WO | WO2022/123580 | | 6/2022 |
| WO | 2022192757 | A1 | 9/2022 |
| WO | 2023018992 | A1 | 2/2023 |
| WO | 2023049873 | A1 | 3/2023 |
| WO | 2023092103 | A1 | 5/2023 |
| WO | 2023201363 | A1 | 10/2023 |

OTHER PUBLICATIONS

International Search Report in PCT Application No. PCT/US2023/065813 mailed Oct. 3, 2023.

Arjunan Thesis—Plasma Produced Reactive Oxygen and Nitrogen Species in Angiogenesis—May 2011—Krishna Priya Arjunan.

Arora et al., Nitric Oxide Regulation of Bacterial Biofilms, Biochemistry, vol. 54, pp. 3717-3728, May 21, 2015.

Barraud et al., Involvement of Nitric Oxide n Biofilm Dispersal of Pseudomonas Aeruginosa, Journal of Bacteriology, vol. 188, No. 21, pp. 7344-7353, Nov. 2006.

Bellerophon, "A Dose Escalation Study to Assess the Safety and Efficacy of Pulsed iNO in Subjects With Pulmonary Fibrosis", Aug. 30, 2017, https://clinicaltrials.gov/ct2/show/NCT03267108.

Bentur et al., Pilot Study to Test Inhaled Nitric Oxide in Cystic Fibrosis Patients with Refractory *Mycobacterium abscessus* Lung Infection, Journal of Cystic Fibrosis, vol. 19, pp. 225-231, May 23, 2019.

Birkeland, K., "On the Oxidation of Atmospheric Nitrogen in Electric Arcs", A Paper read before the Faraday Society on Monday, Jul. 2, 1906, Published on Jan. 1, 1906.

Bogdonovski et al., Anti-Mycobacterial Activity of High-Dose Nitric Oxide Against *Mycobacterium abscessus* In Vitro, National Institutes of Health Poster, Jul. 8, 2018.

Charles, et al., "SiO2 Deposition from Oxygen/Silane Pulsed Helicon Diffusion Plasmas" Applied Physics Letters, vol. 67, No. 1, pp. 40-42, Jul. 3, 1995.

Deppisch et al., Gaseous Nitric Oxide to Treat Antibiotic Resistant Bacterial and Fungal Lung Infections in Patients with Cystic Fibrosis: A Phase I Clinical Study, Infection, vol. 44, pp. 513-520, Feb. 9, 2016.

Dobrynin et al. "Direct and Controllable Nitric Oxide Delivery into Biological Media and Living Cells by a Pin-to-Hole Spark Discharge (PHD) Plasma" Journal of Physics D: Applied Physics, vol. 44, pp. 1-10, Jan. 28, 2011.

Donohoe et al., "Production of O3, NO, and N2O in a Pulsed Discharge at 1 Atm", Ind. Eng. Chem., Fundam., vol. 16, No. 2, pp. 208-215, May 1977.

Encyclopaedia Britannica, "Soda Lime" published Nov. 12, 2018, https://www.britannica.com/science/soda-lime.

Feigerle, C., et al., "Multiphoton Ionization of Vibrationally Hot Nitric Oxide Produced in a Pulsed Supersonic Glow Discharge", Journal of Chemical Physics, vol. 90, Issue 6, pp. 2900-2908, Mar. 15, 1989.

Fowler, "Exercise Intolerance in Pulmonary Arterial Hypertension", Pulmonary Medicine, vol. 2012, Article ID 39204, 11 pages, (2012).

Habib, Bassam Hanna, "A Simple Model of Spark Gap Discharge Phase", Eng. & Tech. Journal, vol. 31, Part (A), No. 9, pp. 1692-1704, 2013.

Hanning et al., "Pulse Oximetry: A Practical Review", British Medical Journal, vol. 311, pp. 367-370, Aug. 5, 1995.

Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages (Includes English Language Translation of Title Page and Abstract).

Higenbottam et al., "The Direct and Indirect Action of Inhaled Agents on the Lung and Its Circulation: Lessons from Clinical Science," Environmental Health Perspectives, vol. 109, Supplement 4, pp. 559-562, Aug. 2001.

Howlin et al., Low-Dose Nitric Oxide as Targeted Anti-Biofilm Adjunctive Therapy to Treat Chronic Pseudomonas Aeruginosa Infection in Cystic Fibrosis, Molecular Therapy, vol. 25, No. 9, pp. 2104-2116, Sep. 2017.

Hu, Hui et al., "Study on Production of Nitric Monoxide for Respiratory Distress by Pulsed Discharge", Proceedings of the CSEE, vol. 23, No. 2, Jan. 2005.

Hu, Hui et al., "Study on Pulsed Arc Discharge Conditions on Production of Nitric Oxide for Medical Application", High Voltage Apparatus, Issue 3, Mar. 2005.

Hu et al., "Study on Production of Inhaled Nitric Oxide for Medical Applications by Pulsed Discharge" IEEE Transactions on Plasma Science, vol. 35, No. 3, pp. 619-625, Jun. 2007.

Hu, Hui et al., "The Effect of Flow Distribution on the Concentration of NO Produced by Pulsed Arc Discharge", Plasma Science and Technology, vol. 9, No. 6, pp. 766-769, Dec. 2007.

(56)            References Cited

OTHER PUBLICATIONS

Hu, Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 138 pages (Includes English Language Translation of Title Page and Abstract).

Intersurgical Complete Respiratory Systems, Carbon Dioxide Absorbents Catalogue, www.intersurgical.com/distributors, Issue 5, Oct. 17, 2021.

Johns Hopkins University—"American Chemical Journal vol. XXXV"—No. 4, Reports Chapter, pp. 358-368, Apr. 1906.

Keshav, Saurabh. "Using Plasmas for High-speed Flow Control and Combustion Control" Diss. The Ohio State University, 2008.

Kornev, J., et al., "Generation of Active Oxidant Species by Pulsed Dielectric Barrier Discharge in Water-Air Mixtures", Ozone: Science & Engineering, vol. 28, Issue 4, pp. 207-215, Jul. 2006.

Kuo, Spencer P. "Air Plasma for Medical Applications" J. Biomedical Science and Engineering, vol. 5, pp. 481-495, Sep. 2012.

Li, Z. et al., "Development of Miniature Pulsed Power Generator," 2005 IEEE Pulsed Power Conference, Monterey, CA, pp. 1053-1056, Jul. 2005.

Li et al., Production of Medically Useful Nitric Monoxide Using AC Arc Discharge, Nitric Oxide, vol. 73, pp. 89-95, Feb. 28, 2018.

Lorente L., "Respiratory Filters and Ventilator-Associated Pneumonia: Composition, Efficacy Tests and Advantages and Disadvantages", Humidification in the Intensive Care Unit, pp. 171-177, Springer, Berlin, Heidelberg 2012.

Lovich et al., "Generation of Purified Nitric Oxide from Liquid N204 for the Treatment of Pulmonary Hypertension in Hypoxemic Swine", Nitric Oxide vol. 37, pp. 66-77, Feb. 15, 2014.

Matsuo, K. et al., "Nitric Oxide Generated by Atmospheric Pressure Air Microplasma," 2009 IEEE Pulsed Power Conference, Washington, DC, Jun. 28-Jul. 2, 2009, pp. 999-1003, Jan. 19, 2010.

McMullin et al., The Antimicrobial Effect of Nitric Oxide on the Bacteria That Cause Nosocomial Pneumonia in Mechanically Ventilated Patients in the Intensive Care Unit, Respiratory Care, vol. 50, No. 11, pp. 1451-1456, Nov. 2005.

Miller et al., Gaseous Nitric Oxide Bactericidal Activity Retained During Intermittent High-Dose Short Duration Exposure, Nitric Oxide, vol. 20, Issue 1, pp. 16-23, Feb. 2009.

Miller et al., Inhaled Nitric Oxide Decreases the Bacterial Load in a Rat Model of Pseudomonas Aeruginosa Pneumonia, Journal of Cystic Fibrosis, vol. 12, pp. 817-820, Mar. 6, 2013.

Miller et al., Nitric Oxide is a Potential Antimicrobial Against Slow and Fast Growing Mycobacteria, Online Abstracts Issue, American Journal Respiratory Care Medicine, vol. 193, A7498, May 18, 2016.

Miller et al., A Phase I Clinical Study of Inhaled Nitric Oxide in Healthy Adults, Journal of Cystic Fibrosis, vol. 11, pp. 324-331, Apr. 18, 2012.

Mok et al. "Application of Positive Pulsed Corona Discharge to Removal of SO2 and NOx," Proceedings, ICESP VII, Sep. 20-25, 1998, Kyongiu, Korea.

Namihira et al., Production of Nitric Monoxide Using Pulsed Discharges for a Medical Application, IEEE Transactions on Plasma Science, vol. 28, No. 1, pp. 109-114, Feb. 2000.

Namihara et al., "Production of NO Using Pulsed Arc Discharges and Its Medical Applications", Journal of Plasma and Fusion Research, vol. 79, No. 1 pp. 35-38, Jun. 25, 2002.

Namihira et al., "Production of Nitric Monoxide in Dry Air Using Pulsed Discharge," Digest of Technical Papers. 12th IEEE International Pulsed Power Conference. (Cat. No. 99CH36358), Monterey, CA, pp. 1313-1316 vol. 2, Aug. 6, 2002.

Namihira et al., Production of Nitric Oxide Using a Pulsed Arc Discharge, IEEE Transactions on Plasma Science, vol. 30, No. 5, pp. 1993-1998, Oct. 2002.

Namihira et al., "Temperature and Nitric Oxide Generation in a Pulsed Arc Discharge Plasma" Plasma Science and Technology, vol. 9, No. 6, pp. 747-751, Dec. 2007.

Navarro-Gonzalez et al., "The Physical Mechanism of Nitric Oxide Formation in Simulated Lightning" Geophysical Research Letters, vol. 28, No. 20, pp. 3867-3870, Oct. 15, 2001.

Olivier et al., Treatment of Refractory Mycobacterium Abscessus Lung Infection with Inhaled Intermittent Nitric Oxide, Poster, Jul. 8, 2018.

Overzet, et al. "Why and How to Pulse a Plasma"—slide show presentation, Oct. 1997.

Patil et al., Plasma Assisted Nitrogen Oxide Production from Air, AiChE Journal, vol. 64, Issue 2, Aug. 14, 2017.

Pawlat et al., Evaluation of Oxidative Species in Gaseous, Plasma Chemistry and Plasma Processing, vol. 39, pp. 627-642, Mar. 28, 2019.

Pontiga, F., et al., "Nitrogen Oxides Generation Induced by Negative Corona Discharge in N2+02 Mixtures," 2006 IEEE Conference on Electrical Insulation and Dielectric Phenomena, Kansas City, MO, pp. 264-267, Oct. 2006.

Sakai, et al., "A Compact Nitric Oxide Supply for Medical Application," 2007 16th IEEE International Pulsed Power Conference, Albuquerque, NM, pp. 752-755, Oct. 14, 2008.

Sakai et al., "Nitric Oxide Generator Based on Pulsed Arc Discharge" Acta Physica Polonica A, vol. 115, No. 6, pp. 1104-1106, Jun. 2009.

Schilz, "Treatment of Pulmonary Hypertension Related to Disorders of Hypoxia" Advances in Pulmonary Hypertension, vol. 4, No. 2, pp. 14-22, May 2005.

Takaki, et al., "Resistance of Pulsed Arc Discharge in Air and SF/sub 6", Pulsed Power Plasma Science, vol. 2, pp. 1758-1761, Jun. 2001.

Tal et al., Nitric Oxide Inhalations in Bronchiolitis: A Pilot, Randomized, Double-Blinded, Controlled Trial, Pediatric Pulmonology, vol. 53, Issue 1, pp. 95-102, Jan. 2018.

Tsukahara et al., "Gas-Phase Oxidation of Nitric Oxide: Chemical Kinetics and Rate Constant," Nitric Oxide: Biology and Chemistry, vol. 3, No. 3, pp. 191-198, Jun. 1999.

Wang et al., Gliding Arc Plasma for CO2 Conversion, Chemical Engineering Journal, vol. 330, pp. 11-25, 2017.

Yaacoby-Bianu et al., Compassionate Nitric Oxide Adjuvant Treatment of Persistent *Mycobacterium* Infection in Cystic Fibrosis Patients, The Pediatric Infectious Disease Journal, vol. 37, No. 4, Apr. 2018.

Yu, et al., "Detection and Removal of Impurities in Nitric Oxide Generated from Air by Pulsed Electrical Discharge", Nitric Oxide, vol. 60, pp. 16-23, Nov. 30, 2016.

Yu, et al. "Development of a Portable Mini-Generator to Safely Produce Nitric Oxide for the Treatment of Infants with Pulmonary Hypertension", Nitric Oxide, vol. 75, pp. 7-76, May 1, 2018.

Beanland et al., "PreInsertion Resistors in High Voltage Capicitor Bank Switching", prepared for Western Protective Relay Conference, Oct. 19-21, 2004, Spokane, WA.

DiBlasi et al., "Evidence-Based Clinical Practice Guideline: Inhaled Nitric Oxide for Neonates With Acute Hypoxic Respiratory Failure", Respiratory Care (2010), vol. 55, No. 12, pp. 1717-1745.

Edwards et al., "Current Modes of Conventional Ventilation in Intensive Care", BJA CEPD Reviews, vol. 2, No. 2, pp. 41-44, Apr. 1, 2002.

Ehrenwerth et al., Anesthesia Equipment, Principles and Applications, Chapter 6, Anesthesia Ventilators, pp. 140-171, Mosby Publishing, 1993.

Engstrom Ventilator Technical Reference Manual.

Ikaria, INOmax DSIR® Operation Manual (2012).

Kirmse et al., "Delivery of Inhaled Nitric Oxide Using the Ohmeda INOvent Delivery System", Chest (1998), vol. 113, Issue 6, pp. 1650-1657.

Maeda et al., "Generation Mechanism of Micro-Bubbles in a Pressurized Dissolution Method", Experimental Thermal and Fluid Science, vol. 60, pp. 201-207, Jan. 1, 2015.

Malik, "Nitric Oxide Production by High Voltage Electrical Discharges for Medical Uses: A Review" Plasma Chem Plasma Process, (2016), vol. 36, pp. 737-766.

Montgomery et al., "Inhaled Nitric Oxide Delivery and Monitoring", Journal of Clinical Monitoring and Computing (1999), vol. 15, pp. 325-335.

(56) References Cited

OTHER PUBLICATIONS

Shoobert et al., "Iridium Electrodes Increase Spark Plug Life", Platinum Metals Rev., 1962, vol. 6, No. 3, pp. 92-94.
Ventilator/Respirator Hardware and Software Design Specification, Rev. 0, Nov. 2011, Freescale Semiconductor, Inc.
Young et al., "Delivery and monitoring of inhaled nitric oxide", Intensive Care Med. (1996), vol. 22, pp. 77-86.

* cited by examiner

Exemplary System Faults

| Fault | Name/ Purpose | Triggering condition | System response | User message |
|---|---|---|---|---|
| 1 | Solution Concentration | Gas concentration in solution < Min value | Enter Idle state, Alarm | "Check liquid volume, temperature, gas pressure." |
| 2 | Pump tubing missing | User enters generation mode & pump tube not detected | Enter Idle state, Alarm | "Insert tubing into pump head." |
| 3 | Gas pressure low | Gas reservoir pressure < Min value | Enter Idle state, Alarm | "Connect / replace gas source." |
| 4 | Liquid volume low | Mass of liquid reservoir < threshold value | Enter Idle state, Alarm | "Replace liquid reservoir and restart generation." |
| 5 | Liquid volume high | Mass of liquid reservoir > threshold value | Enter Idle state, Alarm | "Check liquid reservoir." |
| 6 | Tube set expired | Tube set expiration date < current date | Enter Idle state, Alarm | "Replace tube set" |
| 7 | Pump jam / failure | No pump encoder response to Pump ON command | Enter Idle state, Alarm | "Check pump for obstruction." |
| 8 | Solution pH | Solution pH < threshold | Enter Idle state, Alarm | "Replace liquid." |

FIG. 5

Syringe Port

Venturi/tube connector

Power cord

420

Upper fitting

430

Gas
Pump

422

NB
Generator

426

Liquid
Pump

424

Medicinal Gas

Liquid

Liquid return

Liquid out

Port

428

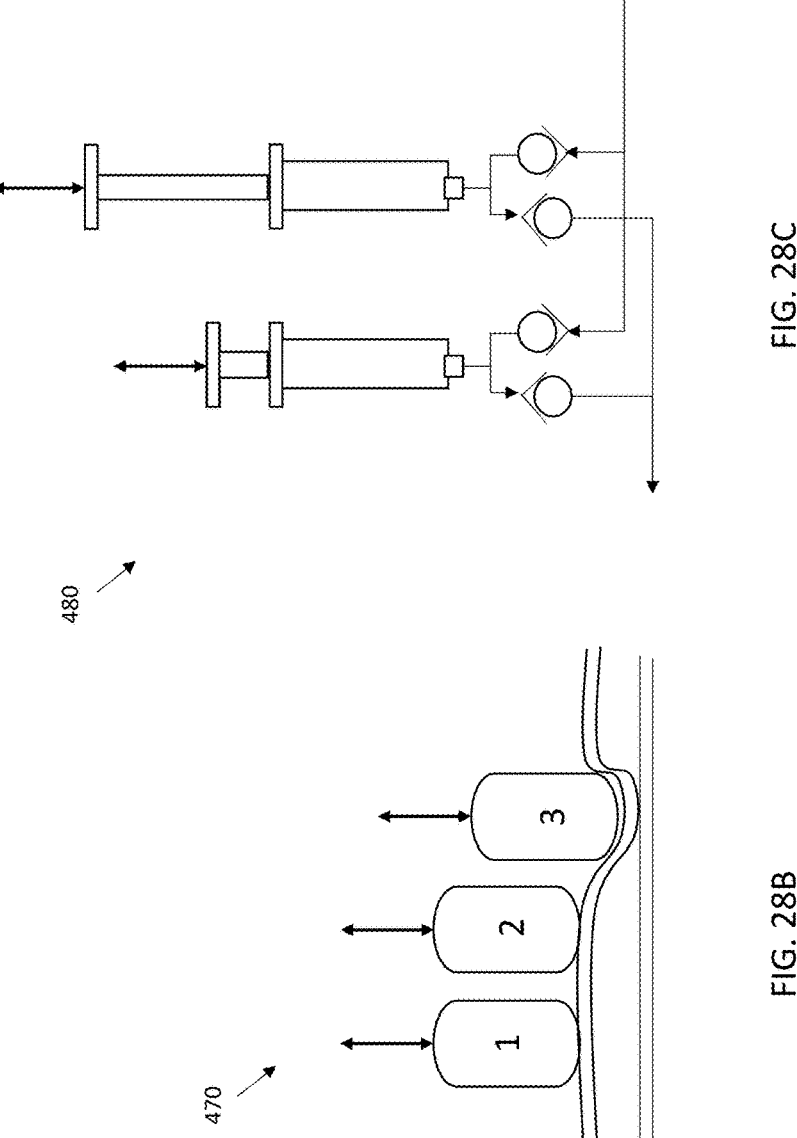
FIG. 28C
FIG. 28B
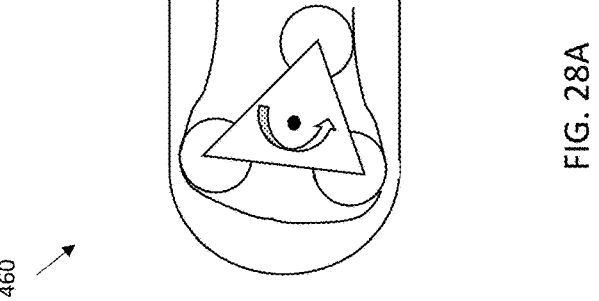
FIG. 28A

490

Reusable

Disposable

Check valve

Actuator

Bulb

Check valve

550

NO Nanobubble Solution with Buffering Agents

Solution generated with 20,000ppm NO

Flow control valve

618

Pressurized Gas

Pressurized Liquid

616

614

612

Delivery device

610

670

672
674
676

678

Membrane

S C B
⊗

Liquid
Delivery

Liquid
Return

1. Tight navigation spot
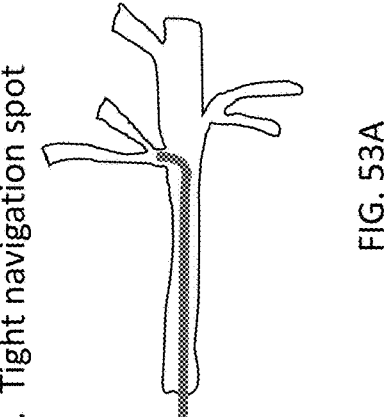
FIG. 53A
2. Introduce NO nanobubbles
FIG. 53B
3. Vessel dilates, easier to pass
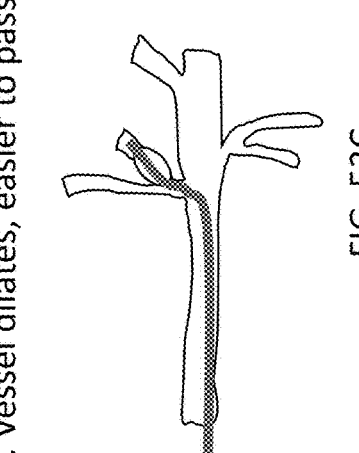
FIG. 53C 3. Vessel dilates, remove clot 2. Introduce NO nanobubbles 1. Infarct in vessel

DELIVERY OF MEDICINAL GAS IN A LIQUID MEDIUM

RELATED APPLICATIONS

This application claims the benefit of and priority to U.S. Provisional Application No. 63/331,160 filed Apr. 14, 2022, U.S. Provisional Application No. 63/375,446 filed Sep. 13, 2022, and U.S. Provisional Application No. 63/488,341 filed Mar. 3, 2023, and the contents of each of these applications are hereby incorporated herein by reference in their entireties.

FIELD

The present disclosure relates to systems and methods for delivering medicinal gas using a liquid medium.

BACKGROUND

Nitric oxide gas is commonly administered to a patient in gaseous form. However, there are challenges in delivery and managing NO in the gaseous form. NO rapidly combines with oxygen to form nitrogen dioxide, a harmful chemical. NO oxidation occurs whenever oxygen is present, including during storage within cannisters that are not completely cleaned, delivery of NO through systems that have not been completely purged of oxygen, and dilution of NO by another gas that contains oxygen. A further complication is that NO is highly reactive with other materials, including tubing, delivery systems and storage containers, requiring specific materials for storage and delivery.

Aside from air pollution (e.g., vehicle exhaust) and atmospheric discharge (e.g., lightning strikes), NO does not normally appear in ambient air. This rarity combined with NO being a very small molecule makes it have a strong propensity to leak out of gaseous NO handling systems, further increasing the complexity of working with it as a gas. NO is often stored or diluted with inert gases (e.g., $N_2$, Argon, $CO_2$) to achieve lower concentrations that are relatively more stable and clinically relevant. The act of diluting the NO, however, can introduce errors in the NO concentration.

Despite these challenges and complications, NO is delivered as a gas in the clinic. The usual route of delivery is inhalation (e.g., for hemodynamic effect, increasing oxygenation, or treating infections). In some research studies, topical application (e.g., for disinfection and promotion of blood flow) and more invasive approaches (e.g., cancerous tumor treatment) have been employed with gaseous NO.

Some research has been conducted into delivering NO as a particle. For example, nanoparticles of nitric oxide gas encapsulated in lipid membranes or shells have been evaluated. Delivery of pure NO that is not encapsulated within or released from another material provides the benefit of fewer potential host responses and fewer complexities (i.e. sensitivity, side effects) from the patient's physiology. That said, clinical applications identified herein are applicable to all types of NO-containing solution, including but not limited to NO nanobubbles, NO microbubbles, shelled NO bubbles, and NO-donor particles.

SUMMARY

The present disclosure is directed to systems and methods for delivering a gas in the form of nanobubbles and/or a dissolved gas using a liquid medium. In some embodiments, systems and methods involving the delivery of nitric oxide to enhance uptake and/or delivery of other drugs are presented.

A nanobubble generation system for generating a medicinal solution is provided, and in some embodiments includes a reservoir configured to store a liquid, a source of medicinal gas, a pump configured to propel the liquid from the reservoir, and a nanobubble generator in fluid communication with the reservoir and the source of medicinal gas. The nanobubble generator is configured to form a nanobubble solution including nanobubbles of the medicinal gas in the liquid. A return flow path is configured to deliver the nanobubble solution exiting the nanobubble generator to the liquid reservoir such that the nanobubble solution passes through the nanobubble generator and the reservoir a plurality of times.

In some embodiments, the system further includes a delivery device configured to deliver a portion of the nanobubble solution exiting the reservoir to a target tissue to treat a medical condition in a patient. In some embodiments, the delivery device includes a syringe port, a syringe, a needle, and a catheter to deliver the nanobubble solution to the target tissue.

In some embodiments, the pump is at least one of a peristaltic pump, a syringe pump, a screw pump, a gear pump, and a diaphragm pump.

In some embodiments, the liquid reservoir is removable. In some embodiments, the liquid reservoir is in the form of a bag. In some embodiments, the liquid is in the form of at least one of an aqueous solution, a lipid, and an alcohol. In some embodiments, the liquid is at least one of sesame oil, silicone oil, mineral oil, ethanol, isopropyl alcohol, heparin, saline, heparinized saline, lactated Ringer's solution, phosphate-buffered saline, and biological fluids. In some embodiments, the liquid includes a pH buffer.

In some embodiments, the gas is one or more of nitric oxide, carbon monoxide, carbon dioxide, ozone, oxygen, helium, nitrogen, nitrous oxide, argon, xenon, and an anesthetic. In some embodiments, the nanobubble generator is in the form of a venturi.

In some embodiments, a concentration of nanobubbles in the nanobubble solution is modulated by one or more of temperature, a concentration of the gas, pH of the liquid, a flow rate of the liquid, pressure of the medicinal gas from the source, pressure of gas in the reservoir, number of passes through a recirculation loop, quantity of gas added to the liquid, viscosity of the liquid, time since nanobubble solution creation, nanobubble generator operating time, and osmolality.

In some embodiments, a dose of nanobubble solution is configured to be modulated by one or more of the quantity of dissolved and nanobubble gas in the liquid and the quantity of liquid delivered. In some embodiments, the nanobubble solution is removed from the system intermittently. In some embodiments, the nanobubble solution is configured to be removed from the system continuously.

In some embodiments, the system further includes a flow path configured to vent excess gas from the system. In some embodiments, excess gas is scrubbed before release from the system. In some embodiments, the system further includes one or more of a valve and a pump to control flow through a gas vent.

In some embodiments, a molarity of the gas in the liquid is from about 0.1 mM to 3 mM.

In some embodiments, the system further includes a temperature modulation component configured to chill at least one of the liquid upstream of the nanobubble generator, the nanobubble solution downstream of the nanobubble generator, and the liquid reservoir.

In some embodiments, the nanobubbles are used to treat a medical condition that is at least one of cancer, open wound, urinary tract infection, eye infection, organ transplant, skin graft, fungal infection, bacterial infection, viral infection, kidney disease, diabetes, myocardial infarct, stroke, atherosclerotic lesion, thrombus, blood disease, hair loss, and vasospasm.

A nanobubble generation system for generating a medicinal solution is provided, and includes a reservoir configured to store a liquid, a source of medicinal gas, and a nanobubble generator in fluid communication with the reservoir and the source of medicinal gas. The nanobubble generator is configured to form a nanobubble solution of nanobubbles of the medicinal gas in the liquid. A return flow path is configured to deliver the nanobubble solution exiting the nanobubble generator to the liquid reservoir such that the nanobubble solution passes through the nanobubble generator and the reservoir a plurality of times, wherein at least a portion of the nanobubble solution is used to one or more of prevent and treat a vasospasm in a blood vessel.

A nanobubble generation kit for generating a medicinal solution is provided, and includes a reservoir configured to store a liquid, a source of medicinal gas, and a nanobubble generator in fluid communication with the reservoir and the source of medicinal gas. The nanobubble generator is configured to form a nanobubble solution of nanobubbles of the medicinal gas in the liquid. A return flow path is configured to deliver the nanobubble solution exiting the nanobubble generator to the liquid reservoir such that the nanobubble solution passes through the nanobubble generator and the reservoir a plurality of times. A delivery mechanism is configured to deliver at least a portion of the nanobubble solution to a target tissue to treat a medical condition.

In some embodiments, the delivery mechanism can include a syringe port, a syringe, a needle, and a catheter to deliver the nanobubble solution to the target tissue.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 5 illustrates exemplary system faults;

FIG. 28A depicts an exemplary embodiment of a rotary peristaltic pump;

FIG. 28B depicts an exemplary embodiment of a linear peristaltic pump;

FIG. 28C depicts an exemplary embodiment of a dual syringe pump;

FIGS. 53A, 53B, and 53C depict exemplary delivery of nanobubble solution through a catheter to facilitate catheter navigation;

Figure 1C:
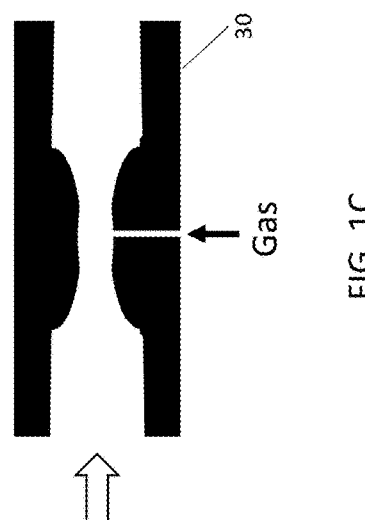
FIG. 1C depicts a method of nanobubble generation that utilizes a venturi.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments. Figures depicting architectures forgo the details of also depicting cabling and control elements to provide focus on the innovation.

NO can be sourced in a variety of ways, including but not limited to electrical generation, a compressed NO gas cylinder, reduction of $NO_2$ gas, release from a NO-donor molecule and other methods. It should be understood that embodiments presented herein are not limited to the NO source depicted and not all potential combinations of NO delivery systems and NO sources have been presented.

Although the majority of examples presented refer to NO as the medicinal gas delivered to a patient, the same approaches can be applied to other medicinal gases including but not limited to anesthetic gases, oxygen, helium, nitrous oxide, and carbon monoxide. Combinations of medicinal gases within individual bubbles or as an assortment of different gas-containing bubbles are also within the scope of this invention.

Although many of the medicinal gas applications in this disclosure pertain to the unique properties of nanobubbles, some of the applications (e.g., non-vascular applications) can be performed with larger bubbles such as microbubbles.

The controller is not depicted on all figures for simplicity, but a person skilled in the art will understand that sensors and fluid control elements can be controlled by a microprocessor, field programmable gate array, or other control device in any of the embodiments described herein.

Many embodiments include a pump for moving liquid, gas or nanobubble solution through a system. Except where noted, various types of pump can be utilized for each application, including but not limited to peristaltic (linear or rotary), diaphragm, gear, screw, syringe (single or out of phase double for continuous flow), screw, and others. Alternatively, liquid can move passively from a location of high pressure to a location of lower pressure within a system. Pressure can be applied to a liquid by gas pressure or mechanically (e.g. piston or diaphragm). In embodiments where gas pressure propels the motion of liquid, the pressurized gas is a medicinal gas. In some embodiments, liquid motion is induced manually (e.g. a piston pump squeezed by a user's hand like a water pistol).

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure relates to systems and methods for delivery of NO contained within a liquid carrier instead of a gaseous carrier. This approach provides NO purity, dose control, and NO conservation as will be described herein.

Two primary methods are presented:

(1) Dissolving NO-containing gas within a liquid by increasing the gas partial pressure to dissolve gas according to Henry's law.

(2) Introduction of NO-containing gas to a liquid as a nanobubble. Nanobubble loading is supplemental to partial pressure effects and can increase NO content within a liquid several fold.

Nanobubbles are defined as bubbles with a diameter of <500 nm. These bubbles are small enough to enter and interact with the internal components of living cells. In some embodiments, the nanobubbles have a diameter of <200 nm or even <100 nm.

Nanobubbles are different than microbubbles. Nanobubbles can remain stable within a liquid for extended periods of time (e.g., weeks or more). Microbubbles float to the surface of a liquid. Nanobubble size and zeta potential (i.e., the potential difference between the molecules at the surface of the bubble and the liquid medium) are indicators of how stable the nanobubbles will be over time. Microbubbles tend to coalesce and turn into larger bubbles. Nanobubbles are so small that they electrically repel each other. As some nanobubble solutions age, however, their nanobubbles eventually coalesce to create larger bubbles. In other nanobubble solutions, high pressure gas within the nanobubbles escapes to surrounding liquid by dissolving. This dissolving continues until the pressure within the nanobubble has been exhausted at which time gas content within the liquid will be solely determined by gas conditions (i.e. pressure, temperature, gas mixture type) above the meniscus of the liquid.

A typical human cell has a diameter of around 100 microns. At a size of <200 nm, a nanobubble is small enough to enter living cells through the cell membrane and interact with a cell's organelles (i.e., the internal cellular components).

There are two primary types of nanobubbles: shelled and non-shelled. In some embodiments, shelled nanobubbles are formed by placing shell material (e.g., amphiphilic lipids, phospholipids, etc.) to a liquid (e.g. water) into a container. The headspace of the container is filled with a medicinal gas and the container is sealed. The container is then mechanically vibrated (e.g. using a vibratory mixer) to slosh the contents inside, forming shelled nanobubbles within the liquid. The container can then be opened and the liquid mixture poured through a filter (e.g., 1000 nm or 220 nm) to yield a liquid solution with shelled nanobubbles. In other embodiments, mechanical agitation is induced via ultrasound and/or acoustic waves.

Non-shelled nanobubbles are formed by various means. In some embodiments, nanobubbles are formed by cavitation in a liquid (e.g., pressure changes, ultrasound, photon induced, vortex induced). In some embodiments, a membrane is utilized to generate nanobubbles. In some embodiments, gas is introduced to a liquid through nano-sized pores that create nanobubbles. In some embodiments, gas is introduced as a steady steam and motion of the liquid shears the gas stream into nanobubbles. In some embodiments, gas is introduced to a liquid through a venturi.

Nitric oxide can be utilized to make nanobubbles within a liquid. The liquid can be aqueous, lipid (e.g., oil, such as mineral oil), alcohol or other chemistry. Examples of oils include sesame oil, silicone oil, and mineral oil. Alcohol (e.g., ethanol, isopropyl alcohol) can be used in some applications because it can evaporate, rather than accumulate. Other liquids that are suitable for nanobubble solutions include, heparin, saline, heparinized saline, lactated Ringer's solution, phosphate-buffered saline, and biological fluids (e.g., plasma). In some embodiments, the liquid of a nanobubble solution consists of a liquid drug such as cough syrup, enema solution, throat spray, contrast solution (MRI, Ultrasound, X-Ray (e.g. iodinated compounds), antibiotic solution.

Nitric oxide gas within the nanobubbles can be 100% pure or diluted with an inert gas (e.g., nitrogen, helium, argon, carbon dioxide). It should be understood that nanobubbles can be made from other gases (e.g., carbon monoxide, carbon dioxide, ozone, oxygen, helium, nitrogen, nitrous oxide, and xenon), depending on the desired physiological effect. Non-soluble anesthetic gases can also be utilized to form nanobubbles in a solution.

Various general techniques can be employed to form nanobubbles. FIG. 1A depicts an exemplary nanobubble generation method whereby gas is flowed through a porous material 10 to form columns of gas. A flow of fluid shears off the columns of gas into bubbles. In some embodiments, the porous material is a cube (shown). In some embodiments, the porous material is a planar material (e.g., a membrane) (not shown). In some embodiments, the porous material is in the shape of a tube or cylinder (not shown).

Figure 1B:
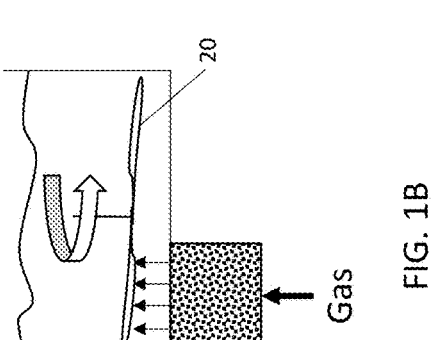
FIG. 1B depicts a method of nanobubble generation that utilizes a nanoporous material and stirred liquid.

FIG. 1B depicts an exemplary nanobubble generation method in which one or more columns of gas flow are introduced to a fluid vessel. A stirring mechanism 20 creates circular flow in the liquid that shears off the gas columns into bubbles.

FIG. 1C depicts an exemplary nanobubble generation method that utilizes a venturi 30. Liquid flows through a conduit. The diameter of the conduit narrows, increasing the liquid velocity. The fast-flowing liquid velocity induces a low pressure at the wall of the conduit. Gas is drawn in through one or more orifices in the wall of the venturi and is sheared into nanobubbles.

Figure 1E:
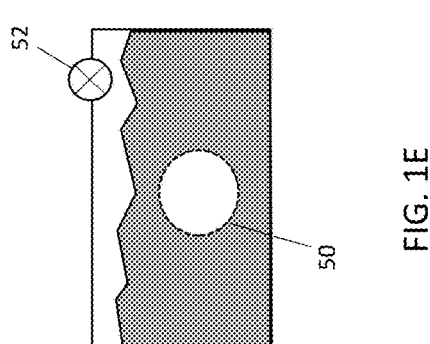
FIG. 1E depicts a method of nanobubble generation that utilizes a leaky pressurized chamber.
Figure 1A:
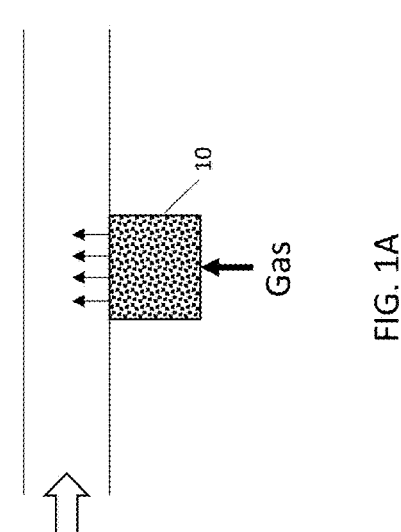
FIG. 1A depicts a method of nanobubble generation that utilizes a nanoporous material and liquid flow.
Figure 1D:
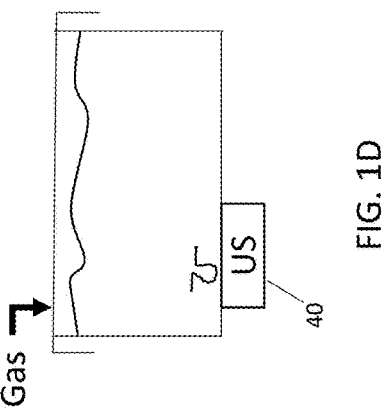
FIG. 1D depicts a method of nanobubble generation that utilizes ultrasonic cavitation.

FIG. 1D depicts an exemplary nanobubble generation method that utilizes ultrasound. The headspace of a liquid reservoir is filled with a specific gas. The gas dissolves into the liquid. In some embodiments, the dissolved content of gas is increased by one or more of increasing the gas pressure, increasing the gas concentration, and lowering the temperature of the liquid. An ultrasonic actuator 40 in contact with the liquid induces cavitation in the liquid. The cavities within the liquid fill with dissolved gas to form nanobubbles.

FIG. 1E depicts an exemplary nanobubble generation method that involves a pressurized vessel. The vessel is partially filled with a liquid. A reservoir 50 (e.g. sphere) with one or more tiny holes is placed within the vessel along with pressurized gas in the headspace. The vessel is sealed until the time of use. Pressurized gas and liquid enter the reservoir to balance the high pressure inside and outside of the reservoir. Prior to use, a valve 52 in the vessel wall is opened expose the contents to a lower pressure (typically atmospheric pressure). Gas within the headspace immediately escapes the vessel. Gas within the sphere escapes the sphere through the tiny holes, making nanobubbles within the liquid. In some embodiments, the gas reservoir is made from a hydrophobic material.

In some embodiments, nanobubble generation is accomplished via a combination of approaches.

Nanobubble Systems

Various system architectures can be used to generate and/or deliver nanobubbles to a patient to treat a variety of medical conditions. In some embodiments, as shown in FIG. 2A, a nanobubble system 60 can include a liquid that can be sourced from a reservoir 62. A nanobubble generator 64 is configured to receive the liquid from the reservoir 62 as well as a gas from a gas source 66 such that the nanobubble generator 64 forms a plurality of nanobubbles from the gas in the liquid. Any excess gas is released from the nanobubble generator 64 through an outlet 68, such as a valve or other opening in the nanobubble generator. The nanobubbles are delivered to a patient through tubing, a cannula, catheter, or other delivery device.

Figure 2B:
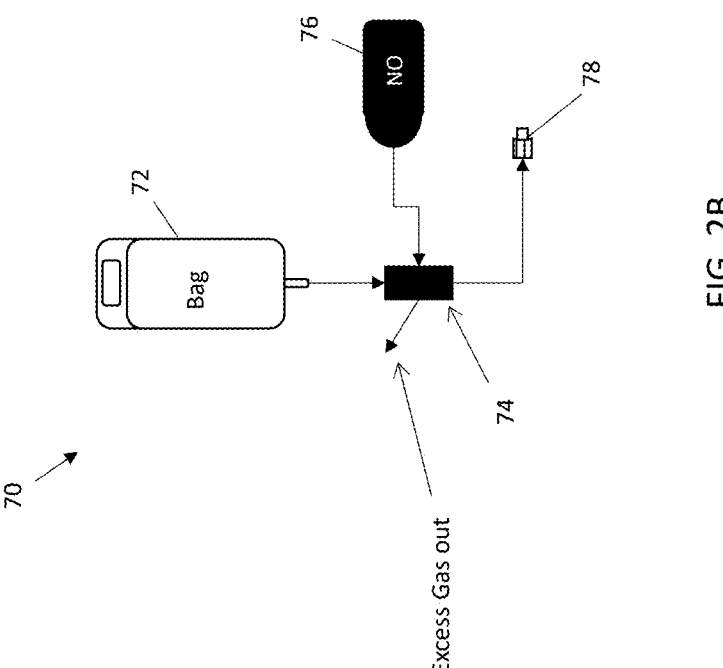
FIG. 2B depicts an embodiment of a nanobubble generation system.
Figure 2A:
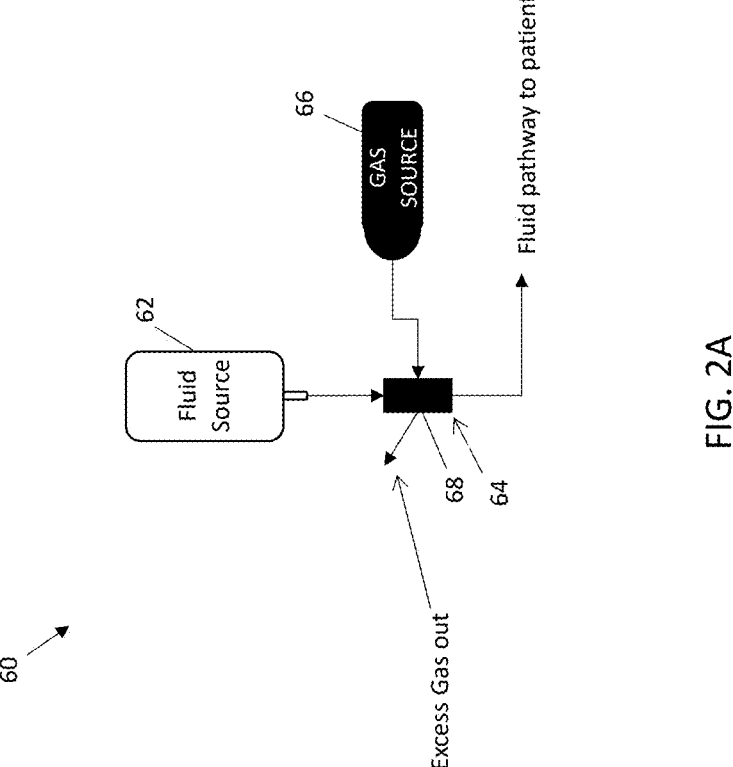
FIG. 2A depicts an embodiment of a nanobubble generation system.

FIG. 2B depicts an exemplary embodiment of a bedside NO nanobubble generation system 70. Liquid is sourced from a reservoir 72 (e.g., a bag, such as an IV bag) and passes into a nanobubble generator 74. NO gas from an NO source 76 enters the nanobubble generator 74 as well. Excess gas (i.e. gas that is not formed into nanobubbles) is released to the environment or to house vacuum. Liquid containing nanobubbles exits out of the nanobubble generator 74 and flows to an exit point. In the depicted example, the exit point is in the form of a connector 78, such as a Luer fitting that connects to a catheter. In some embodiments, a system like this provides nanobubble solution for intravascular delivery. In some embodiments, various levels of pressure and flow control for the liquid and gas (not shown) are applied to balance the delivery of solution constituents and/or target a particular solution flow rate and gas concentration within the liquid.

Figure 3:
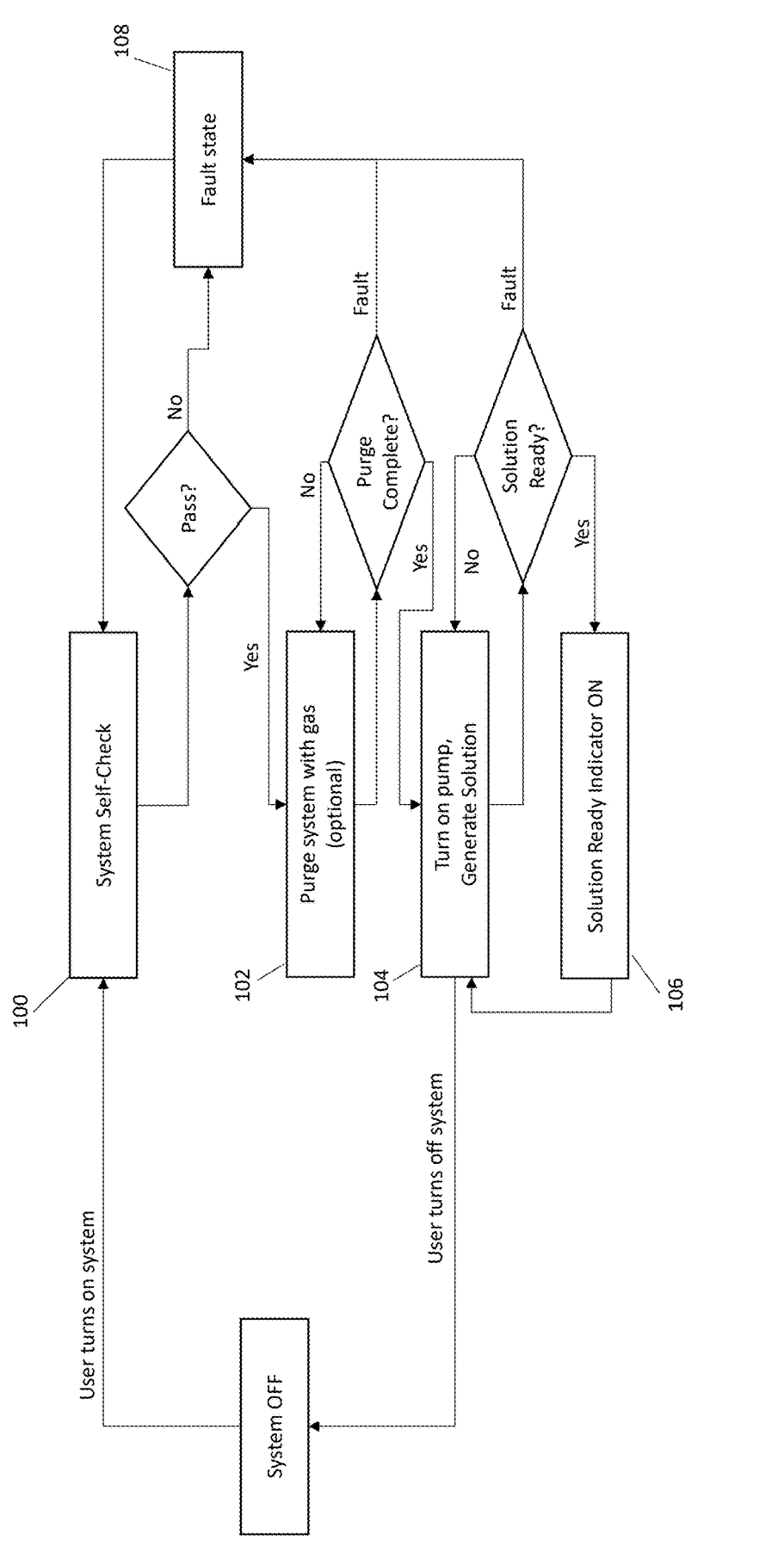
FIG. 3 depicts a control scheme for operating a nanobubble generation system.

As explained above, any of the systems described herein can include a controller to control the generation of the nanobubbles, microbubbles, or any other type of gas-infused liquid solution. FIG. 3 depicts a flowchart showing exemplary steps managed by a nanobubble generation controller to generate a nanobubble solution. The device is initially turned on by a user. In some embodiments, a nanobubble generation system initiates generation after a safety check (step 100). A safety check includes various steps that confirm that the system is ready for use and that the disposable components (if any) have been installed correctly. Exemplary safety check steps include checking that the pumps operate (e.g. monitoring a rotary potentiometer, reading a shaft encoder, on the motor shaft or checking for pressure or flow), checking for leaks in the system (e.g. seeing if the fluid reservoir volume changes over time), checking that sensors are delivering expected values, checking that liquid is in the reservoir (e.g. mass of reservoir, or fluid level indicator), checking that tubing is installed correctly (e.g. detecting in a pump head, detecting in a pinch valve, detecting in pump head, detecting with optical interference), checking that disposable components have not been used before (sterility risk), and gas pressure present and in range. If the safety checks pass, the controller can optionally purge gas from the system (step 102). Once the purge is complete, the controller can turn on the pump to generate the nanobubble solution (step 104). When the controller determines that the solution is ready, the controller can be configured to indicate to a user that the solution has been prepared (step 106). Various conditions detected by the controller can cause the system to enter a fault state (step 108).

Figure 4:
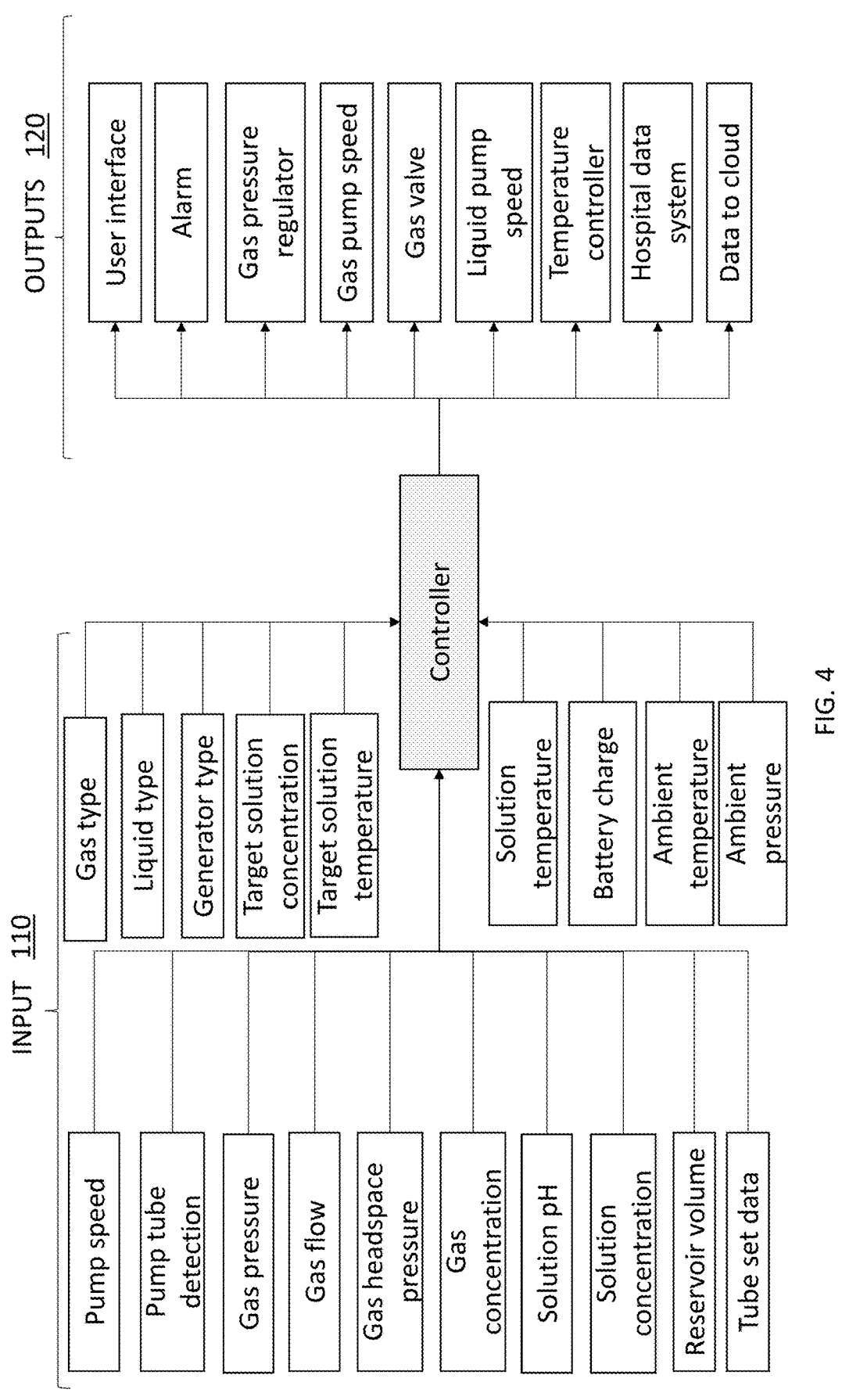
FIG. 4 depicts exemplary inputs and outputs for a nanobubble generation system controller.

FIG. 4 depicts exemplary inputs and outputs of a nanobubble generation system controller. Inputs 110 include one or more of information about system components (e.g. pump speed, pump tube detection/insertion), information about the gas (e.g. gas type, gas flow rate, gas headspace pressure, gas supply pressure, gas concentration), solution concentration (e.g. target value, current value), information about the liquid (e.g. liquid type, a liquid volume measurement, a liquid mass measurement), tube set data (e.g. volume, expiration data, venturi size, etc.), system configuration information (e.g. generator type), battery charge level, and ambient conditions that could affect solution longevity (e.g. pressure, temperature). It will be understood that any data relating to the system, gas, liquid, and/or delivery device can be input into the controller. The controller generates outputs 120 that report system status to a user, generate alarms, modulate solution generation (e.g. gas pressure, gas flow rate, liquid flow rate, temperature), and report information (e.g. to a hospital data center, or to the internet cloud). Exemplary data to be reported to a hospital to the cloud include solution concentration, quantity generated, quantity administered, solution type, timing of delivery, duration of run time, system fault conditions, calibration status and other data. It will be understood that the controller can generate any output related to the system, gas, liquid, delivery device, nanobubbles, mircobubbles, or other bubble types as needed.

In some embodiments, the controller of a nanobubble generation system utilizes a measurement of gas concentration in the solution as an input to a closed-loop control algorithm (e.g. PID controller). The controller modulates system operation (e.g. flow rates, pressure, temperature) of the liquid, gas and/or solution to achieve a target gas concentration within the solution.

Some embodiments of a liquid solution (e.g. nanobubble solution) generation system include an alarm system for notifying a user of an alarm condition. In some embodiments, an alarm is communicated visually through a graphical user interface (GUI) or illuminated indicators. In some embodiments, an alarm is communicated audibly by one or more of a speaker, buzzer, or bell. In some embodiments, an alarm is communicated tactilely, such as by turning an unbalanced motor.

Various alarm conditions can be identified and generated by a liquid solution generation system. FIG. 5 provides some exemplary fault conditions that can be generated by a controller during set-up, self-check, idle, priming, and solution generation.

A nanobubble generation system can include a memory device on disposable components (e.g. liquid reservoir, tubing set) that contains information about the component including but not limited to part number, version number, manufacture date, expiration date, and used/not used indicator.

After successful completion of system self-test, the nanobubble generation system purges the gas tubing and/or liquid reservoir headspace with gas. This step flushes oxygen from the tubing to decrease the potential for $NO_2$ formation and solution acidity. In some embodiments, the purge step flows gas for a specific amount of time. In some embodiments, the amount of time is related to a specific tube set type, and or reservoir type. In some embodiments, the system monitors a gas sensor in the system (e.g. in the exhaust path) for either oxygen or a constituent of the medicinal gas (e.g. NO, $NO_2$) and continues purging until measured gas levels satisfy acceptance criteria (e.g. $O_2$ concentration <a threshold, medicinal gas concentration >a threshold). If a fault occurs during system purging, the system enters a fault state.

After successful completion of purge of the system, the system is ready to begin nanobubble solution generation. In some embodiments, the controller initiates the liquid pump automatically. In some embodiments, the system waits for user input to begin generation. The liquid pump circulates liquid around the loop and through the nanobubble generator to generate a nanobubble solution. The system monitors for fault conditions which would send the system into a fault state in all states, not just those depicted. In some embodiments, the system indicates that the solution is ready for use after a particular amount of time. The amount of time may vary with the liquid, gas(es) and thickeners being used. In some embodiments, the system measures the concentration of the gas(es) in the solution with a sensor to know when nanobubble generation has reached a target level. In some embodiments, the target level is a maximal amount possible for the given liquid, gas, gas concentration, temperature, and pressure. In some embodiments, the target level is based on the minimum concentration required for clinical efficacy, as indicated by an appropriate sensor. For example, a nanobubble solution is being used for a clinical application that requires a minimum concentration of the gas >1 uM. When the concentration of nanobubbles is >1 uM, the system indicates to the user visually, audibly or by tactile means that the solution is ready for use. In other embodiments, the quantity of nanobubbles in solution is quantified by an impedance measurement of the solution. In other embodiments, the presence of nanobubbles in solution is determined based on a pH measurement of the solution. As the nanobubble generation system continues to operate, the nanobubble concentration may increase further, still satisfying the minimum nanobubble concentration requirement. The system stops nanobubble generation in the presence of a fault or when requested by a user.

In some embodiments, pump operation is intermittent after the system reaches a target NO nanobubble concentration. Stopping the pump saves energy and reduces noise generation. The frequency of pump operation required to maintain a satisfactory nanobubble concentration depends on the lifespan of the specific nanobubble solution. For example, a NO in saline solution may require the pump running for 1 to minutes at a 50% duty cycle to maintain a satisfactory NO nanobubble concentration. The duty cycle could be less for nanobubble solutions that are more stable over time.

Figure 6:
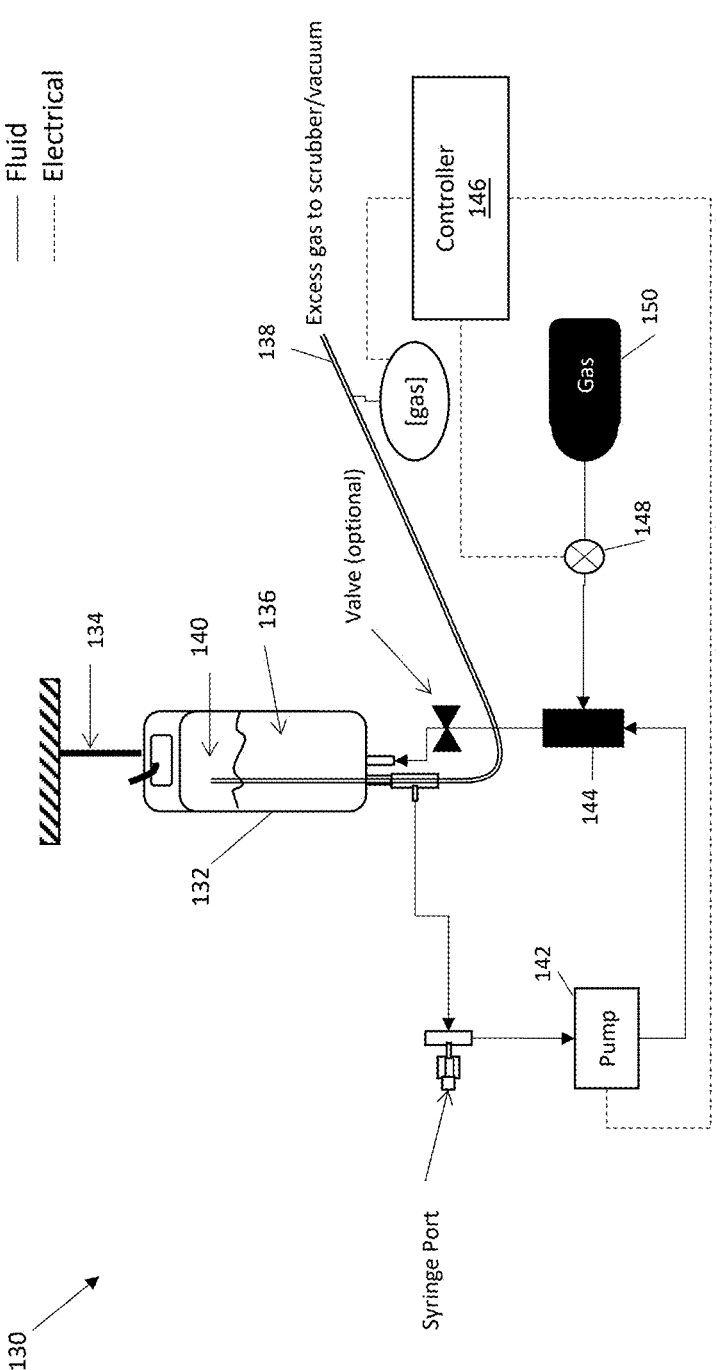
FIG. 6 depicts an embodiment of a nanobubble generation system with recirculation.

FIG. 6 depicts another exemplary embodiment of a NO nanobubble generation system 130. A reservoir 132 of liquid can be attached to a hook 134. In some embodiments, as shown, the reservoir 132 is a bag, such as an IV bag, which provides a supply of sterile liquid 136. The reservoir can have an inlet port and an outlet port. For example, the two spike ports of a standard IV bags can be utilized as inlet and outlet flow ports. One of the spike connections can include a tube 138 that extends from the bottom of the bag up to the gas headspace 140 in the top of the bag. Liquid exits the bag out the left spike through the annular space between the tube and the spike. As gas pressure builds in the headspace 140 of the bag, it exits the system through the tube 138. In some embodiments, excess gas passes through a scrubber prior to release into the atmosphere. In some embodiments, excess gas is collected by a house vacuum system.

Liquid exiting the system flows to a fitting that includes a drainage port (e.g. syringe-activated Luer fitting). This fitting enables a user to withdraw a portion of the circulating liquid. Below the drainage port is a pump 142 that circulates solution from the reservoir 132 through the nanobubble generator 144 and back to the reservoir in a recirculation fashion. Liquid exiting the pump travels to the nanobubble generator. In some embodiments (shown), gas is introduced to the system at the nanobubble generator (e.g. a Venturi design). In some embodiments, gas is introduced to the liquid before it enters the nanobubble generator (e.g. cavitation designs). Exiting out the top of the nanobubble generator is a combination of liquid with nanobubbles and microbubbles as well as gas. In the reservoir, microbubbles float to the surface and gas collects in the headspace, where it is extracted by the tube. In some embodiments (not shown), a pump actively withdraws excess gas from the headspace. A recirculation architecture allows for the liquid to pass through the nanobubble generator multiple times to achieve a high concentration of nanobubbles in solution.

In this design, the reservoir and tubing set can be disposable. The tubing set can be provided to a user sterile so that when it is connected to sterile the contents of an IV bag, the solution to be made is sterile. Sterilization can be done by any means, including EtO, steam and radiation. Liquid is drawn from the bottom of the reservoir, where there will be the fewest microbubbles (because the float).

In practice, a system such as this can be set up quickly by hanging an IV bag and spiking the liquid reservoir bag with a new tubing set. In some embodiments, the tubing set is in the form of a cassette or backer card to assist in locating and/or inserting tubing into a pump, valves, sensors, or other system components.

In some embodiments, the system is purged of oxygen before use. In some embodiments, a controller 146 opens the gas flow control valve 148 to permit gas to flow from a gas source 150 through the system without turning on the liquid pump. In some embodiments, pump tubing is not inserted into the pump head until after purging to ensure that gas is removed from the entire loop of tubing. In some embodiments, valve on the return leg of the liquid flow path is closed to ensure the tube set is purged in the pump tubing as well. In some embodiments, the return leg valve is a pinch valve that enables the flow within the tube to arrest without contacting the liquid to maintain sterility within the tubing set. The system shown in FIG. 6 includes an optional oxygen sensor in the exhaust flow path. The oxygen sensor can be utilized to monitor oxygen content in the exhaust as the system is purged of oxygen.

Figure 7:
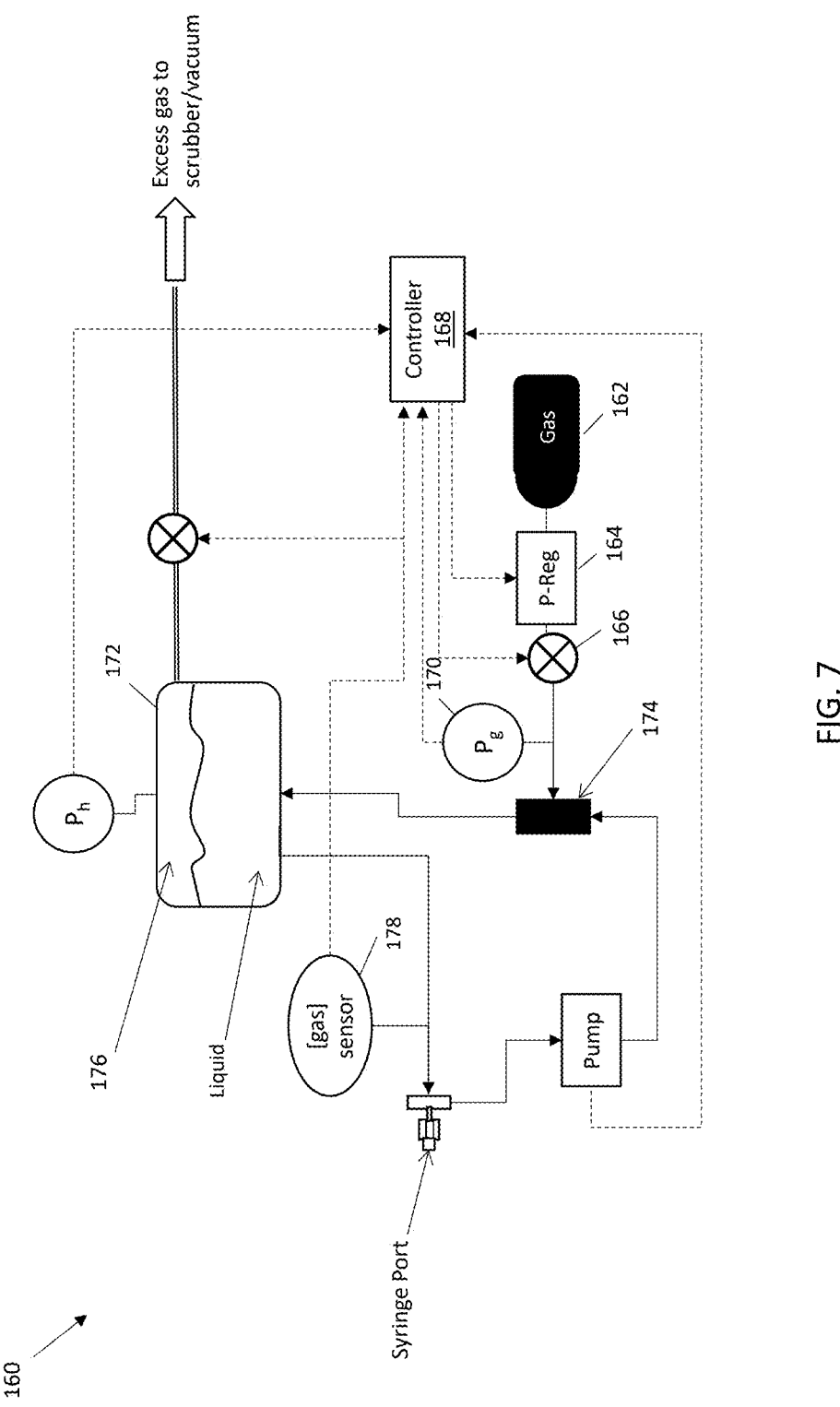
FIG. 7 depicts an embodiment of a nanobubble generation system.

FIG. 7 depicts an exemplary nanobubble solution generation system 160 with a controller. Solid lines depict gas/liquid flow and dashed lines depict electrical connections. As shown, gas is sourced from a compressed gas reservoir 162. The pressure is reduced through an adjustable pressure regulator 164. Flow through the regulator is varied by a valve 166. The controller 168 receives gas pressure values from a pressure sensor 170." In some embodiments, gas flow is controlled by a mass flow controller instead.

The controller 168 also controls a pump that moves liquid through the system. Liquid is sourced from a reservoir 172 and sent through a nanobubble generator 174 where gas is introduced to the liquid. In some embodiments, not all gas forms nanobubbles in the liquid. Microbubbles and macrobubbles float out of the liquid in the reservoir and collect in the reservoir headspace 176. As gas accumulates in the headspace, the pressure within the headspace increases. The controller measures the pressure within the headspace with a sensor labeled "Ph." A valve on the headspace exhaust line is modulated by the controller to maintain headspace pressure at a target level, or within a specific range.

The controller 168 also receives gas concentration within the liquid from a concentration sensor 178. The technology utilized to make the nanobubble concentration measurement include but are not limited to gas concentration measurement, electrical impedance measurement, and dynamic light scattering. In some embodiments, the controller varies one or more of pump speed, inlet gas pressure, inlet gas concentration, inlet gas mass flow rate, liquid temperature, liquid flow rate, and reservoir headspace pressure to maintain a target concentration of gas within the liquid. In one exemplary embodiment, an electrochemical sensor measures the concentration of NO in a NO nanobubble solution. In some embodiments, the solution concentration sensor location is preferred to be located in the flow exiting the liquid reservoir (shown) to ensure that the solution has little to no gaseous content or large bubbles that could affect measurement accuracy.

In general, some embodiments modulate one or more of the duration of nanobubble generation, the gas concentration, gas flow rate, gas pressure, liquid flow rate, gas orifice size, liquid venturi size, headspace pressure, and gas recovery pump (not shown) flow rate to modulate the concentration of gas within the nanobubble solution.

Nanobubble Dose Control

Dose delivery is modulated by varying at least one of the density of nanobubbles within the liquid (i.e., quantity of nanobubbles per unit volume), the nanobubble size, the gas concentration within the nanobubble gas, the rate/volume of liquid delivery, the exposure time to nanobubble solution, the surface area treated, pressure of nanobubble solution acting upon tissues/surfaces, and other factors.

There are various ways of defining the dose of a gas delivered within a liquid medium. In some embodiments, the dose is defined as a mass of gas per unit time (e.g. mg/hr). This approach is useful when a particular number of moles of gas are to be delivered without a sensitivity to gas concentration. In some embodiments, a minimum concentration of gas is required to have a particular physiological effect (e.g., kill an infection). In these applications, the dose can be defined as the duration of time that the gas concentration exceeds a minimum threshold (e.g., 1 minute above 400 ppm).

In some embodiments, a viscous liquid is selected for slower NO release. The liquid material serves as the matrix in a composite material with nanobubbles. In some embodiments, the matrix material is rigid and degrades over time to release nanobubbles of NO. In some embodiments, a tablet of biodegradable/bioresorbable material is loaded with NO nanobubbles and implanted to release NO over time as it degrades. In some embodiments, the tablet is in the form of a cough drop that releases NO to treat a mouth and throat infection as the cough drop erodes. In some embodiments, a thick, gel-like liquid is loaded with nanobubbles to treat a laceration, incision, puncture, burn, skin graft, chronic wound or open wound. In other embodiments, a nanobubble solution is first made in a non-viscous liquid and which is subsequently thickened with one or more thickening agents. For example, a gel can be formulated by mixing a nanobubble/water solution with one or more thickeners (e.g. agar, starch, etc.). NO nanobubbles on the surface of a wound have anti-infection (i.e. kill pathogens), angiogenic and vasodilatory effects. The increased blood flow owing to vasodilatory effects can increase uptake of other drugs in the solution (e.g., antibiotics) into the affected tissue.

Additional examples of thickeners for a nanobubble solution include one or more of guar gum, glycerin, sugar, starch (e.g. potato, corn, etc.), aloe, dextran, dextrin, maltodextrin, 5-10% dextrose solution, povidone (dissolves in water and oil), agar, pregel (modified starch), pectin, polylactic acid (PLA), polylactic-co-glycolic acid (PLGA), polyethylene glycol (PEG), cellulose, gelatin, collagen, chitosan, and alginate. In some applications, it is preferable to utilize a thickener that is metabolized by the nanobubble solution recipient. The degree of thickening of a nanobubble solution can be controlled by the quantity of thickener added as well as the molecular weight of the thickener (e.g. PLA polymer chain length).

In some embodiments, a thickening agent is added to a nanobubble solution after the solution has been removed from a nanobubble generation system. In some embodiments, a nanobubble delivery device mixes nanobubble solution with a thickening agent prior to delivery of the thickened solution to a patient.

Applications for nitric oxide nanobubbles include treating cancer and infections. NO nanobubble solutions can be delivered in a variety of ways, including but not limited to injection (e.g., into tumors, intramuscular, subcutaneous), sprays/mists (e.g., nasal), irrigation (e.g., cleaning of open wounds), lavaging/douching of cavities (e.g., mouth wash), and prolonged topical protection (e.g., gels for wound coverage). In some embodiments, nanobubble-laden liquid (e.g., water, Ringer's solution, saline, alcohol, mouth wash) is used to lavage a cavity of the body (e.g., peritoneal cavity, plural cavity, intestine, mouth, nasal, arm pit) to disinfect and/or treat tissue. Treatment effects include blood vessel dilation to improve blood flow to an area. This effect is important for delivering and/or improving the therapeutic effect of systemic drugs to a specific region or simply improving the oxygenation to a region. In some embodiments, NO nanobubble solution is included in a liquid or gel for topical application to increase blood flow to the penis to address erectile dysfunction. In some embodiments, the NO nanobubble liquid or gel has lubricative properties as well. In some embodiments, an organ is lavaged with nano-bubble solution to treat for pathogens. In some embodiments, an organ is perfused through the vasculature, or the interstitial spaces of an organ are injected with nano-bubble solution.

In another application, NO nanobubbles are included in liquid for peritoneal dialysis. This approach provides protection against infection and dilates the vasculature in the peritoneal cavity to improve chemical exchange between the dialysate and the blood stream.

In another application, NO nanobubble solution is introduced (topically or injected) to an abscess to treat infection.

In another application, NO nanobubble solution is applied topically to the skin to promote hair growth by inducing vasodilation and improving blood flow to the treated area.

In some embodiments nanobubbles are added to a liquid (e.g., blood, plasma, saline, lactated ringers solution, injected medicine) that is introduced to the circulatory system. In some embodiments, nanobubble liquid is introduced to the lymphatic system. In some embodiments, the lymphatic system is perfused with a nanobubble solution to treat cancer and/or infection.

In some embodiments, NO nanobubbles are delivered in an aerosol. In some embodiments, NO nanobubble solution passes through a jet nebulizer that distributes the solution throughout a gas stream. Vibrating mesh and ultrasonic nebulizers can also deliver aerosols but may result in higher nanobubble loss due to the vibrations. Nanobubble aerosols can be delivered via inspiration or topically. Aerosols typically have a particle diameter of 1 to 25 um. Thus, nanobubbles having a diameter less than 200 nm can fit within aerosol particles. The location of aerosol delivery can be somewhat controlled by aerosol particle size. For example, alveolar delivery requires particles <2 µm while particles in the 2-5 µm size range tend to deposit in the central and small airways.

In some embodiments, NO nanobubble solution is utilized to treat and/or prevent infections of the nasal sinus, larynx, pharynx and throat. NO nanobubble solution is introduced through either the nose or mouth, depending on the location of the infection. In some embodiments, the NO nanobubble solution is delivered by squeezing a squeeze bottle that ejects solution. In some embodiments, NO nanobubble solution is pumped out of a container as a spray. In some embodiments, the NO nanobubble solution is released from a pressurized vessel via an inert propellant gas (e.g., nitrogen, argon, carbon dioxide). In some embodiments, the nanobubble solution is utilized as a flush to irrigate the nasal cavity. Solution can enter one nostril and exit the other nostril (e.g., Neti pot).

Figure 8:
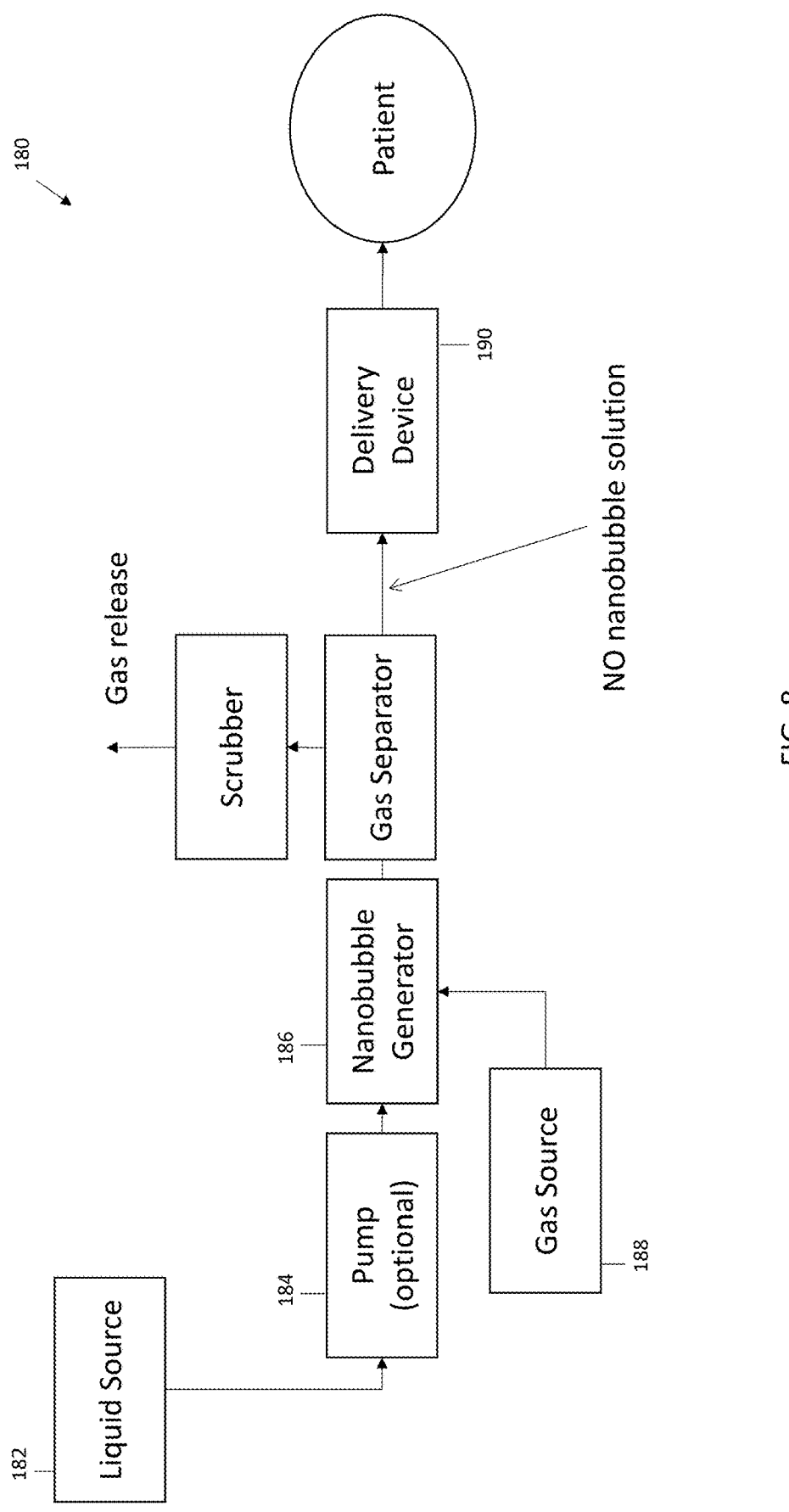
FIG. 8 depicts an embodiment of a NO nanobubble generation and delivery system.

FIG. 8 depicts an exemplary embodiment of a nanobubble generation and delivery system 180. A liquid is sourced from a liquid source 182, passes through an optional pump 184 and enters a nanobubble generator 186. Gas is sourced from a gas source 188. The nanobubble generator 186 creates nanobubbles of gas within the liquid. The gas-loaded liquid is delivered to a patient through a delivery system 190. In some embodiments (not shown), the gas flow and liquid flows are controlled by a software-driven control system. In some embodiments, fluid is sourced from a reservoir and propelled by a pump that is controlled by a control system. In some embodiments, fluid is sourced from a pressurized reservoir through a variable orifice (e.g. valve, mass flow controller, etc.) controlled by a control system. In some embodiments, gas is sourced from a reservoir/cartridge/pressurized cylinder and the gas flow rate is controlled by a mass flow controller, valve or the like via a control system. In some embodiments, the gas is generated on demand and released into the nanobubble generator under the direction of the control system. The control system can vary the pressure and flow rate of the liquid and gaseous inputs into the nanobubble generator. In some embodiments, additional parameters are controlled including one or more of temperature, humidity, duration of exposure of constituents to the nanobubble generator, run time, etc. In some embodiments, the entire device is packaged sterile. In some embodiments, a sterile filter (not shown) at the output of the device can ensure that the nanobubble solution is sterile.

Figure 9:
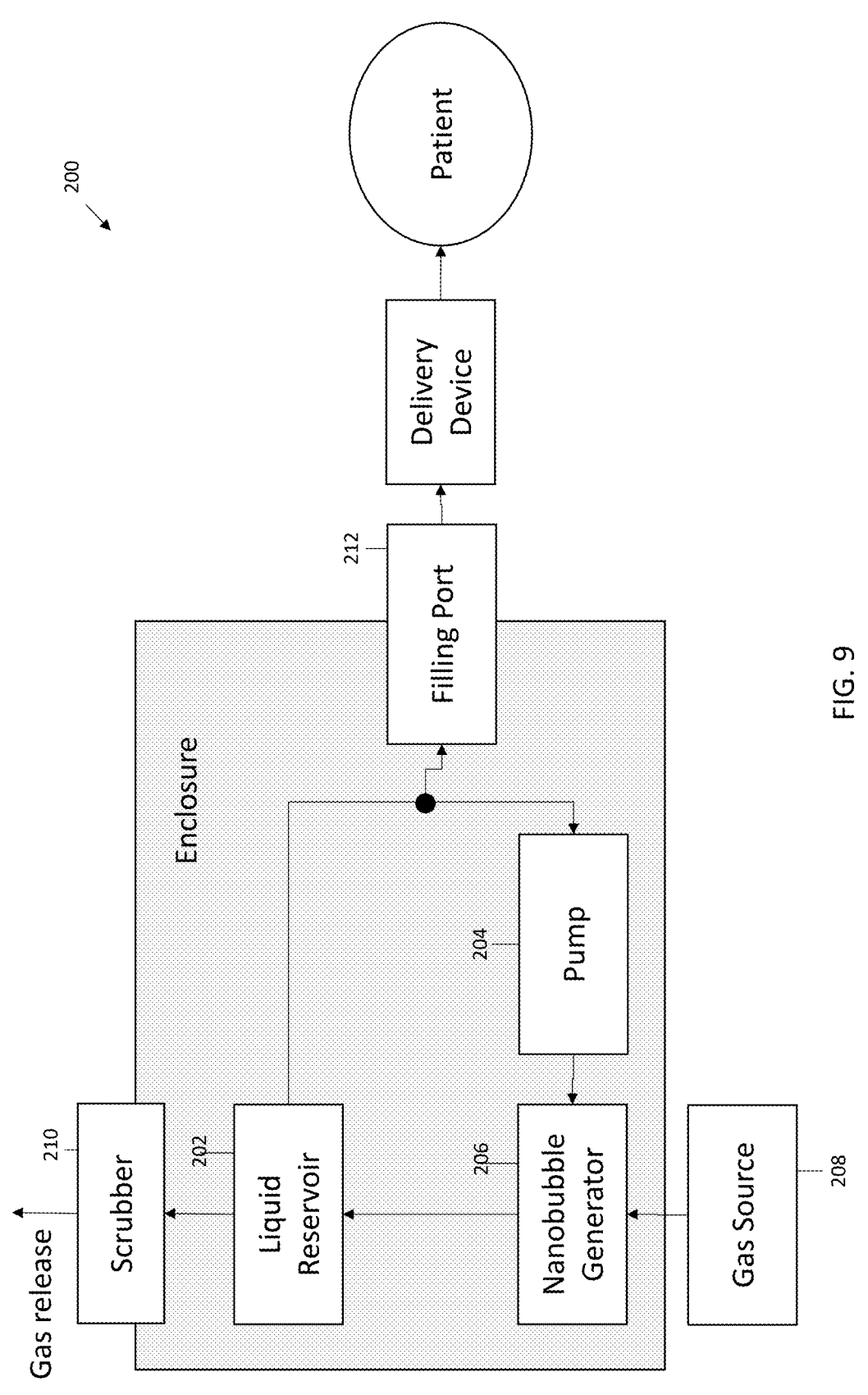
FIG. 9 depicts an embodiment of a NO nanobubble generation and delivery system.

FIG. 9 depicts a nanobubble generation system 200 that utilizes a recirculation loop to continuously generate nanobubble solution. Liquid is sourced from a reservoir 202 and propelled by a pump 204 through a nanobubble generator 206. Gas flows from a gas source 208 through optional pressure regulators and flow control devices (e.g. valves) (not shown) to enter the nanobubble generator 206. A mixture of nanobubble solution and gas returns to the liquid reservoir 202. Within the liquid reservoir, microbubbles and larger bubbles float to the surface of the liquid. Gas collects in the headspace of the reservoir and is released through an optional scrubber 210 from the system.

A filling port 212 (e.g., syringe activated Luer, stop cock, etc.) provides a means to withdraw an amount of nanobubble solution from the system. In some embodiments, the filling port is located within the liquid reservoir (not shown). In some embodiments, the filling port is located in the tubing (shown) or a manifold (not shown). In some embodiments, the entire fluid pathway is sterilized before use. Fluid pathways are typically assembled in a clean environment to minimize bioburden. In some embodiments, the nanobubble solution is filtered prior to delivery to the patient.

Figure 10:
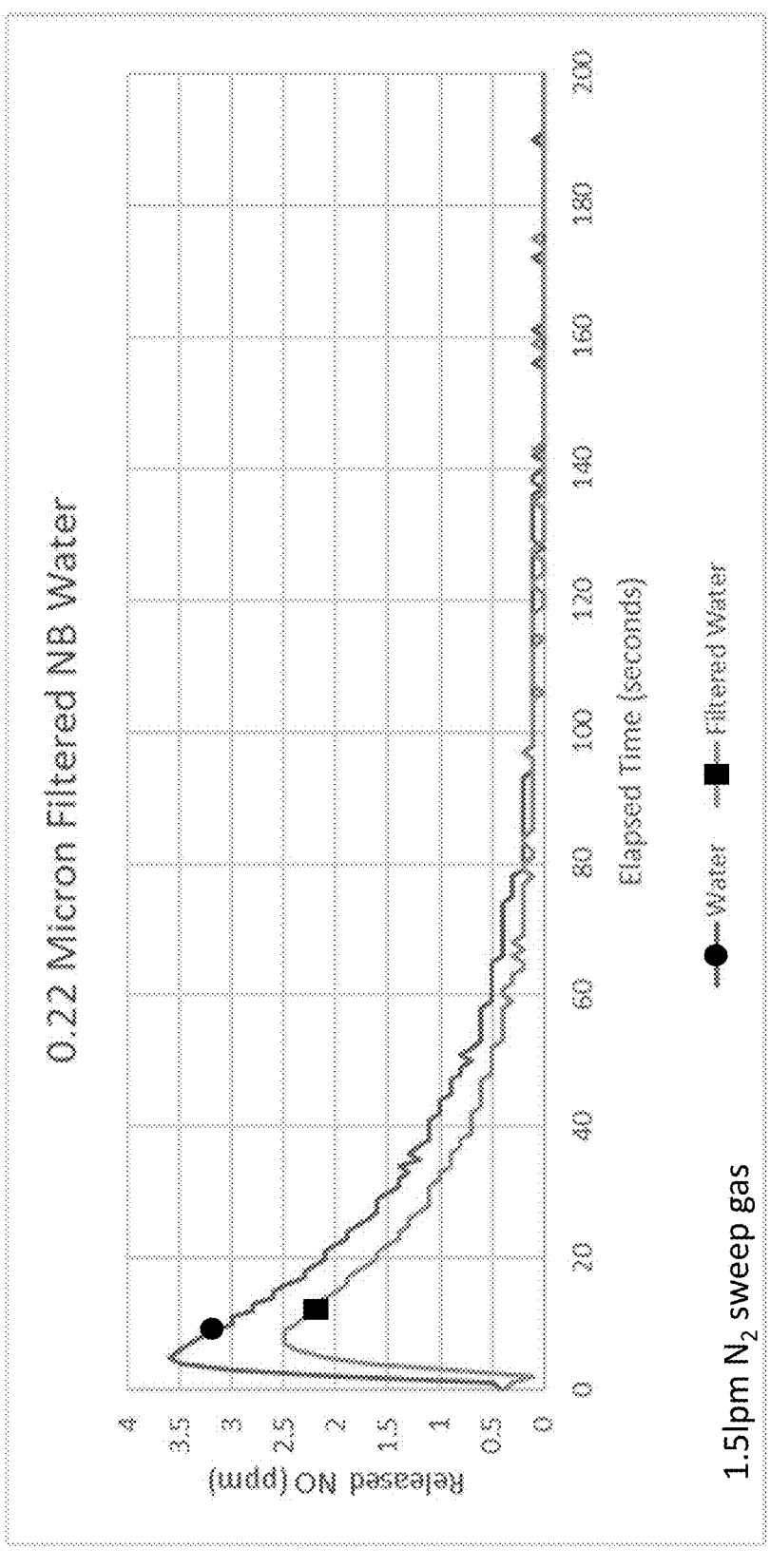
FIG. 10 demonstrates an exemplary embodiment of the retention of NO nanobubbles in solution after sterile filtration.

FIG. 10 depicts an exemplary graph showing the results of an experiment to assess the effect of a sterile filter (0.22 micron) on a NO nanobubble solution. In some embodiments, a sterile filter is part of the nanobubble generation system. In some embodiments, a syringe with sterile filter is utilized to draw nanobubble solution from a nanobubble generation system. In some embodiments, a syringe is loaded with nanobubble solution and then delivered through a sterile filter to a patient (e.g. through a catheter, or topically onto a wound).

Figure 11:
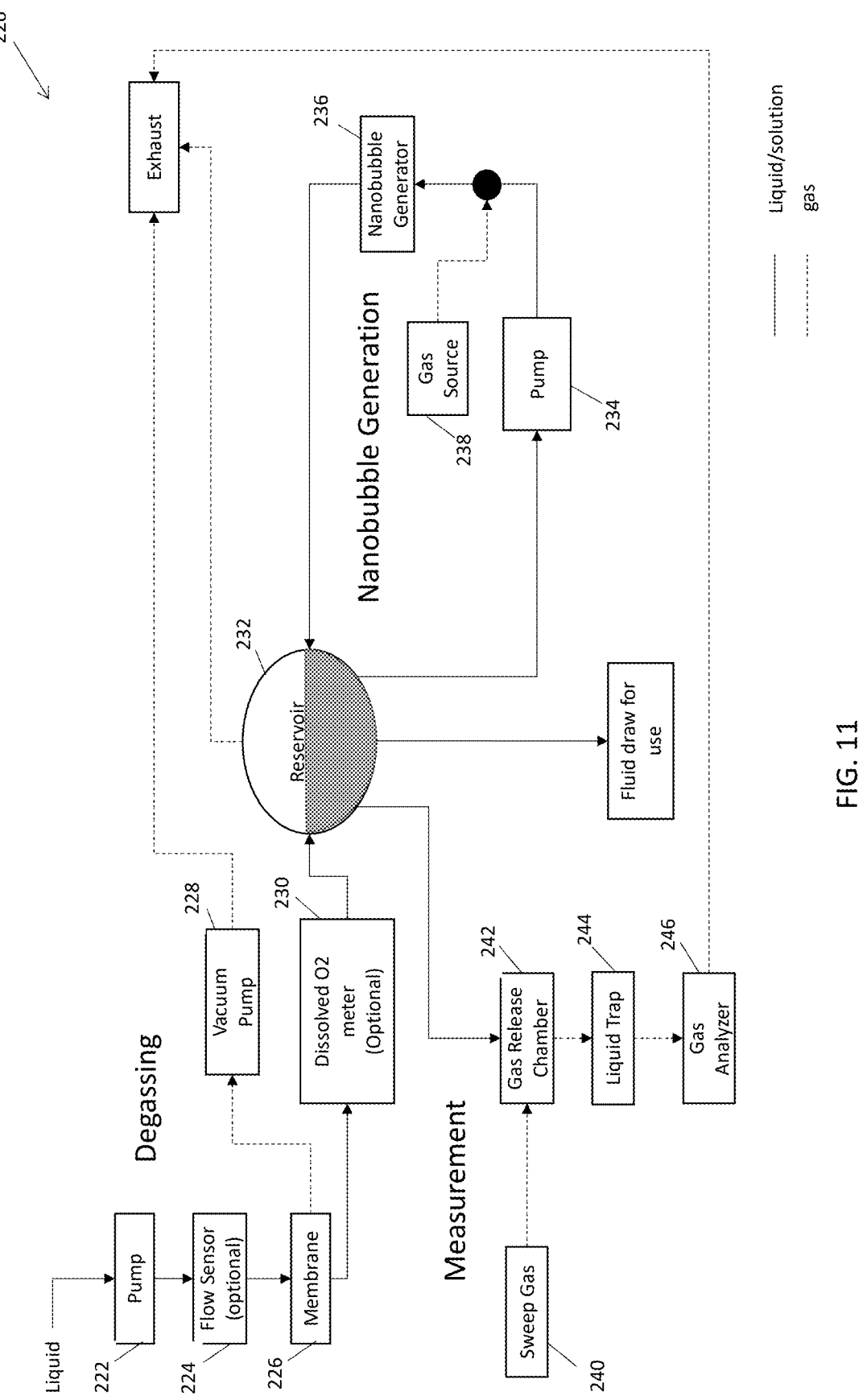
FIG. 11 depicts an embodiment of a system for degassing liquid, generating nanobubbles, measuring nanobubbles and dispensing nanobubble solution.

FIG. 11 depicts an exemplary embodiment of a NO nanobubble generation and measurement system 220. The system is comprised of three primary sections: 1) a degassing subsystem, 2) a nanobubble generation subsystem, and 3) a nanobubble measurement subsystem. Degassing is done to enable more of the target gas to be dissolved in the liquid. Degassing also removes gases that could potentially react with the nanobubble gas (e.g. oxygen reacts with nitric oxide to form nitrogen dioxide, $NO_2$). The degassing process involves a flow of liquid passing through the system. In the embodiment shown, a pump 222 is utilized, however any means of liquid transfer could potentially be used including but not limited to pressurized liquid, gravity feed and other methods. The liquid passes through an optional flow sensor 224 that verifies and quantifies fluid flow. The liquid then passes through a membrane gas exchanger 226. The membrane is permeable to gas but not permeable to liquid. A vacuum 228 is pulled on one side of the membrane, lowering the dissolved gas content within the liquid on the other side of the membrane, promoting gas transfer from the liquid to the vacuum. The vacuum is generated by a vacuum pump. In the case of oxygen removal, an optional dissolved oxygen meter 230 can be used to confirm that the system is operating properly. In some embodiments, pressure swing absorption with molecular sieve material is used to separate nitrogen and oxygen from air. Then, degassed liquid is exposed to the nitrogen so that the only dissolved gas in the liquid is nitrogen. This approach prevents nanobubble gas from coming into contact with oxygen.

In some embodiments, a liquid is degassed of oxygen by adding a material that reacts with dissolved oxygen. In some embodiments, metal particles are added to the liquid. The metal reacts with oxygen to form a metal oxide, thereby pulling oxygen out of solution. In some embodiments, iron particles are utilized for this purpose.

In some embodiments, liquid is degassed by boiling the liquid for a period of time. In other embodiments, liquid by passing the liquid through a chamber under vacuum pressure, containing a gas separating membrane. In other embodiments, liquid is degassed by freezing and thawing the liquid while exposing the liquid to a vacuum. In other embodiments, liquid is degassed by sonicating the liquid while exposing the liquid to a vacuum.

Degassed liquid (e.g. water, saline, alcohol) is introduced to a reservoir 232. In some embodiments, the reservoir is flushed with a sweep gas to control the potential reactions within the reservoir headspace. In some embodiments, for example, the reservoir is purged with an inert gas (e.g. nitrogen) prior to introduction of deoxygenated liquid. In some embodiments (not shown), the reservoir is continuously swept with an inert gas to prevent atmospheric gases from entering the reservoir during nanobubble production. Liquid within the reservoir is drawn from the reservoir via a pump 234 and sent through a nanobubble generator 236. A gas stream from a gas source 238 for producing nanobubbles is introduced to the fluid path either before (shown) or at (not shown) the nanobubble generator. Within the nanobubble generator, the liquid is manipulated (e.g., sheared, cavitated, etc.) in ways that form nanobubbles. The process is typically not 100% efficient resulting in some microbubbles and excess gas exiting the nanobubble generator. Microbubbles float to the surface and into the head space within the reservoir. Excess gas exits the headspace through the vent pathway. In some embodiments, flow within the vent pathway is actively managed with a pump. In some embodiments, pressure within the reservoir headspace drives excess gas from the headspace into the exhaust flow.

Nanobubbles accumulate within the solution over time with each additional lap, as the liquid passes through the pump, nanobubble generator and back to the reservoir. A steady state nanobubble concentration is eventually reached after multiple passes through the system. This process can take several minutes, depending on the volume of fluid involved, the flow rate and the efficiency of the nanobubble generator. The quantity of nanobubbles in solution can be controlled by one or more of flow rate of liquid and gas through the generator, the level of degassing performed on the liquid, the amount of time the nanobubble generator is run, the temperature of the liquid and other aspects.

A liquid sample can be removed from the reservoir (e.g., using a pump, gravity feed, syringe) for measurement. In some embodiments, the quantity of gas in nanobubble form and dissolved can be quantified in a sample of the solution as follows. A sample of the solution is added to a chamber. An inert sweep gas 240 flow passes through the headspace of the chamber 242, through a liquid trap 244 and on to a gas analyzer 246. The sweep gas flow rate is selected to exceed the required sample flow rate of the gas analyzer to ensure accurate analyzer operation. In some embodiments, one or more of ultrasonic energy and heat are applied to the nanobubble solution to drive the nanobubble gas out of the liquid and into the sweep gas. In some embodiments, the sweep gas is introduced to the chamber below the surface level of the nanobubble solution so that it bubbles up through the solution, providing agitation of the liquid. In some embodiments, a porous bubble generator like a fish tank oxygenator is utilized to produce finer sweep gas bubbles for greater agitation of the nanobubble solution and more rapid nanobubble gas release. Loaded sweep gas exiting the gas analyzer can be routed to an exhaust system or released to atmosphere (not shown), depending on the type of gas and environment.

Figure 12:
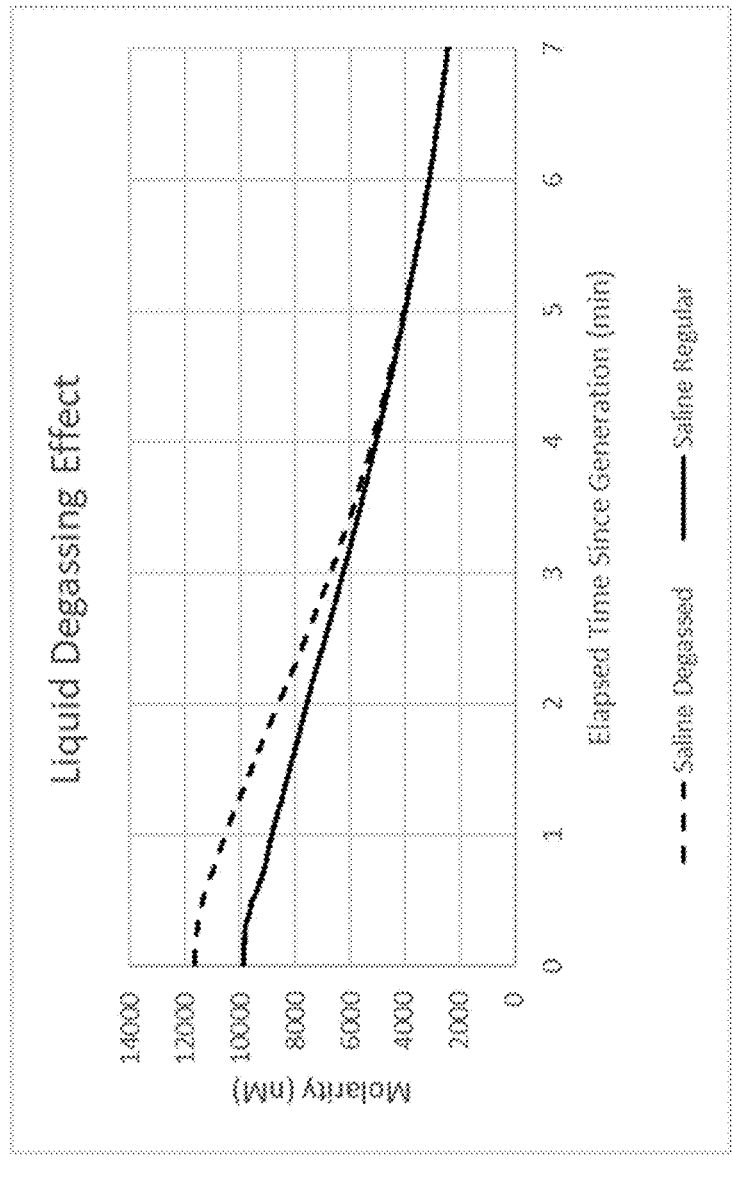
FIG. 12 presents experimental data that demonstrate the effect of degassing on solution pH and NO concentration.

FIG. 12 depicts an exemplary graph showing the effects of liquid degassing on a NO nanobubble solution. Two solutions were generated by introducing 20,000 ppm NO to saline. The initial pH for the saline was 6.8. After nanobubble generation, the pH of the degassed saline was 4.0, while the pH of the normal saline was 3.6. The higher pH of the degassed saline was due to there being less oxygen in the saline to react with the NO and form nitric acid. FIG. 12 shows a that the initial concentration of the degassed solution was roughly 20% higher than the non-degassed solution. The concentration of the degassed solution remains higher for several minutes in air. The concentration could remain higher for longer in a no-oxygen environment. Hence, higher concentrations of NO are achieved for longer periods of time in water when the liquid is degassed. This is because degassing results in less oxygen within the water that can react to form $NO_2$. Since $NO_2$ is water soluble, forming nitric acid in solution, degassing also results in more neutral pH solution (i.e. less acidic).

Figure 13A:
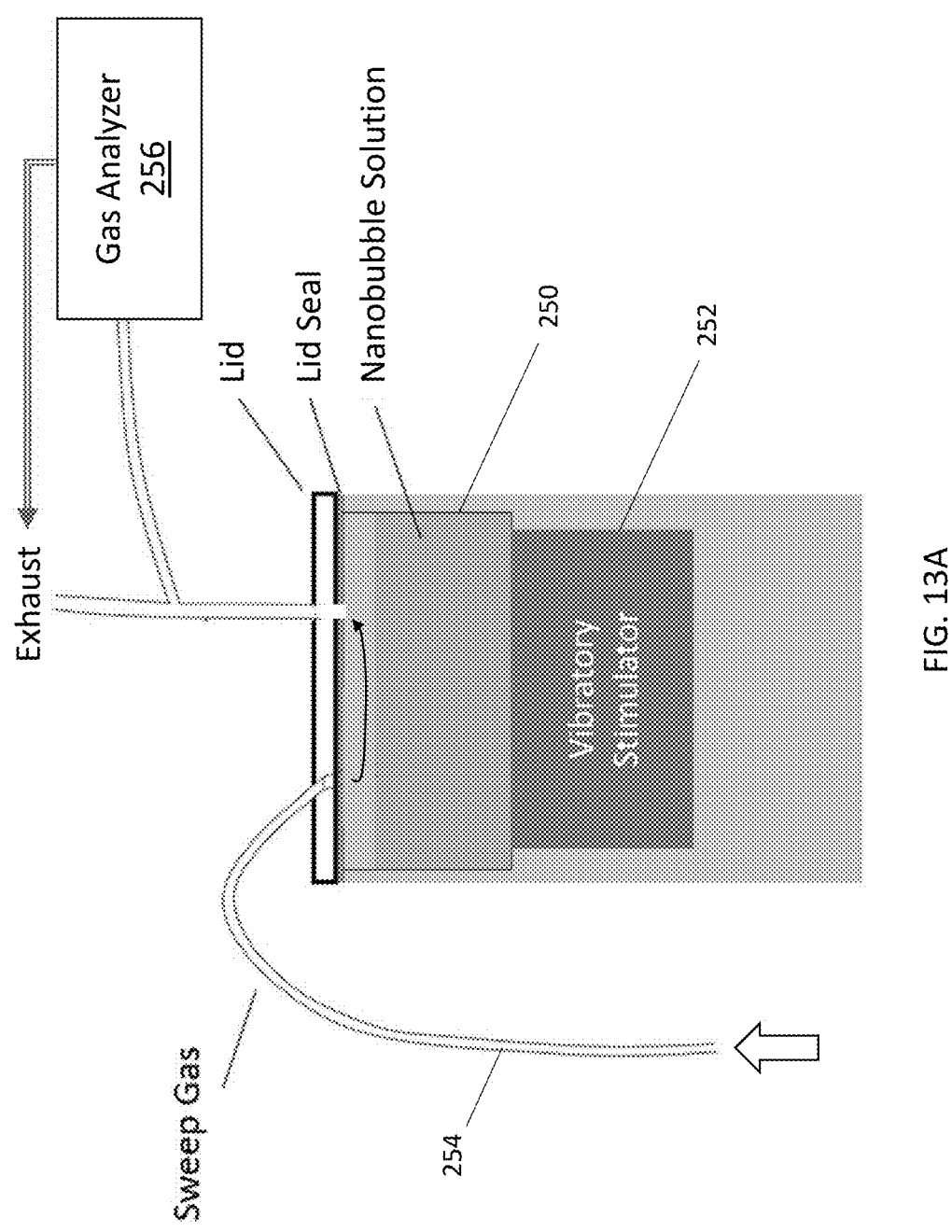
FIG. 13A depicts an exemplary method of measuring the gas content within a liquid using a vibratory stimulator.

FIG. 13A depicts an exemplary system showing a method to release nanobubbles from a nanobubble solution. It will be noted that this procedure can be performed after larger bubbles (e.g., microbubbles) have come out of solution as they will affect measurement results. Nanobubble solution is placed a basin 250 connected to a vibratory stimulator 252. Vibrations and/or heating of the liquid stimulates the release of nanobubble gas from the liquid. The gas rises out of the liquid and is carried away by a sweep gas flow. A sweep gas flow tube 254 is connected to a sweep gas source. The sweep gas is introduced to the vibration chamber at a known flow rate (e.g., controlled by a mass flow controller, or measured by a flow sensor). In some embodiments, the sweep gas is introduced to the head space above the liquid sample (shown). In some embodiments, the sweep gas is introduced below the surface of the fluid sample (not shown). In some embodiments, the sweep gas is introduced through a bubbler below the surface of the liquid to increase gas/liquid interaction (not shown). Sweep gas collects gas from burst nanobubbles and flows out of the headspace towards exhaust. A gas analyzer 256 draws a sample from the sweep gas flow to measure the concentration of the nanobubble gas in the sweep flow. In some embodiments, nitrogen is utilized as a sweep gas to collect nitric oxide released from the liquid. In some embodiments, the vibrations imparted on the fluid are in the ultrasound range (>20 kHz).

Figure 13B:
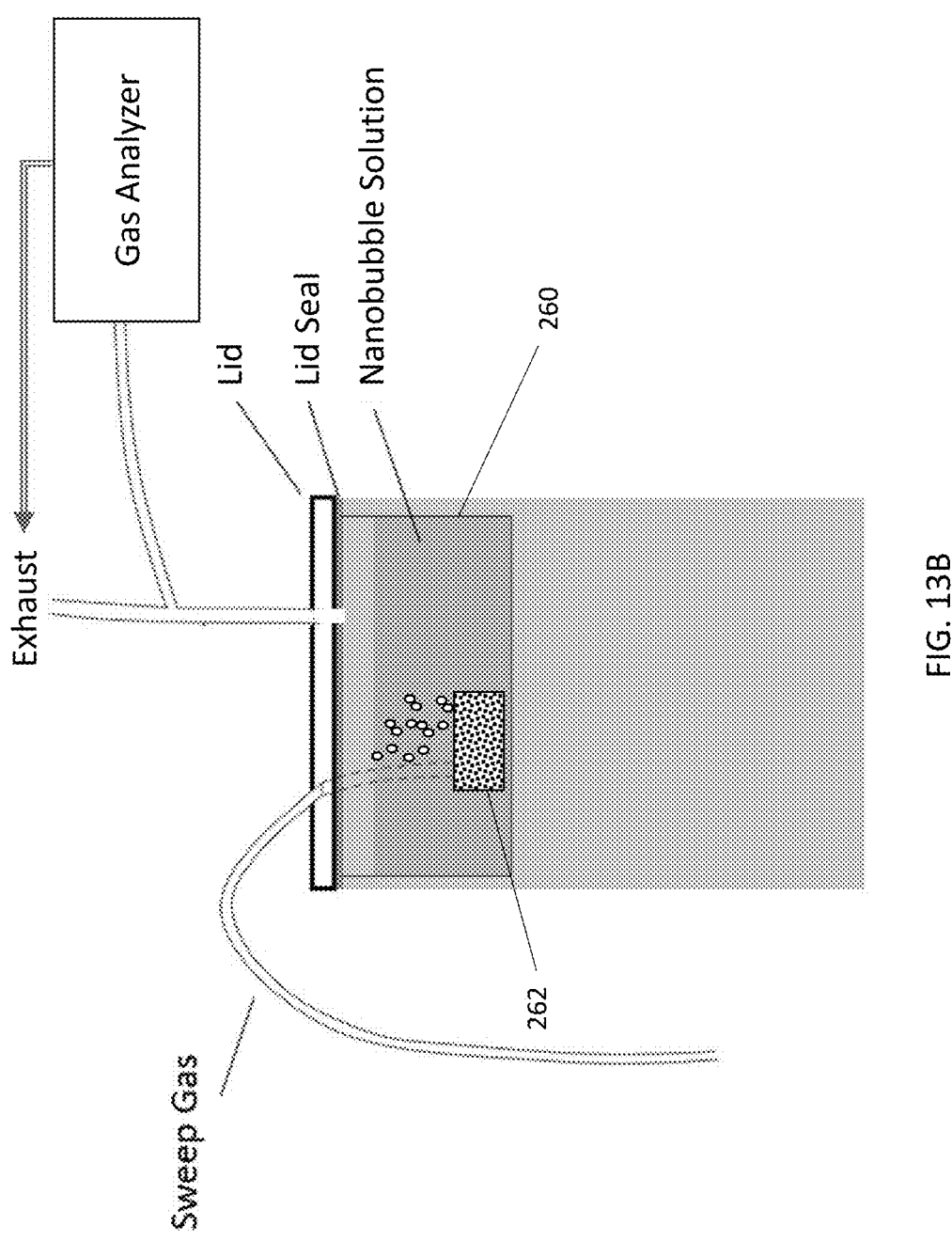
FIG. 13B depicts an exemplary method of measuring the gas content within a liquid using a bubbler.

FIG. 13B depicts an embodiment of an exemplary system showing a method to release nanobubbles from a nanobubble solution where the sweep gas is introduced below the surface of the fluid sample in a basin 260. In some embodiments, the sweep gas is introduced through a bubbler 262 (shown) below the surface of the liquid to increase gas/liquid interaction.

Figure 13C:
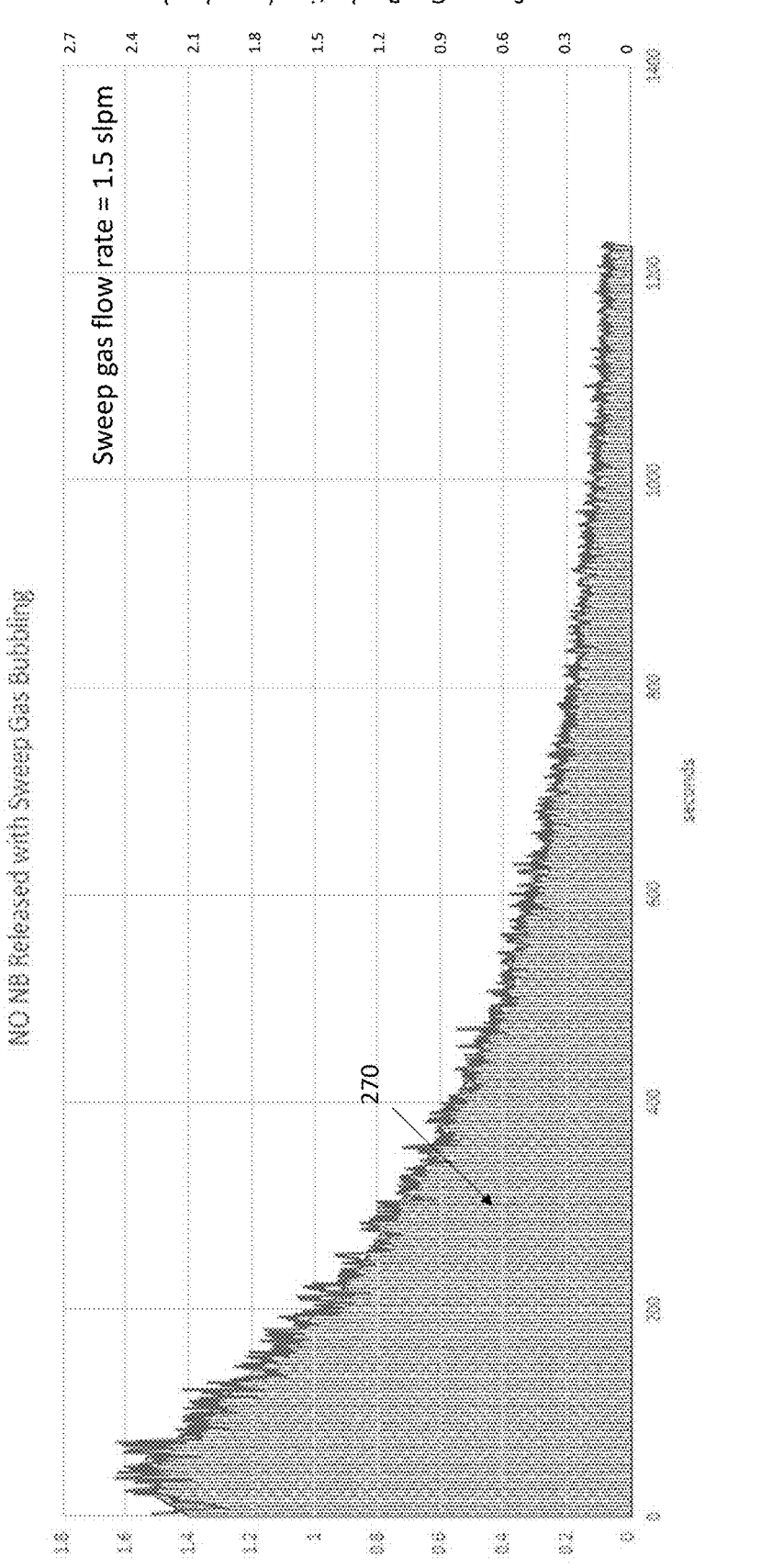
FIG. 13C depicts an embodiment of a graph showing exemplary results from a nanobubble measurement apparatus.

FIG. 13C depicts exemplary sweep gas concentration data when a sample of nanobubble solution is excited within an ultrasonic chamber. A time history of gas concentration (Y-axis) within the sweep gas is captured. Multiplying the gas concentration by the constant sweep gas flow rate results in the gas production level in ppm·slpm (secondary Y axis on the right). In some embodiments, the mass flow of gas exiting the release chamber is measured by a mass flow sensor and utilized to calculate the gas production value.

The amount of nanobubble gas within the liquid sample is calculated as the integral of the sweep gas production level over time, shown as the shaded region 270 of FIG. 13C. In the subject example, the nanobubble gas is nitric oxide and the liquid sample is 100 ml, but the same mathematical approach applies to other gases. The area under the curve is roughly 720 ppm·slpm·sec, which equates to 12 ppm·sliter. Using the relationship that 1 mole of gas occupies 22.4 liters of gas at standard conditions, the result can be written as:

$$\frac{12 \text{ mole NO.sliter}}{1E6 \text{ mole gas}} \times \frac{1 \text{ mole gas}}{22.4 \text{ sliters}} = 5.357E^{-7}\text{mole NO}$$

Assuming the subject gas to be NO (molecular weight of 30.01 g/mol), then the amount of NO in nanobubble form is calculated as:

$$5.357E^{-7}\text{mole NO} \times 30.01\frac{\text{g}}{\text{mole}} = 1.61E^{-5}\text{g} = 16.1 \ \mu g \text{ NO}$$

Thus, 16.1 micrograms of NO is present in 100 ml of liquid. To deliver a dose of 50 micrograms of NO, 310 ml (i.e. 50/16.1*100) of nanobubble solution is required.

Figure 14:
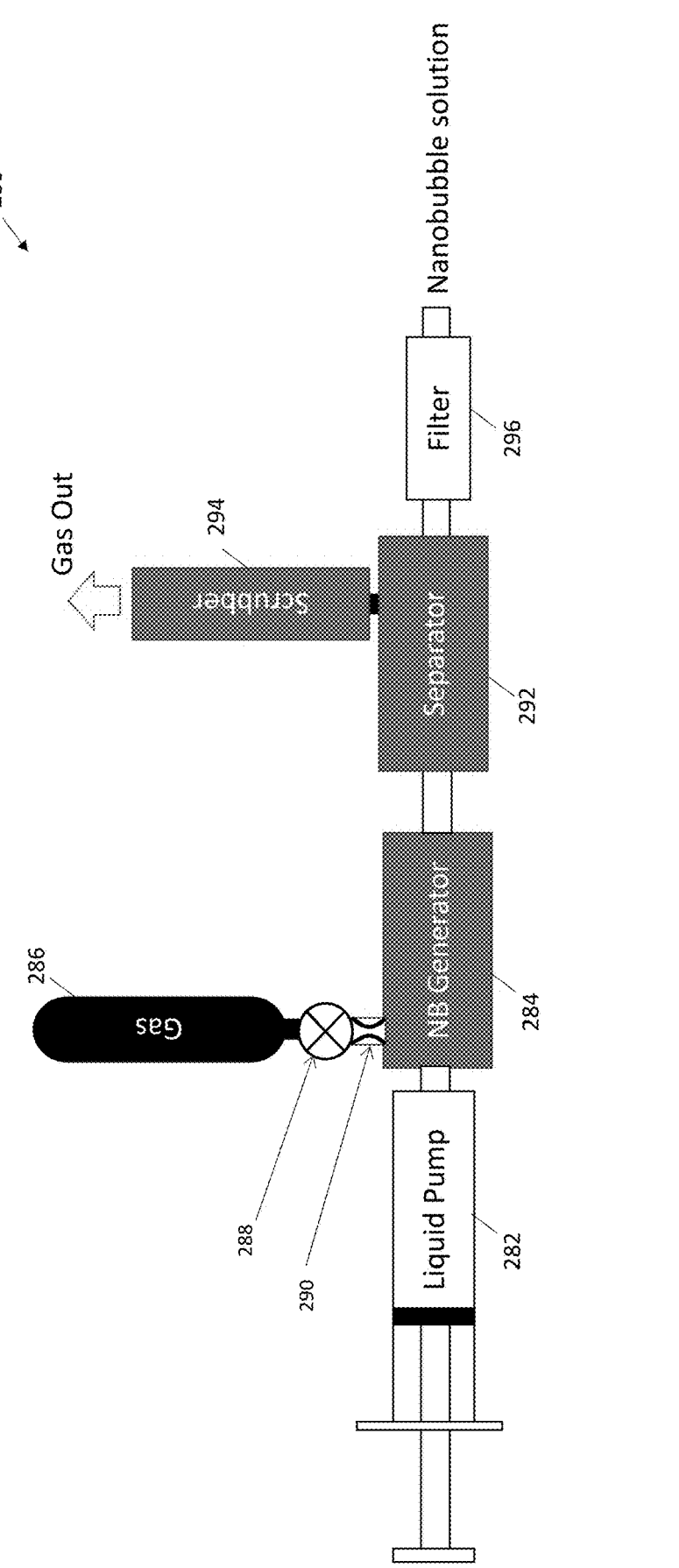
FIG. 14 depicts an embodiment of a nanobubble generation device that utilizes a syringe and compressed gas cylinder.

FIG. 14 depicts an exemplary embodiment of a nanobubble generator system 280 for generation of nanobubbles at the point of use. A liquid is introduced to a nanobubble generator 284 by a pump 282 (e.g., a syringe).

A gas (e.g., NO or a balance of NO in $N_2$) is introduced to the nanobubble generator from a gas source 286, such as a compressed gas cylinder. The gas cylinder connects to a valve 288 that can be manually opened by a user at the time of nanobubble generation. In some embodiments, the valve is automatically opened by a controller based on a fluid pressure measurement (not shown). An orifice 290 limits the flow rate of gas from the gas cylinder. In some embodiments (not shown), a pressure regulator reduces the pressure within the gas cylinder to a lower, working level before the valve. The device is utilized by delivering liquid and gas to the nanobubble generator at the same time. The resulting liquid/gas mixture passes through a gas separator 292 to release gas from the system and isolate only the nanobubble solution. In some embodiments, the exiting gas is scrubbed by a scrubber 294 prior to release into the atmosphere (e.g., removing NO from a NO/$N_2$ gas). In some embodiments (not shown), excess gas is collected in a reservoir (e.g. a bag) for later disposal or reuse. In some embodiments, the nanobubble generator is ergonomically designed with a pistol grip so that as the user squeezes the grip, liquid and gas pass through the nanobubble generator. An optional filter 296 at the outlet of the nanobubble generator removes particulate and pathogens from the solution prior to delivery.

Figure 15:
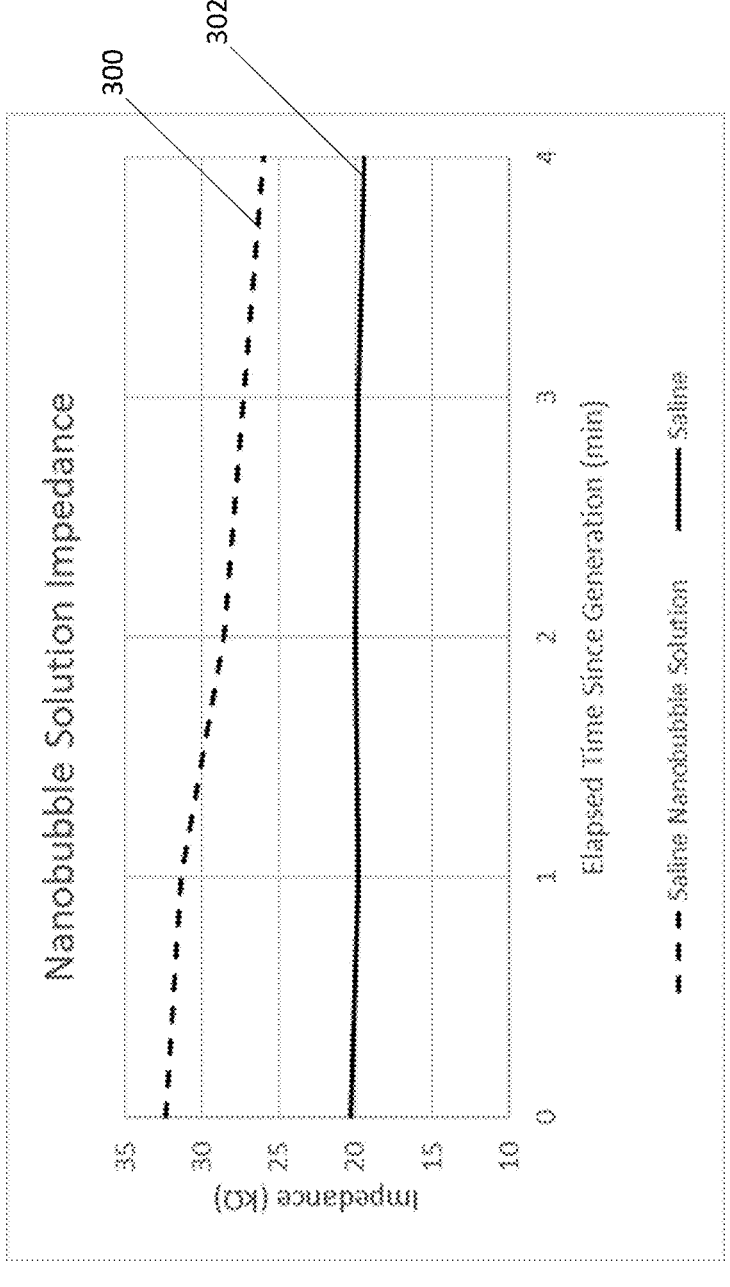
FIG. 15 presents experimental data demonstrating the effect of nanobubbles on the impedance of a solution.

In some embodiments, the impedance of a nanobubble solution is measured as a means of quantifying the quantity of gas in nanobubble form within the solution. Every liquid has a particular electrical conductivity. Gas is not electrically conductive (at least at low voltages). As nanobubbles are generated in a liquid, they decrease the electrical conductivity of the solution. Electrical conductivity is inversely related to impedance, which is more easily measured. The impedance of a liquid is measured by making contact between two or more electrodes and the solution, applying a known voltage (e.g. 5V) across the liquid at a known distance/geometry and measuring the current through the liquid. The resistance in Ohms is then calculated as the applied voltage divided by the current in Amps. FIG. 15 depicts a graph of experimental results from measuring the impedance of two solutions; 1) a NO nanobubble solution made with 10,000 ppm NO and saline (line 300) and 2) saline doped with nitric acid (line 302) to match pH. Both samples had the same pH (4.1). The nanobubble solution impedance was more than 50% greater than the saline impedance. This demonstrates that an impedance (or conductivity) measurement can be utilized to determine the presence of nanobubbles in solution and quantify how many there are. In some embodiments, the system permits removal of NO by a user only when the nanobubble solution concentration is in an acceptable range. In some embodiments, the system utilizes a liquid impedance measurement to determine one or more of presence/absence of nanobubbles in solution and there being liquid in the system (i.e. priming successful, liquid reservoir not empty). In some embodiments, the liquid-contacting electrodes used for measuring impedance of a nanobubble solution are included as part of a disposable tubing set.

Inspiratory Gas Humidification

In some embodiments, NO nanobubbles are introduced to the water in a humidifier. The NO nanobubbles disinfect the liquid, preventing bacterial growth without the use of toxic chemicals. NO that exits the surface of the water into the air is carried to the patient in the respiratory gas to dose the patient. This approach can be used in treating patient conditions like ventilator associated pneumonia (VAP) and pulmonary hypertension.

NO Supply

In some embodiments, a NO gas for nanobubble applications can be sourced from at least one of compressed cylinders (such as tanks), electrical generation and chemical generation (e.g., conversion from $N_2O_4$, NO donor molecules). When a tank source is utilized, some embodiments include a pressure regulator to regulate the gas pressure down to a level that can be more consistent over time. Variation of the gas pressure is also a means to modulate the amount of NO within solution.

In some embodiments, a NO source is built into the nanobubble generator. The NO source can be any type, including but not limited to NO tanks, chemically derived NO (e.g., $N_2O_4$, solid sources), and electrically derived NO (e.g., spark gap, microwave). This can create efficiency by sharing various system components, including but not limited to the enclosure, power supply, user interface, controller, alarm system, back-up battery, flow controllers, pumps, etc.

Figure 16:
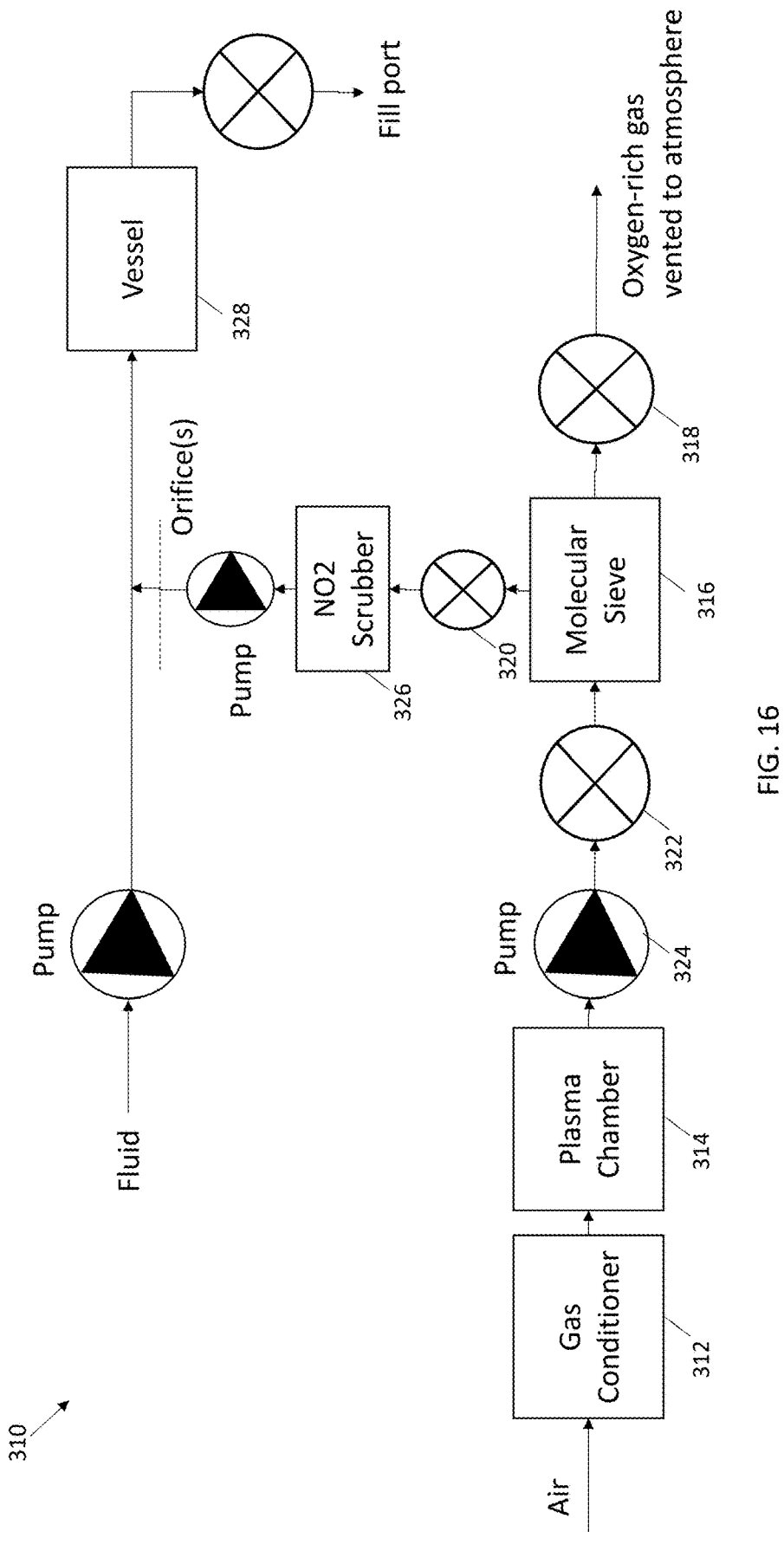
FIG. 16 depicts an embodiment of a NO nanobubble generation system that generates NO with electricity.

FIG. 16 depicts an embodiment of a NO nanobubble generation system 310. Air enters the system through a gas conditioner 312. The gas conditioner can include one or more of particle filter, VOC scrubber, NOx scrubber, and humidity management stage. In some embodiments, the humidity management stage can include a dehumidifier made with desiccant material. The cleaned reactant gas passes through a plasma chamber 314 where nitrogen and oxygen in the reactant gas are broken down into their monatomic forms and recombine. In some embodiments, the plasma is generated by arcing between two electrodes with high voltage. In some embodiments, microwave energy is focused on a point to elevate reactant gas temperature to the state of plasma.

Gas containing NO, referred to as "product gas" is pumped from the plasma chamber to a molecular sieve chamber 316. The chamber is pressurized to a point that $N_2$, NO and $NO_2$ are preferentially attracted by the sieve material. Pressure is initially released by opening a valve 318 to release oxygen-rich gas. Then, the oxygen valve can be closed and the upper valve 320 can be opened to release the gas mixture containing $N_2$, NO, and $NO_2$. In some embodiments, there is a valve 322 between the product gas pump 324 and the molecular sieve chamber 316 to prevent back flow through the pump when the molecular sieve is pressurized. In some embodiments, that valve is a check valve. In some embodiments, two or molecular sieves operate out of phase so that the $N_2$/NO flow is more continuous.

The NO gas mixture then passes through a NOx scrubber 326 that removes $NO_2$ from the mixture. With little to no oxygen remaining in the gas, the NO concentration can be stable. The NO is pumped through a membrane with one or more orifices in it as a liquid is pumped across the surface of the membrane. In some embodiments, the one or more orifices are nano-scale (i.e. <1 micron in diameter). In some embodiments, the one or more orifices are larger (e.g. 0.1 to 3 mm) and the gas is pulled into the liquid flow by the Venturi effect. The liquid shears off the gas flow into bubbles as it flows and is collected in a vessel 328. In some embodiments, the liquid flow is continuous in one direction. In some embodiments, the liquid flow is pulsatile or periodically reversing to enhance nanobubble formation. In some embodiments, the one or more orifices are part of a venturi, whereby the flow of liquid is sped up in the region of gas introduction by a reduction in flow path cross-sectional area, thereby creating a low-pressure region that draws gas into the liquid. In some combinations of gas and liquid, the liquid can be stored within the reservoir for days to weeks (at least) prior to loading into a delivery device for patient treatment.

Figure 17:
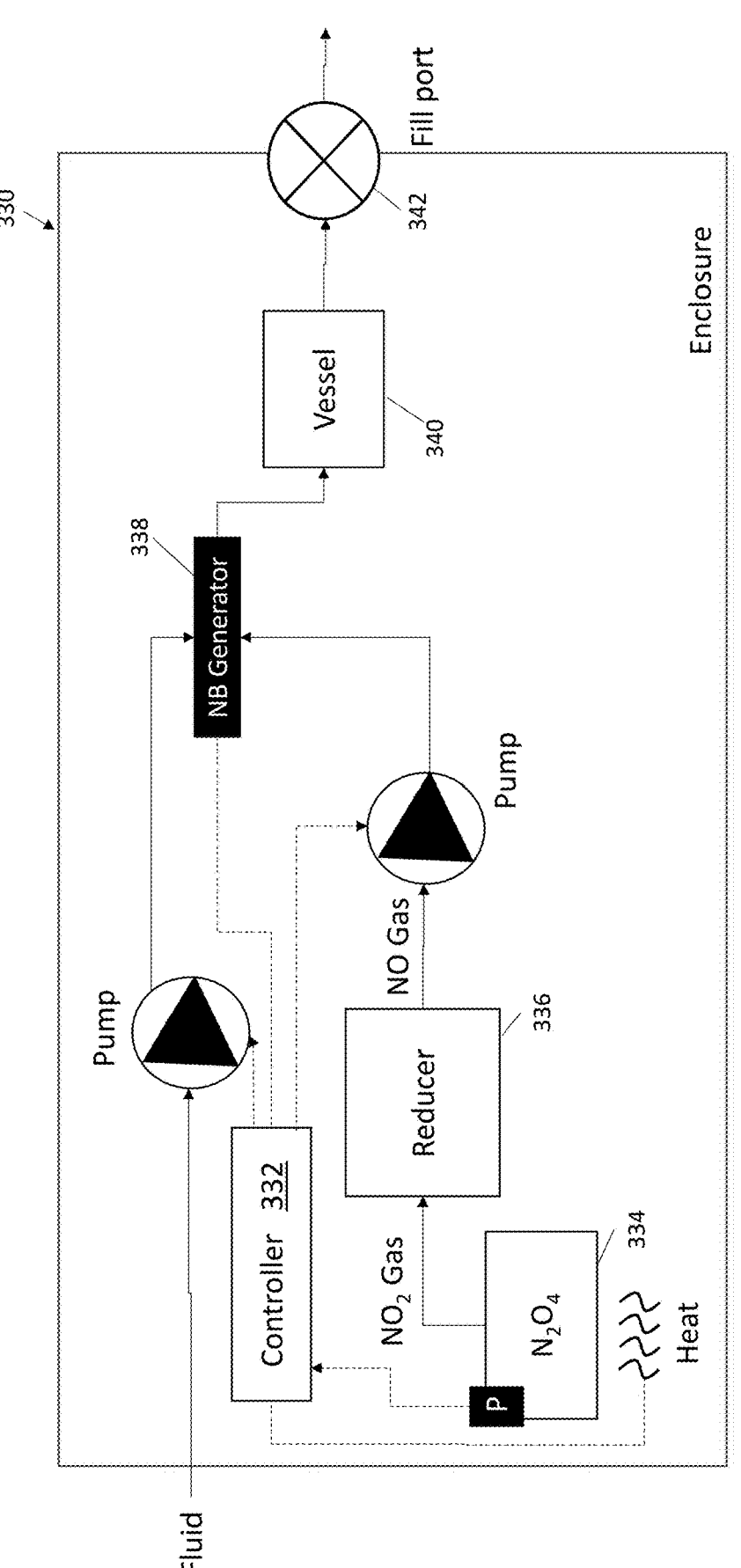
FIG. 17 depicts an exemplary embodiment of an integrated NO generator and nanobubble generator system that sources NO from $N_2O_4$.

FIG. 17 depicts an exemplary embodiment of an integrated NO generator/nanobubble generator system 330 that sources NO from $N_2O_4$. $N_2O_4$ that is variably heated to release $NO_2$ gas at a desired rate. The heater 334 is closed-loop controlled by a controller 332 based on the pressure of the $NO_2$ gas. The $NO_2$ gas is reduced to NO by a reducer 336 and pumped to a nanobubble generator 338 where the gas is introduced to the liquid. In some embodiments, the $NO_2$ gas is diluted with another gas (e.g. $N_2$, air) before the reducer. The controller turns the liquid pump on/off as needed. In some embodiments, the liquid pump speed is modulated by the controller based on the required nanobubble solution generation rate and input requirements of the nanobubble generator. In some embodiments, gas is introduced to the liquid in the presence of ultrasound stimulation, the ultrasound creating cavitations in the liquid that get filled with NO gas. In some embodiments, the NO gas is diluted with nitrogen gas (not shown) before nanobubble formation. Nanobubble solution is collected in a reservoir or vessel 340 prior to release through a fill port. In some embodiments, a fill port valve 342 is controlled by the controller (not shown). The entire system can be packaged in an enclosure.

Figure 18:
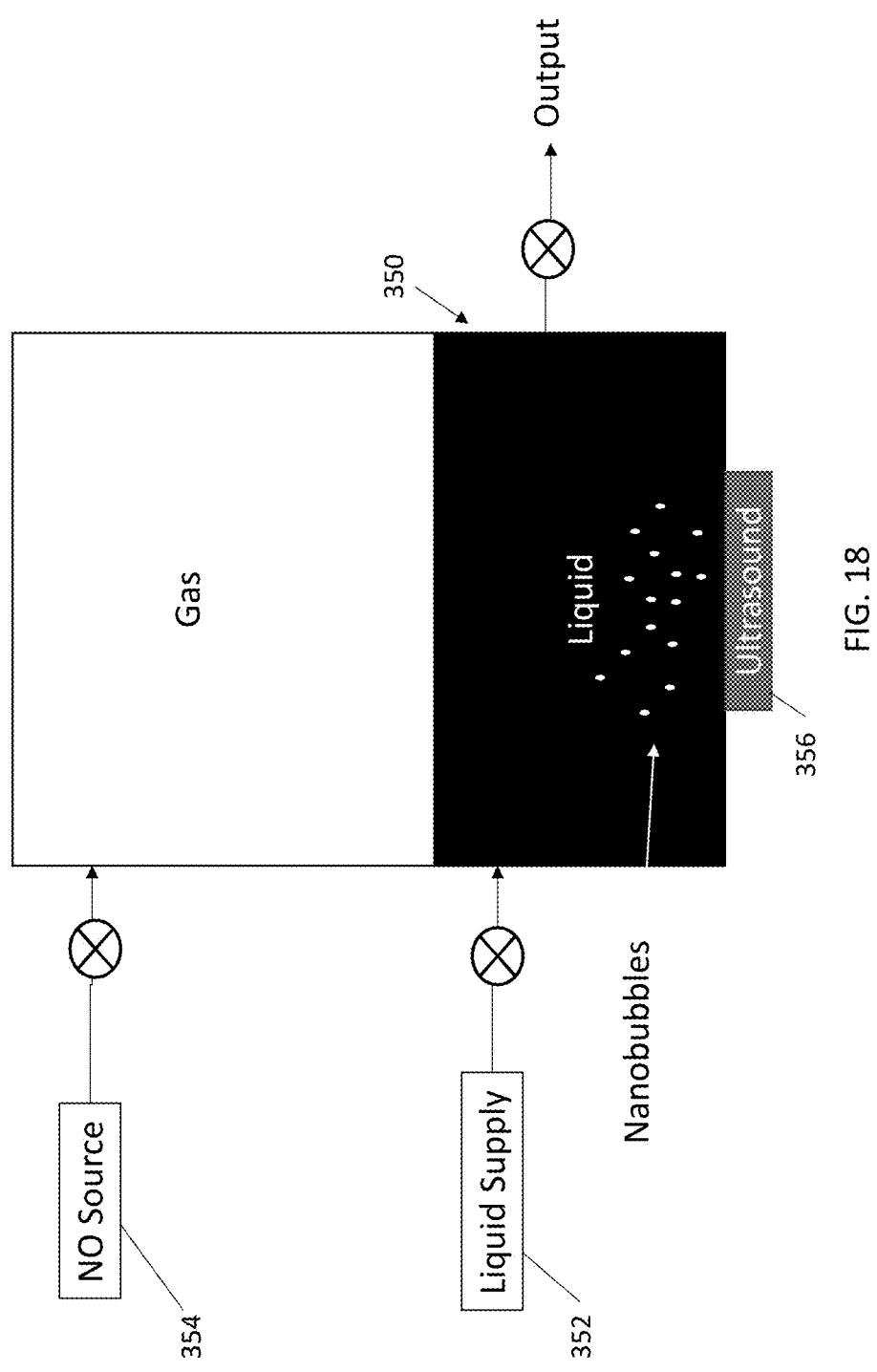
FIG. 18 depicts an embodiment of a system where NO nanobubbles are generated in a vessel using ultrasound.

FIG. 18 depicts an embodiment of a system where NO nanobubbles are generated in a vessel by ultrasound. Liquid is introduced to a chamber 350 from a liquid source 352. Gas is introduced from a gas source 354 and dissolves within the liquid. In some embodiments, the gas is pressurized within the chamber. An ultrasonic actuator 356 at the bottom of the vessel stimulates the liquid to create nano cavitations in the liquid which are filled by dissolved gas coming out of solution. The ultrasound stimulation frequency and/or amplitude is varied by the device controller to vary the rate and size of bubbles generated. The duration that the ultrasound is applied to the liquid determines the overall quantity of nanobubbles within the liquid.

Similar integration between NO generator and nanobubble system can be achieved with other nanobubble forming methods, as listed above.

Delivery devices (e.g., a syringe) are loaded either manually, by gravity or a pump (not shown). In some embodiments, the nanobubble solution is diluted with another liquid after the sample is drawn from the nanobubble solution generation system. For example, in one specific example, a clinician draws 25 ml of nanobubble solution from the system into a syringe. The clinician then draws an additional 25 ml of pure saline liquid into the syringe, thereby diluting the solution 50%. In some embodiments, the dilution liquid is the same liquid that was used to generate nanobubbles. In other embodiments, the dilution liquid is a different liquid than the one used for nanobubble generation.

In some embodiments, a NO nanobubble generator is configured to be portable. Portable systems are equipped with one or more features including carrying features (e.g. handles) and battery power. In other embodiments, NO nanobubble generators are installed in a stationary location. In some embodiments, a nanobubble solution generator may be dedicated to a specific hospital bed, for example. In some embodiments, a stationary nanobubble solution generator is used to fill vessels used for transporting NO nanobubble solutions. In some embodiments, a nanobubble solution generator includes a clock or timer, enabling the system to automatically start and/or stop operation with respect to time. In one exemplary embodiment, a nanobubble solution generator automatically generates nanobubble solution at the same time each day.

In some embodiments, a nanobubble solution generator is placed at the bedside of a patient for delivery of nanobubble solution by infusion pump at home or in the clinic. In some embodiments, the nanobubble generator operates continuously to maintain a reservoir of nanobubble solution at a target concentration. In other embodiments, typically where the liquid/gas mixture supports longer-lived nanobubbles, the nanobubble generation system operates intermittently. In some embodiments, the nanobubble generation system operates for a known amount of time to reach a maximal concentration of nanobubbles in a recirculation architecture, the stops nanobubble generation to conserve gas. The system then resumes nanobubble generation after one or more of a set amount of time associated with a specific amount of nanobubble attrition, or after a measurement of nanobubble concentration (e.g. molarity, optical diffusion spectroscopy, etc.) indicates that the nanobubble concentration has fallen below a target value.

In some embodiments, the target concentration is a maximum concentration achievable for a particular liquid, gas combination. In some embodiments, the system targets a non-maximum concentration or a range of concentrations. In some embodiments, the nanobubble solution generator includes a gas sensor (e.g. electrochemical sensor) that measures gas in solution, providing feedback to the bubble generation control loop.

Colder liquids can hold more dissolved gas, in turn slowing the degradation of nanobubbles. In some embodiments (not shown), the system includes a chiller that reduces the temperature of the circulating liquid, thereby increasing the capacity of the liquid to hold gas. Various types of chillers have been contemplated, including but not limited to ice, liquid nitrogen, compression/expansion cycles and thermoelectric chillers. In some embodiments (not shown), the liquid reservoir is insulated to prevent absorbing heat from the ambient environment.

Figure 19:
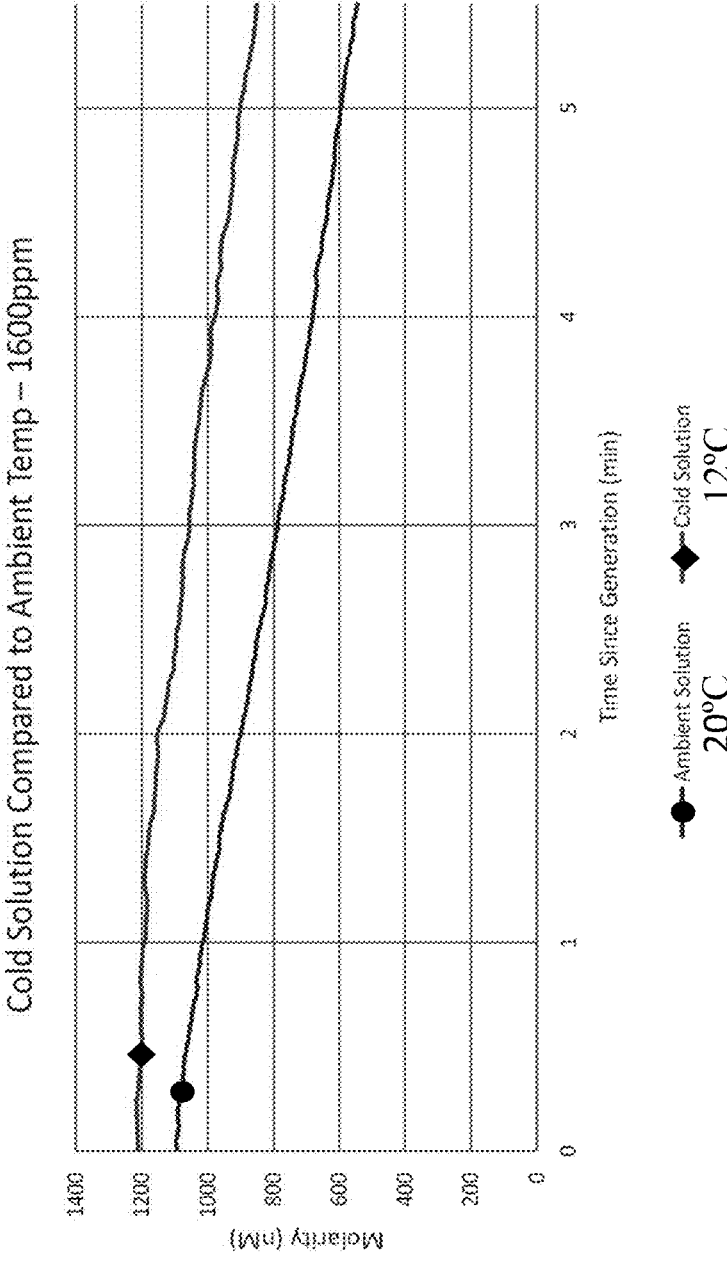
FIG. 19 depicts the effect of cold liquid on nanobubble generation and longevity.

FIG. 19 presents an exemplary graph showing experimental data with NO nanobubble solution generated from saline and 1600 ppm NO gas. The two samples were generated in solution at 20° C. and 12° C. This eight degree Celsius decrease in temperature resulted in 10% higher molarity. The NO gas concentration in solution decreases more slowly over time in the colder sample as well. The cold temperature limit of a liquid used for nanobubble solution generation and/or a nanobubble solution is only limited by the freezing point of the solution. In some embodiments, the NO generation system utilizes a look up table or equation that quantifies the reduction in nanobubble concentration over time. In some embodiments, the NO generation system presents a number on the user interface indicative of the molarity of the nanobubble solution over time. In some embodiments, the NO generation system generates an audible and/or visual alarm when the calculated NB concentration in a sample or in the reservoir (in the case of stopped flow) falls below a threshold amount. In some embodiments, the lower threshold for nanobubble concentration is related to the minimum therapeutically effective dose.

Figure 20:
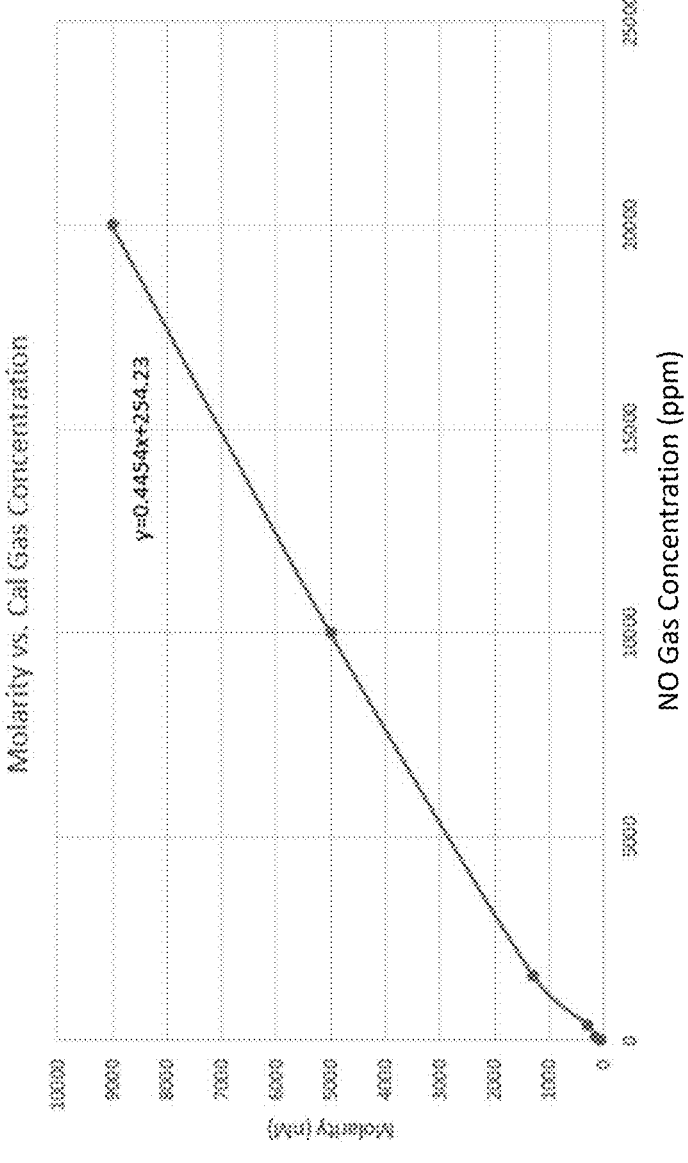
FIG. 20 depicts the relationship between gas concentration and solution molarity for nitric oxide gas.

FIG. 20 depicts the relationship between gas concentration and the concentration of gas in solution (i.e. molarity). Higher concentration gas delivered to the nanobubble generator results in higher concentration solution. In some embodiments, the controller utilizes a function or lookup table to determine the gas concentration to us to achieve a target concentration of gas in solution. The controller then varies the gas source to supply the required gas concentration. In some gas concentration is varied by diluting gas from a fixed concentration source (e.g. compressed tanks). In other embodiments, the controller modulates the level of NO generation at the source (e.g. varying the frequency and/or duty cycle of an electric NO generator, or varying the flow rate of $NO_2$ from an $N_2O_4$ NO generator.

Figure 21A:
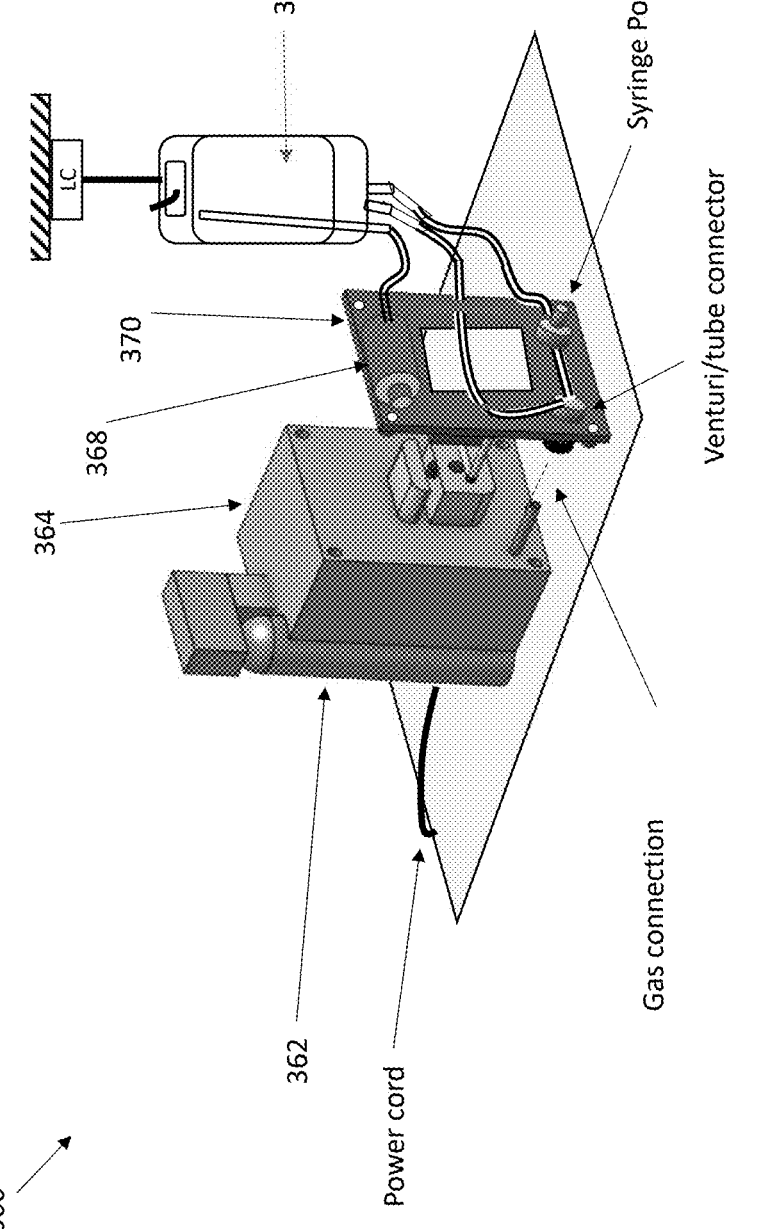
FIG. 21A depicts an expanded view of a modular nanobubble generation system with capital equipment and disposable components.

FIG. 21A depicts an exemplary nanobubble generation system 360. A gas source 362, such as a compressed NO cylinder, is installed as part of the system. High pressure NO gas within the cylinder passes through a pressure regulator within the controller 364 to reduce the pressure. Gas flow is then controlled by the internal controller (e.g., microcontroller, FPGA, etc.) using a valve. A pump (e.g., peristaltic pump) is on the front face of the system of interfacing with the recirculation path tubing. A reservoir 366, such as a bag, can be hung from a hook. The reservoir as shown includes three ports that serve as a liquid outlet, a liquid return and a gas outlet. The gas outlet port consists of a tube that extends up to the gas headspace within the reservoir 366.

In the subject embodiment, the tubing set can be fastened to a backer card of a cartridge 370 to facilitate locating the tubing into the pump head and align the gas inlet to the venturi fitting. The backer card snaps onto the front face of the controller by interfacing with button head fasteners that protrude from the front face of the controller. Attached to the backer card is a scrubber cartridge 368 to remove $NO_2$ and/or other harmful gases prior to release to the atmosphere. Tubing is lashed to the backer card as well. One tube terminates with a spike that engages the reservoir. The tube extends to the pump head and on to the Venturi fitting. In some embodiments, the tube is comprised of different material within the pump head versus elsewhere. In one specific embodiment, the tubing is silicone pump tubing within the pump head region and PVC tubing elsewhere to reduce pressure losses due to tube wall expansion as well as reduce cost. From the Venturi/gas port, the tubing passes through a syringe port and back to the reservoir. The syringe port opens when a syringe is inserted into a Luer fitting on the port. In some embodiments (not shown), the syringe port is covered by a protective flap attached to the backer card. The flap prevents incidental contact with the syringe port that could contaminate sterility. The flap is lifted to gain access to the syringe port when collecting nanobubble solution from the system.

In some embodiments, the venturi fitting engages the gas tube connection on the front panel of the controller with a push-to-connect fitting. This facilitates installation of the cassette while also ensuring a gas-tight seal. In some embodiments, the gas connection extending from the front of the controller is composed of metal (e.g., stainless steel) for long service life. The gas flows into the venturi fitting and through an orifice to enter the flow of liquid in the tubing. In some embodiments, the diameter of the liquid flow path necks down in the region of gas introduction to create a venturi.

Figure 21B:
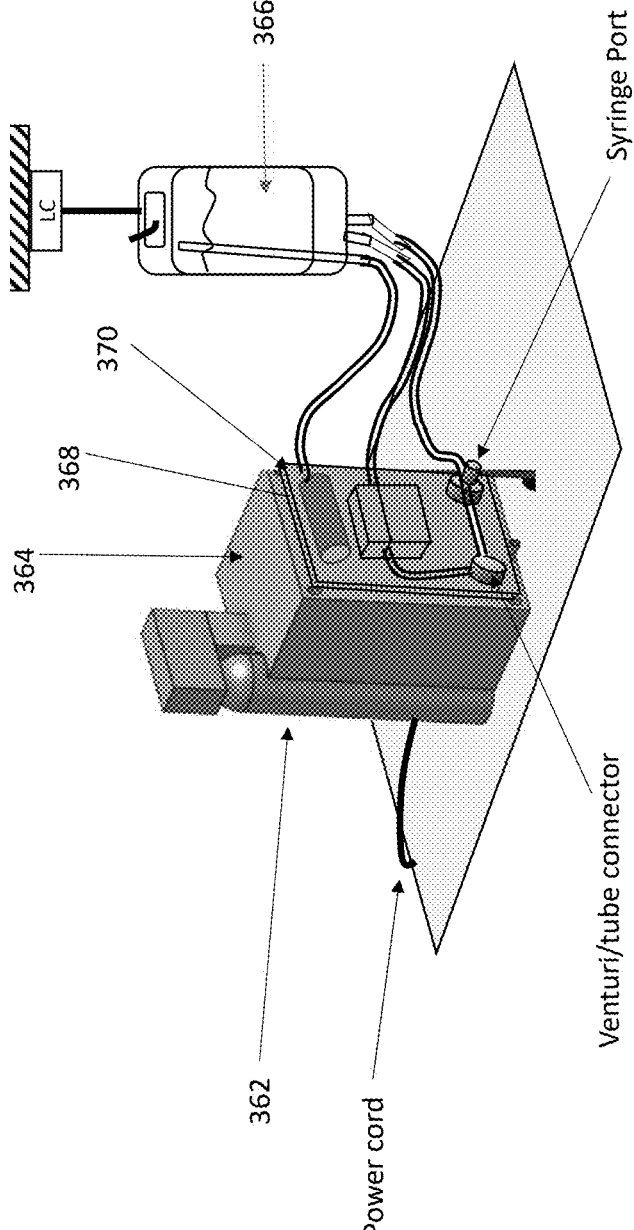
FIG. 21B depicts an exemplary embodiment of a modular nanobubble generation system with liquid volume measurement.

FIG. 21B depicts an exemplary embodiment showing the cartridge or cassette 370 of FIG. 21A installed on the front face of the controller 364. The pump tubing has been installed in the pump head and pump head as been closed. In some embodiments, the controller detects the presence of the cassette/tubing and prevents pump operation and gas flow in the absence of a cassette. In some embodiments, the cassette is detected with an optical sensor. In some embodiments, the pump head can detect tubing based on the current required to turn the pump. In some embodiments, the controller can detect whether or not the pump head is closed.

The reservoir can hang from a hook connected to a load cell. The load cell is utilized by the controller to detect the presence/absence of a reservoir. In some embodiments, the system does not begin generation of nanobubble solution, permit the flow of gas, or turn the pump head in the absence of a reservoir hanging from the load cell. In some embodiments, the controller generates a warning to the user when the reservoir mass falls below a particular threshold, indicating that it is nearly empty and should be replaced. In some embodiments, the controller prompts the user to replace the gas cylinder when the pressure within the cylinder, as measured by a pressure sensor downstream of the cylinder, indicates that the pressure has fallen below a threshold.

When the nanobubble generation system of FIG. 21B is turned on, it initially turns on the pump for a particular amount of time or number of revolutions to prime the tubing set with liquid. After the tubing set has been primed to at least the nanobubble generator, gas flow is turned on to generate nanobubbles.

Figure 22:
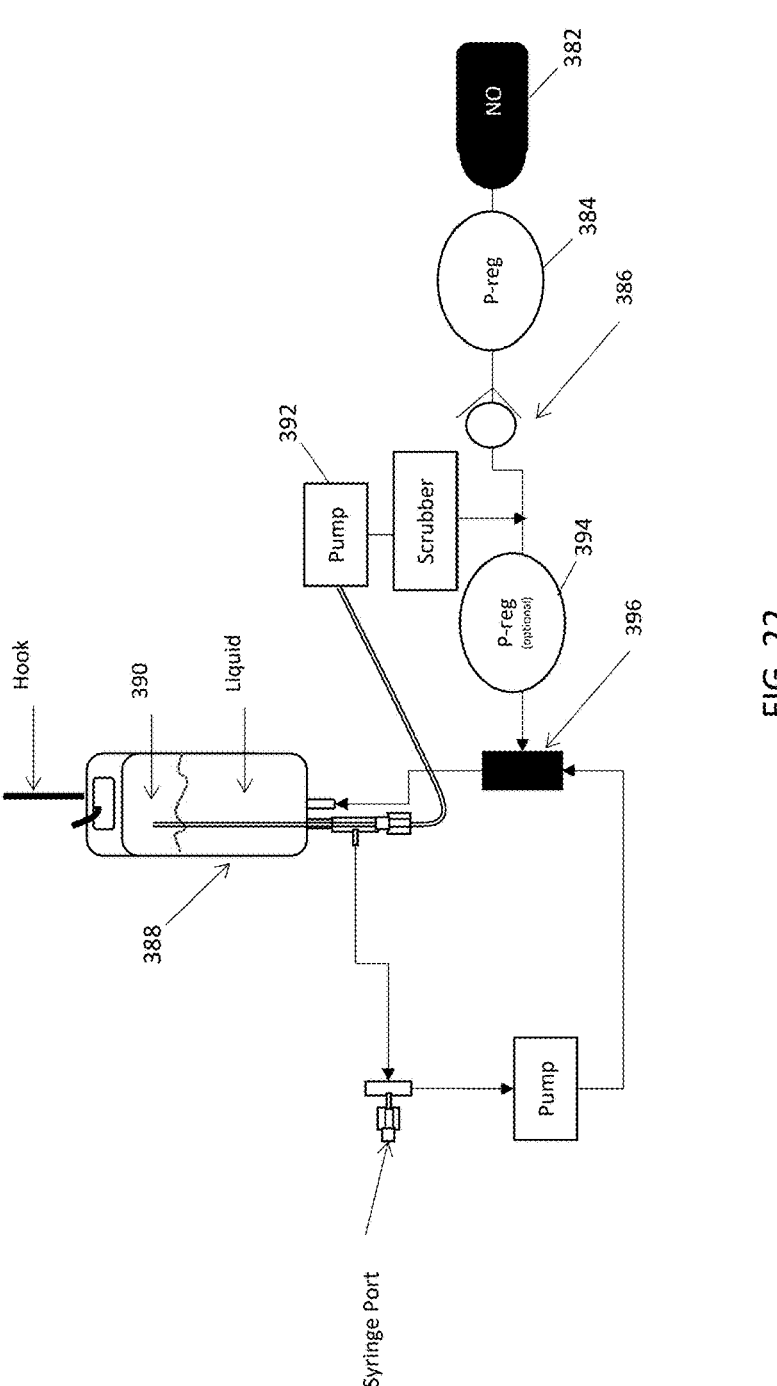
FIG. 22 depicts an exemplary embodiment of a nanobubble generation system that reuses gas.

FIG. 22 depicts an exemplary embodiment of a nanobubble generation system 380 that reuses the gas from the nanobubble generation process. Gas from a gas source/ reservoir 382 passes through an optional pressure regulator 384 to reduce the gas pressure. A check valve 386 in the fresh gas pathway prevents contamination of the NO source by reverse flow of the gas. Gas extracted from the headspace 390 of the reservoir 388 is delivered by pump 392 to the gas inlet flow path. In some embodiments, a pressure sensor (not shown) in fluid communication with the reservoir headspace is utilized by the device controller to determine when to run the pump in order to prevent over pressurization of the reservoir. Headspace pressure can be used by the controller as a proxy for knowing how much gas is in the system. An optional secondary pressure regulator 394 regulates the pressure of the combined fresh and re-used gas as it enters the nanobubble generator 396. In some embodiments, the pressure regulator is a mass flow controller. This approach of reusing gas from the reservoir headspace conserves gas.

In some embodiments, the nanobubble generator 396 runs continuously until it is turned off or until a fault or error condition occurs. In some embodiments, the nanobubble generator operates intermittently. The generator operates for a period of time (typically a few minutes) to bring the nanobubble concentration up to a maximal amount. Then, the system pauses operation for a period of time (e.g. 5 to 20 minutes to an hour) prior to automatically starting to flow liquid and gas again. Intermittent operation enables less gas to be used over time while still providing a clinically relevant quantity of nanobubbles in solution. On startup, some embodiments of a nanobubble generator initiate gas flow before initiating liquid flow to prevent liquid from traveling in the reverse direction through the gas path. In some embodiments, a check valve in the gas path prevents reverse flow of the liquid. In some embodiments, a nanobubble generator has fixed pump speed settings and gas pressure regulator settings such that a controller is not required for the system to function.

Figure 23A:
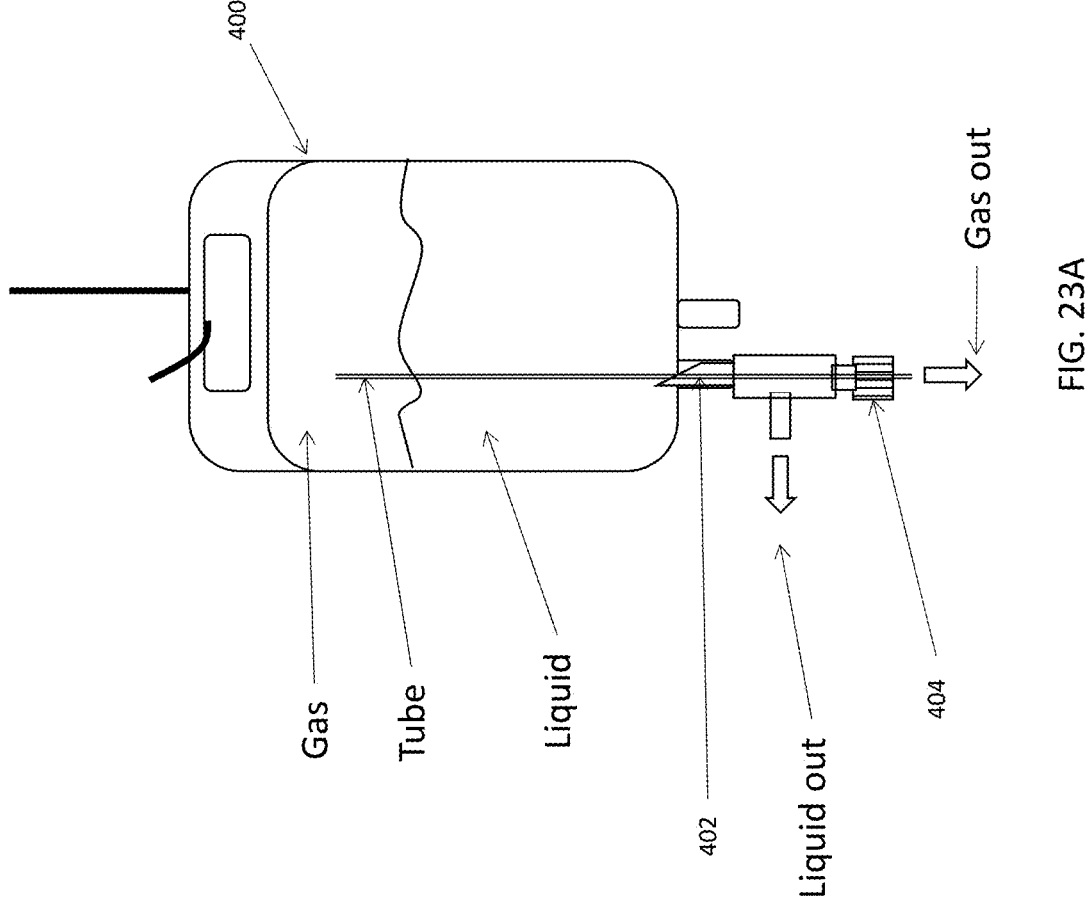
FIG. 23A depicts an exemplary method for removing excess gas from a reservoir.

FIG. 23A depicts an embodiment of the interface between a tubing set and a two-port reservoir. A spike port of a reservoir 400, such as a bag, is engaged with a spike 402. This is typically done with the bag upside down to prevent loss of fluid from the bag once spiked. Once spiked, a long tube is introduced to the spike through a Touhy Borst connector 404. The tube is inserted to the far end of the reservoir and the Touhy Borst connector is tightened about the tube. The reservoir is then hung from a hook. Liquid exits out the side of the spike component and gas from the headspace of the reservoir exits through the tube.

For example, the tubing set can be comprised of tubing (e.g., silicone, Tygon, PVC, etc.) and fittings made from polymer, ceramic or metal. In some embodiments, the tubing set is provided sterile. Sterilization is done with typical methods including EtO, autoclave, radiation, dry sterilization, chemical sterilization and other methods. In one method, the tubing set is first filled with high concentration nitric oxide gas to sterilize the tube set. In other methods, the nanobubble solution is utilized to sterilize the tubing set.

Figure 23B:
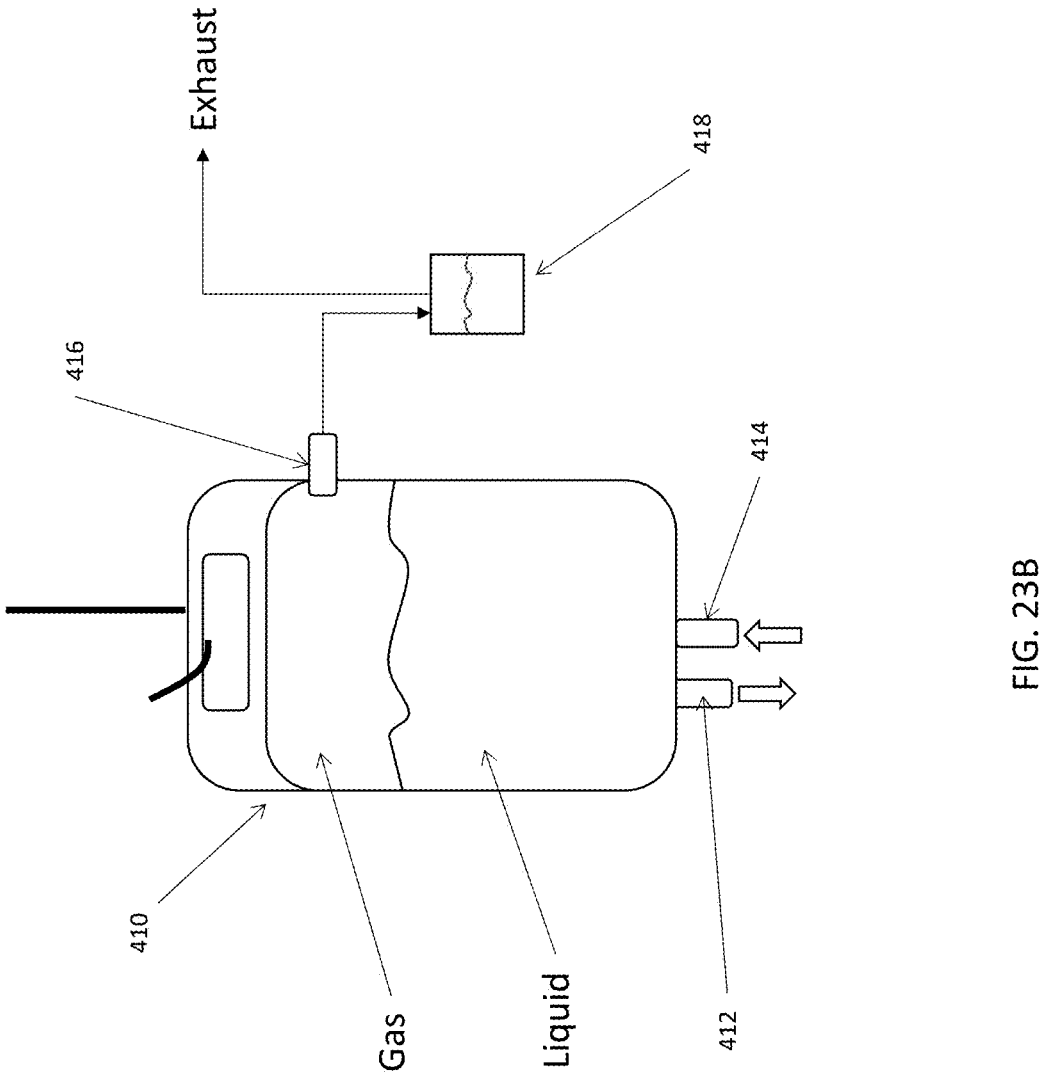
FIG. 23B depicts a three-port liquid reservoir.

FIG. 23B depicts an embodiment of a three-port liquid reservoir 410. The two fittings 412, 414 are used for liquid removal and liquid return, respectively. The upper fitting 416 is for gas release from the headspace of the reservoir 410. In some embodiments, gas is released passively due to pressure build-up in the headspace. In some embodiments, gas within the headspace is actively removed (i.e., by pump). FIG. 23B depicts an optional water trap 418 that removes liquid from the gas stream before it exits the system. In some embodiments, the exhaust line is connected to a house vacuum system. In some embodiments (not shown), the pressure regulator in the exhaust line prevents the headspace pressure from exceeding a particular threshold.

Figure 24:
FIG. 24 depicts a nanobubble generation system that utilizes a reservoir that is pre-filled with the liquid and gas to be used for nanobubble solution.

FIG. 24 depicts an embodiment of a nanobubble generation system 420 that utilizes a reservoir 424 that is provided with both the liquid and gas components of a nanobubble solution. At the manufacturing site, the reservoir it partially filled with degassed liquid with the headspace filled with the therapeutic gas (e.g. NO in a $N_2$ balance). Prior to use, the reservoir 424 is connected to a nanobubble generation 422 (e.g. through spike ports). A liquid pump 426 in the nanobubble generation system draws liquid/solution from the bottom of the reservoir 424, where it passes through a sample port 428 and the pump 426 prior to entering a nanobubble generator 422. A gas pump 430 draws gas from the headspace of the reservoir 424 and pushes it to the nanobubble generator 422. Within the nanobubble generator, a portion of the gas is formed into nanobubbles within the liquid. Microbubbles and gas rise to the surface of the liquid within the reservoir, returning to the reservoir headspace for reuse. In some embodiments, one or more of the liquid pathway, sample port and nanobubble generator are included with the reservoir as an assembly. Providing the entire liquid and gas pathway as a single, closed assembly can be beneficial in preventing contamination of the contents with air, infectious material, and particles.

In some embodiments, the liquid and gas to be used in a nanobubble solution are provided in a common container. The container is aggressively shaken and vibrated to generate bubbles of all sizes, including nanobubbles, into the solution. In some embodiments, the solution is left still for a period of time to permit micro bubbles and larger bubbles to coalesce and float to the top of the liquid. In some embodiments, a portion of the solution is removed from the bottom of the container after a period of time, the period of time being associated with the amount of time for all microbubbles to have floated to the surface (e.g. 15 seconds). In another embodiment, the solution is removed from the bottom of the container through a non-porous filter (e.g. 0.22 micron) that only permits nano-sized bubbles.

Figure 25:
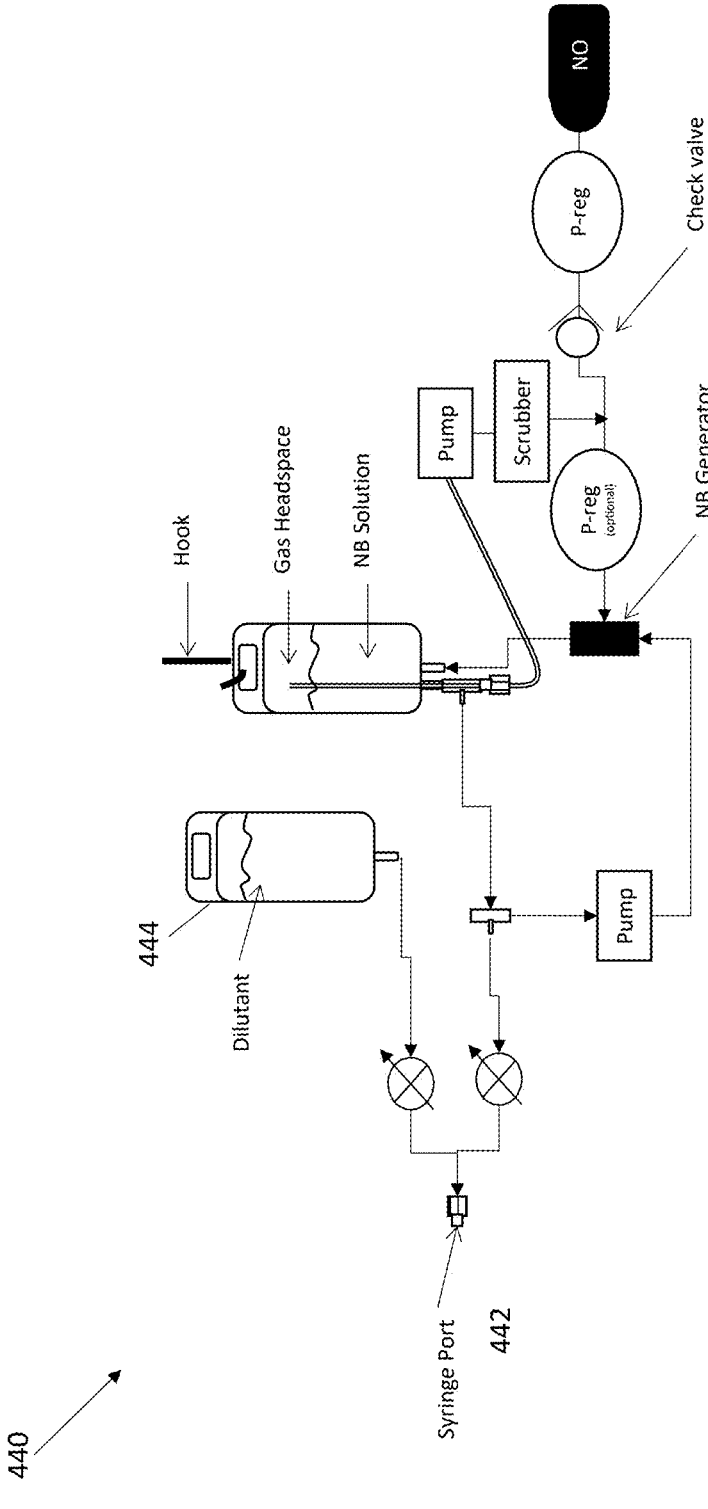
FIG. 25 depicts an exemplary embodiment of a nanobubble generation system with variable dilution.

FIG. 25 depicts an embodiment of pneumatic architecture of a nanobubble generation system 440 that can provide a variety of nanobubble concentrations. The system operates as described above to generate a target amount of nanobubbles in solution within the recirculation loop. The nanobubble concentration is a function of NO gas concentration, liquid flow rate, gas pressure/flow rate, duration that the system has been circulating, and duration that the system has been idle. Nanobubble solution is withdrawn from the system through a port 442. The nanobubble solution is drawn from a blend of nanobubble solution within the recirculation loop and dilution liquid. Variation in the ratio between the two liquids provides a means to dial in a particular concentration of nanobubbles in solution, varying from full strength (no dilution) to large amounts of dilution (e.g. 100:1) from a dilutant reservoir 444. The ratio of flow from the two liquid sources can be controlled automatically by the controller (not shown) or by manually setting one or more flow controllers prior to drawing the nanobubble solution.

Figure 26:
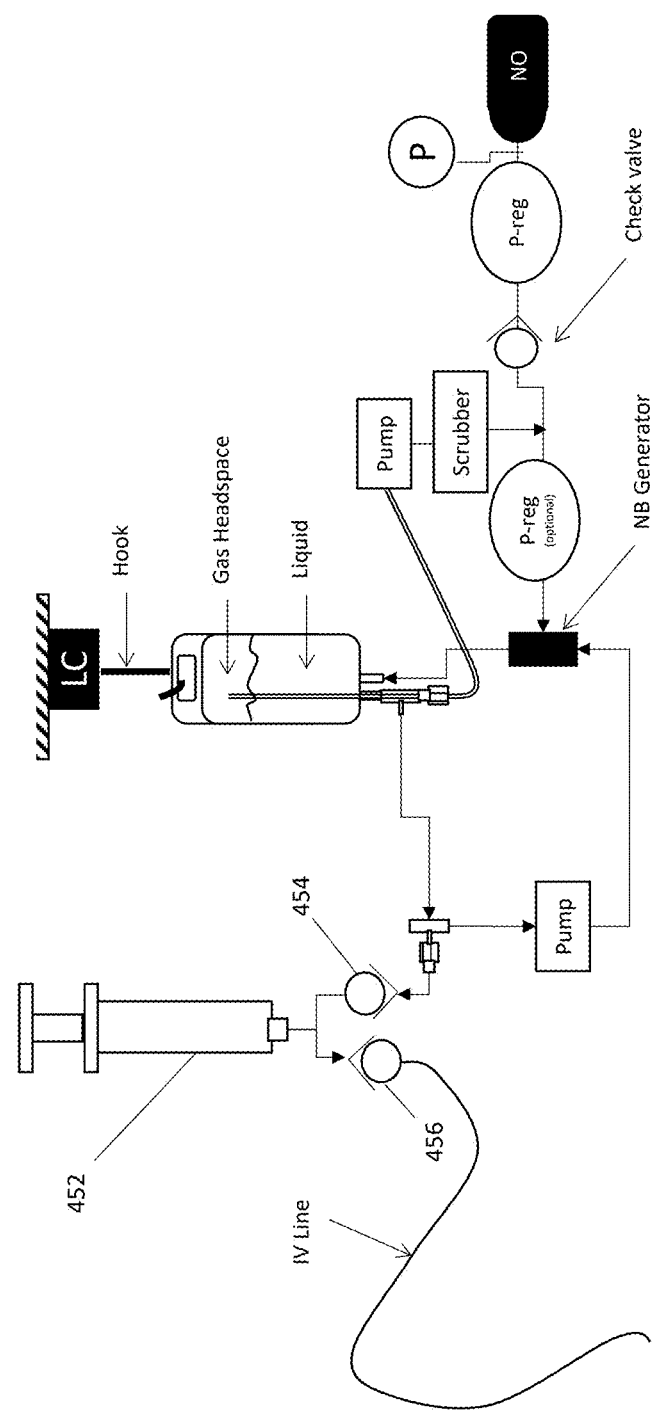
FIG. 26 depicts an exemplary embodiment of a nanobubble generation system that utilizes a syringe pump for solution delivery.

FIG. 26 depicts an embodiment of a nanobubble generation and delivery system 450 that utilizes a pump 452, such as a syringe pump, to draw nanobubble solution from the system and deliver it to an application (e.g., a patient). Check valves 454, 456 before and after the syringe direct flow from the nanobubble solution tubing set to the nanobubble application. In some embodiments, the syringe pump 452 delivers nanobubble solution to a catheter for IV-delivery of nanobubble solution. In some embodiments, the syringe pump periodically delivers nanobubble solution to lesion to treat infection.

Figure 27:
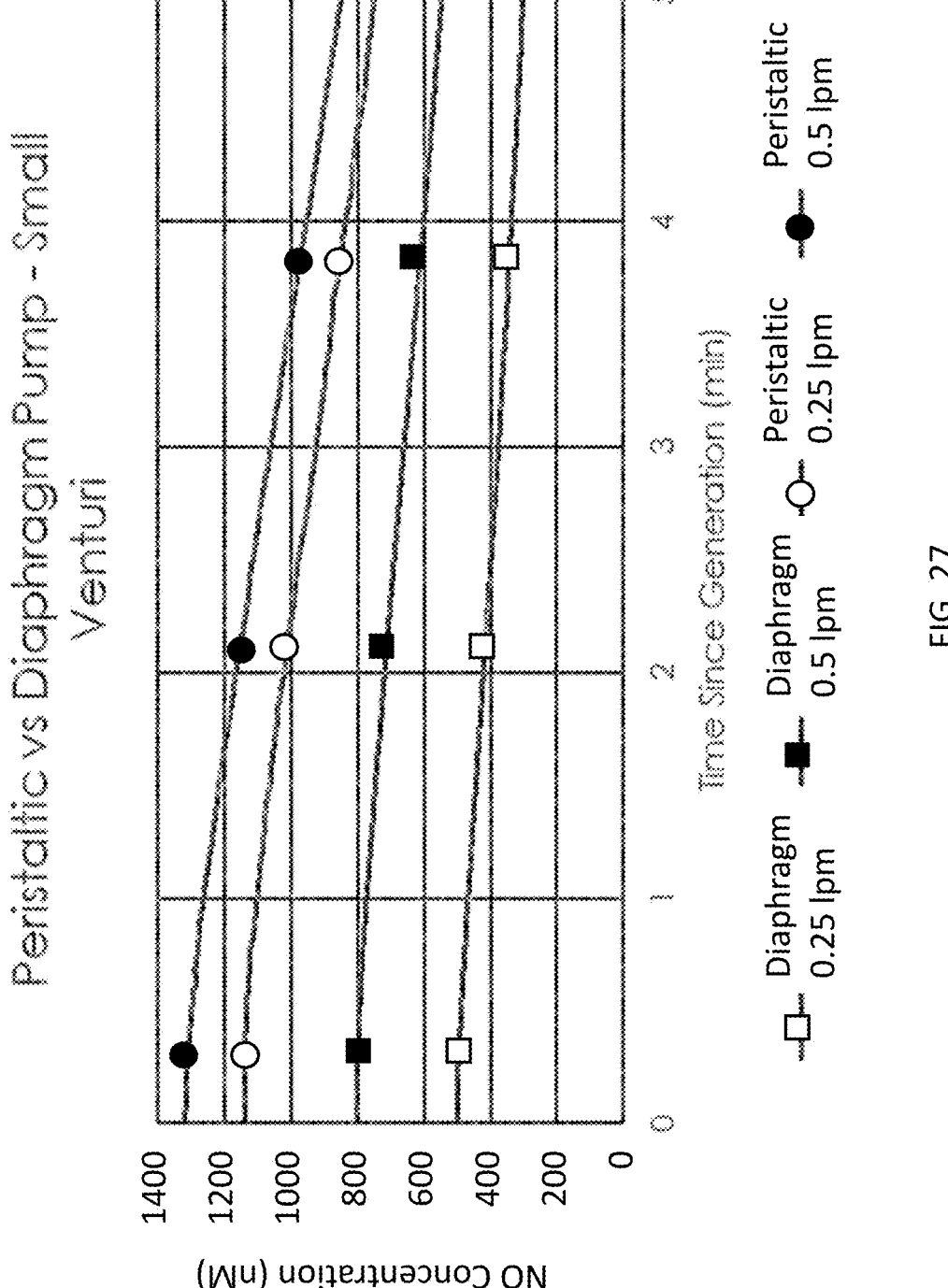
FIG. 27 depicts an exemplary graph of NO concentration utilizing a peristaltic pump for moving nanobubble solutions.

Although there are many ways to transfer nanobubble solutions between two locations, some methods are better than others. Nanobubble solutions can be sensitive to vibration and heat. For this reason, pump mechanisms that minimize heat and vibration can retain a greater amount of nanobubbles in solution. FIG. 27 depicts an exemplary graph showing experimental results measuring NO nanobubble solution over time for a system using a peristaltic pump and a system using a diaphragm pump. The X axis is time, and the Y axis is molarity of NO in solution (i.e., moles of NO per liter of liquid). In practice, the molarity of an NO solution can vary from 1 nM to 1000 mM, depending on the gas, liquid, temperature, and/or pressure. Operating at the same flow rate, the peristaltic pump results in a greater than 50% increase in nanobubble concentration in the solution. Other pumping methods that involve low vibration and heat (e.g., syringe pumps) can provide similar benefits in a nanobubble generation system. FIG. 28A depicts an example of a rotary peristaltic pump 460. FIG. 28B depicts an example of a linear peristaltic pump 470 where three or more actuators sequentially pinch a tube in order to propel fluid. FIG. 28C depicts a dual syringe pump 480 that can provide continuous fluid flow by compressing the syringes out of phase.

Figure 28D:
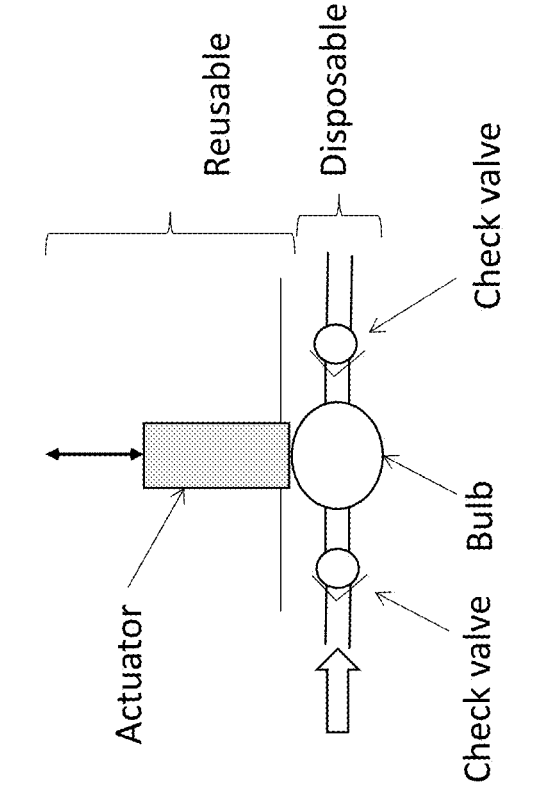
FIG. 28D depicts an exemplary embodiment of a bulb diaphragm pump.

FIG. 28D depicts a fluid liquid pump 490 that consists of a bulb (or diaphragm) with check valves on either side. An actuator compresses the bulb to push liquid out of the bulb to the right. As the actuator decompresses the bulb, the bulb regains its shape and fills with fluid from the left side of the image. This design allows for the bulb and check valves to be part of a sterile, disposable tubing set while the actuator can be part of capital equipment. In some embodiments (not shown), the function of the check valves is accomplished by pinch valves in the capital equipment. This simplifies the depicted portion of the disposable tubing set further to just a bulb and tube. In some embodiments that utilize pinch valves, the pinch valve includes a displacement sensor to report to the controller the position of the pinch valve. In some embodiments, pinch valve position information is used by the controller to detect whether or not tubing has been inserted into the pinch valve (i.e. the pinch valve closes more when there is no tube). In some embodiments, pinch valve position information is used by the controller to detect a non-responsive pinch valve (e.g. solenoid failure, electrical connection failure, etc.).

Figure 28E:
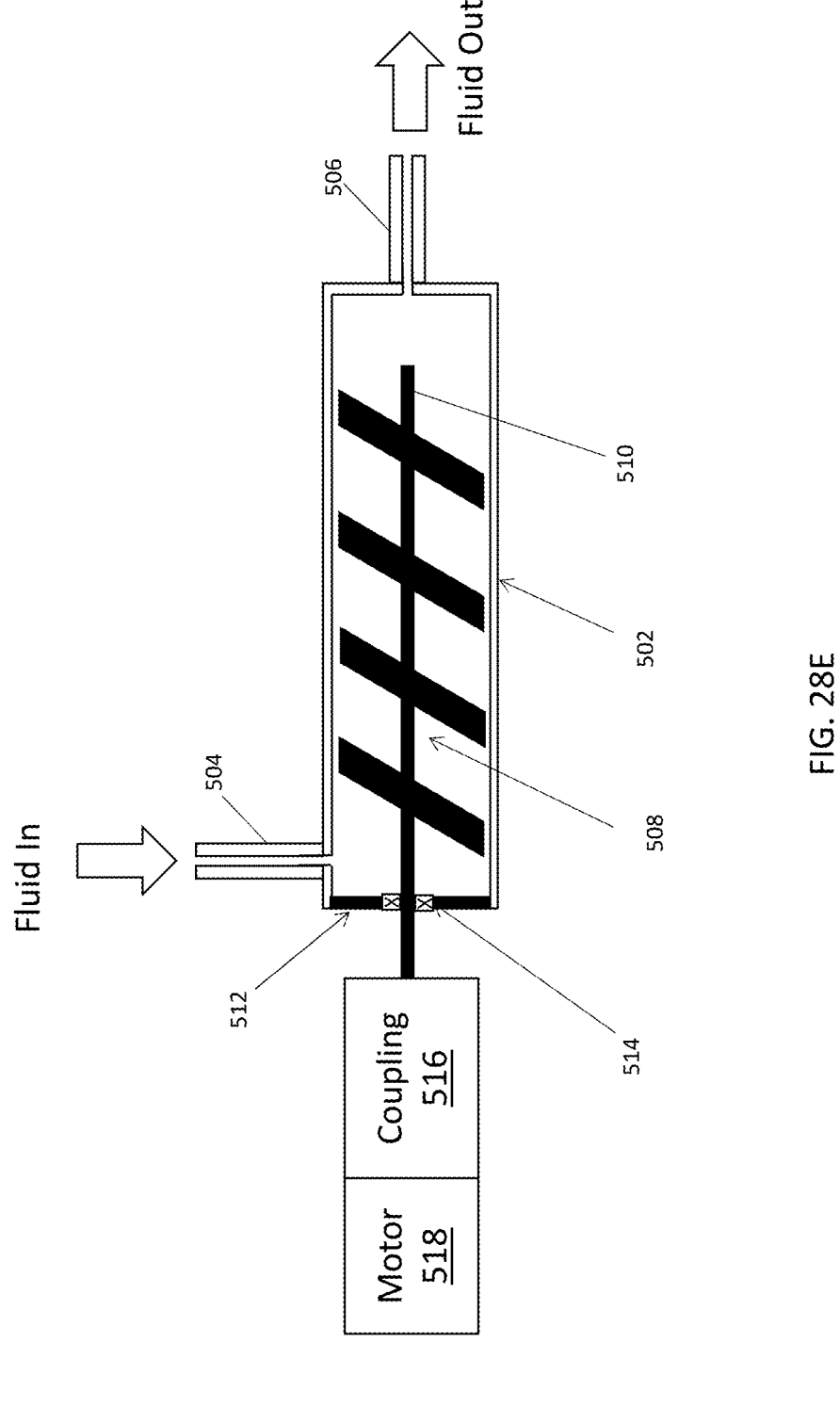
FIG. 28E depicts an exemplary embodiment of a screw pump.

FIG. 28E depicts an exemplary screw pump design 500 for moving a fluid/gas solution. The pump is comprised of a pump body 502 with a fluid inlet 504 and fluid outlet 506. A screw mechanism 508 on a shaft 510 is inserted into an open end of the pump body. An end cap 512 seals the open end of the pump body and includes optional seals 514 (e.g. lip seals) for sealing against the screw shaft. The shaft connects to an optional coupling 516 which can facilitate installation and removal of the screw pump. A motor 518 turns the screw pump coupling and shaft. At low to moderate rotational speeds, this type of pump induces low shear on the fluid, thereby protecting nanobubbles within the solution. In some embodiments, the screw pump body, shaft and endcap are provided to a User as a disposable or re-sterilizable assembly.

Figure 29:
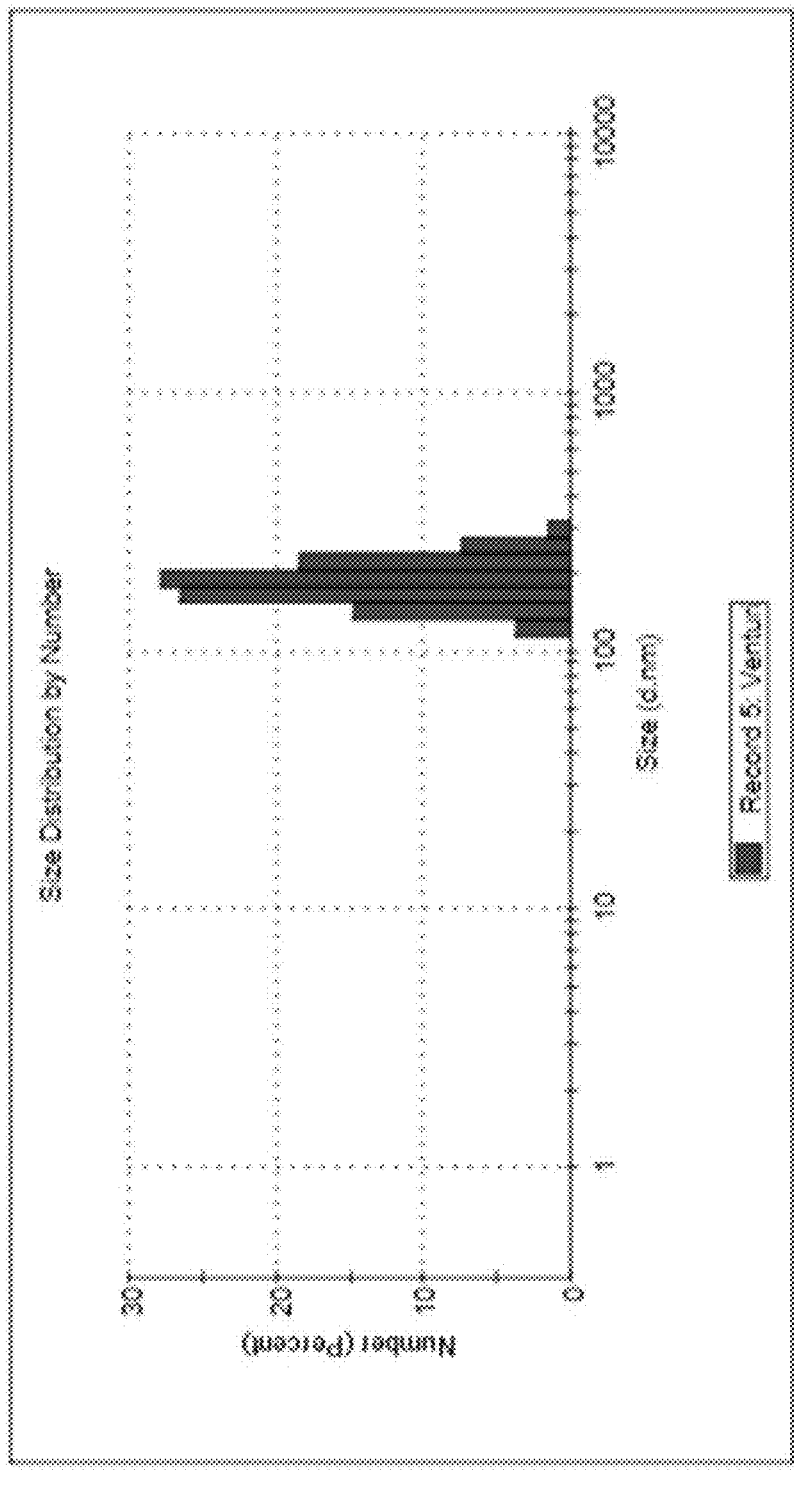
FIG. 29 depicts exemplary nanobubble size distribution within a nanobubble solution.

FIG. 29 presents a graph of exemplary nanobubble size distribution data for a NO nanobubble solution in saline, as measured by a dynamic light scattering instrument (Malvern Zetasizer). The Venturi nanobubble generator operated for 15 minutes at a liquid flow rate of 5.1 lpm and a gas flow rate of 0.06 lpm. The majority of bubbles were in the sub 200 nm range.

Figure 30B:
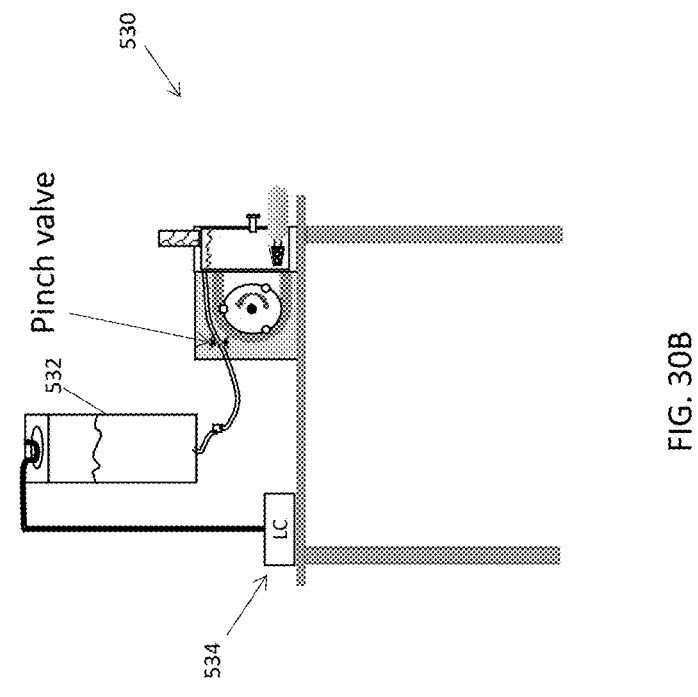
FIG. 30B depicts an exemplary embodiment of a bench-top nanobubble generation system.
Figure 30A:
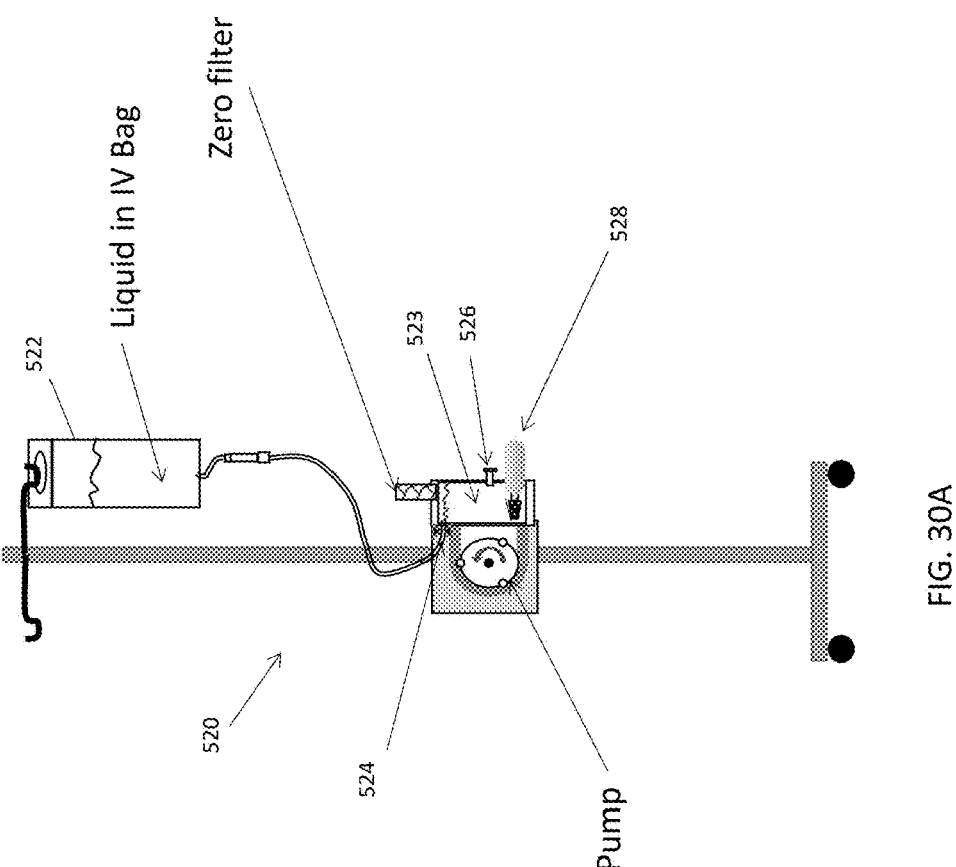
FIG. 30A depicts an exemplary embodiment of a pole-mounted nanobubble generation system.

FIG. 30A depicts an embodiment of a nanobubble generator system 520 that is mounted to a rolling pole. Liquid is sourced from a reservoir 522, such as an IV bag, that hangs from the pole. Flow from the bag into a nanobubble solution reservoir 523 is regulated by a pinch valve 524, controlled by a controller. The pinch valve is opened when the level in the nanobubble solution reservoir drops below a particular level. Other types of valves can be utilized, however a pinch valve is beneficial because it maintains the sterility of the tube inner surfaces. The fluid level drops as a user draws solution from the reservoir via a syringe port 526. A peristaltic pump draws solution from the solution reservoir and sends it through a nanobubble generator. In the nanobubble generator, gas sourced from a gas cartridge 528 is introduced to the liquid in a way that generates nanobubbles. The liquid with nanobubbles and gas return to the reservoir. Excess gas in the system floats out of the solution and exits through a zero filter located at the top of the reservoir that removes NO and $NO_2$ from the exhausted gas.

FIG. 30B depicts an embodiment of a nanobubble generator system 530 that is used on a bench. A reservoir 532, such as a bag of liquid, hangs from a stand with a load cell 534 that measures the mass of the bag and liquid. In some embodiments, the load cell information is utilized to confirm that a full bag is hanging at the beginning of treatment. In other embodiments, the load cell signal is utilized to determine whether or not the bag is empty. In some embodiments, the rate of change in mass of the bag is utilized to determine a liquid flow rate in the system.

Figure 30C:
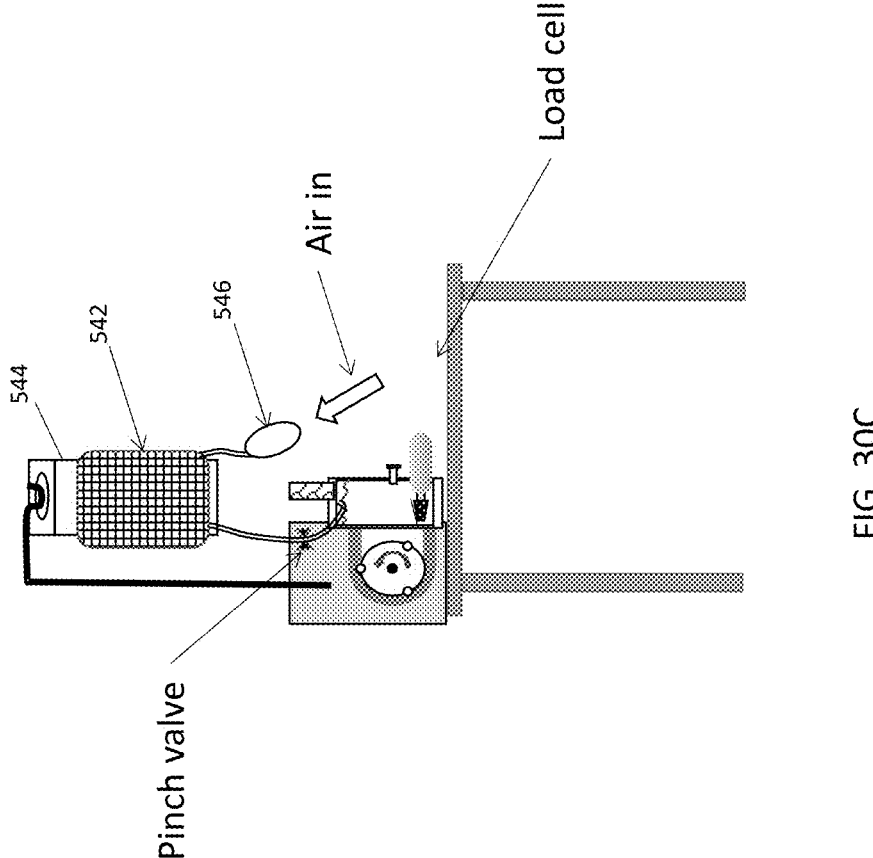
FIG. 30C depicts an exemplary embodiment of a bench-top nanobubble generation system that utilizes a pressure cuff on a liquid reservoir.

FIG. 30C depicts another embodiment of a nanobubble generator system 540 with a pressurized cuff 542 around a liquid reservoir 544. Pressure is built in the cuff by squeezing a bulb 546 with check valves on its inlet and outlet to pump air. In some embodiments, the pressure of the cuff is measured by the system controller. When the pressure falls below a particular threshold, it is indicative that the reservoir is at or near empty. In some embodiments, the pressure induced in the liquid by the pressurized cuff propels the liquid through the system. In some embodiments (not shown), the reservoir bag is placed on the table surface (not hanging), and relies on the cuff pressure to propel liquid into the nanobubble generation system, rather than gravity. In some embodiments, the cuff pressure is measured by a sensor (not shown) and communicated to the device controller in a wired or wireless way.

Figure 31:
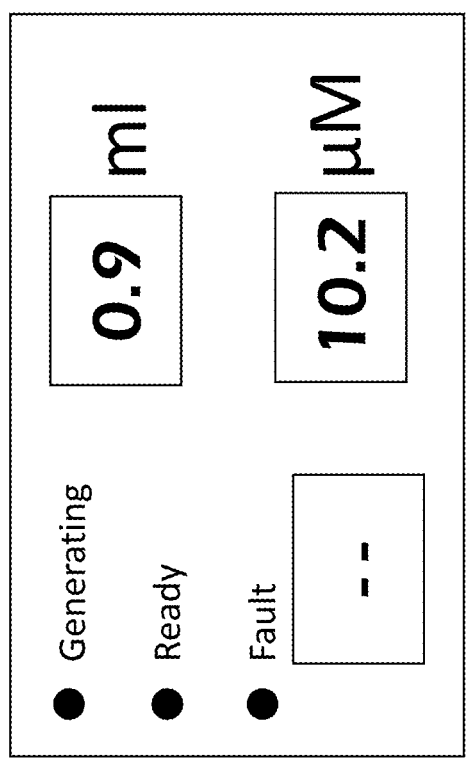
FIG. 31 depicts an exemplary user interface for a liquid solution generator.

FIG. 31 depicts an exemplary user interface 550 for a nanobubble generation system. The interface includes illuminated indicators for one or more of priming, generating, ready, fault, and power. Fault numbers are presented in a numeric display which shows the corresponding fault number. Example faults include low liquid level, low gas pressure, time-out in a system state, tube set missing, and sensor fault. In some embodiments, a missing tube is detected by a sensor in the pump head. The exemplary user interface also includes an indication of available liquid solution volume and solution concentration. In some embodiments, the system controller runs a supervisory process to detect fault conditions and either shut down or enter a fault mode. In some embodiments, a nanobubble generation system includes a voice recognition feature. In practice, this feature is utilized by a User to be able to start and stop solution generation by voice. For example, a physician in a sterile field can command the device to "Start solution" and "stop solution" without leaving the sterile field. This enables interaction with the system without breaking sterility.

Figure 32:
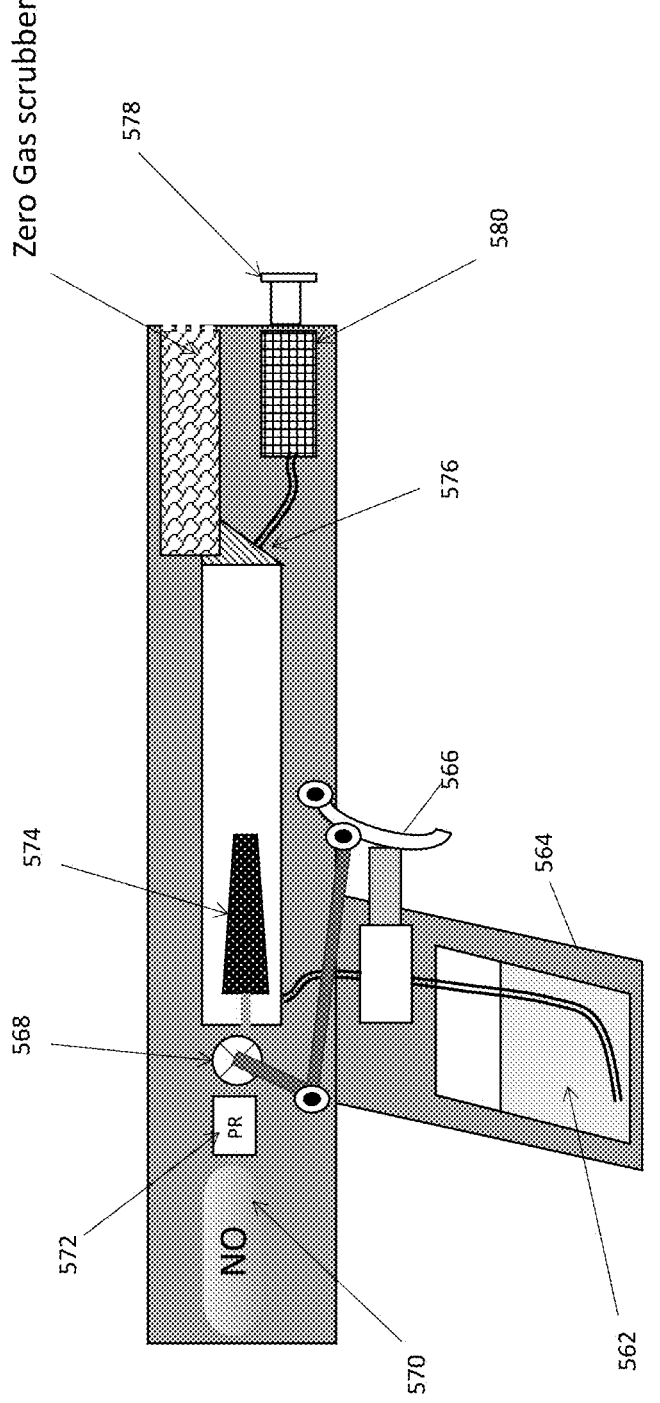
FIG. 32 depicts a hand-held nanobubble generation system.

FIG. 32 depicts an embodiment of a hand-held nanobubble solution generation device 560. Liquid is stored in a reservoir 562 in the pistol-grip handle 564 of the device. When a user squeezes the pump lever 566, a pump mechanism (e.g. syringe pump) pulls liquid from the reservoir 562 and pushes it into a chamber. Squeezing the lever also opens a valve 568 that releases gas from a pressurized source 570, such as a gas cannister. The pressure of the gas is reduced with a pressure regulator 572 before the valve. Gas flows from the valve to a nano-porous material 574 that permits the gas to enter the liquid in nano-sized channels. The liquid flowing over the nanochannels shears off the gas channels into nanobubbles. Not all of the gas enters the liquid. Hence, a gas separation mechanism 576 (e.g. membrane) is utilized to separate the gas from the nanobubble solution. Gas is released to atmosphere after passing through a scrubber that removes one or more materials (e.g. NO, $NO_2$). The remaining liquid solution passes through an outlet 578, such as a Luer fitting, and out of the device. In some embodiments (shown), the liquid solution passes through a sterile filter 580 (e.g. 0.22 micron) prior to exiting the system. In practice, a user connects the hand-held nanobubble solution generator to a catheter to deliver nanobubble solution to a patient. In some embodiments (not shown), the pressure of the gas cylinder is utilized to propel liquid through the system as well. In some embodiments, an electrical pump (not shown) is utilized to propel liquid through the system. In some embodiments, the hand-held nanobubble generator is a single-use, disposable device. In other embodiments, the gas cannister is replaceable and the system can be cleaned, sterilized and loaded with new liquid.

NO Pressurized in a Liquid

In some embodiments of NO delivery, NO is stored and delivered within a liquid. As with any gas, the partial pressure of NO increases the amount of NO within a liquid (e.g., water, saline, alcohol, Ringer's solution, oil/lipid, mineral oil, blood, plasma). When the liquid is depressurized, NO comes out of solution in a gaseous form, like carbon dioxide out of a carbonated soda drink. Using this approach, the NO is not in contact with oxygen during storage and during delivery to the patient, thereby preventing the formation of $NO_2$. When delivered directly to tissue, the NO can be taken up by the tissues quickly, enabling rapid NO delivery with minimal $NO_2$ formation.

Henry's law explains the amount of gas that is dissolved in a liquid. The amount of gas dissolved is directly proportional to the partial pressure of the gas with each type of gas and liquid combination having a specific constant of proportionality, i.e., the Henry's law constant, $k_H$. For reference, $k_H$ for NO in water is $1.9 \times 10^{-5}$ mol/m$^3$ Pa, approximately $6.65 \times 10^{-5}$ mol/m$^3$ Pa for NO in alcohol, and roughly $2.47E^{-4}$ mol/m$^3$ Pa for NO in oil.

Dose delivery is modulated by varying one or more of the NO concentration within the gas, the pressure of gas, liquid temperature, the viscosity of the liquid, the quantity of liquid delivered, exposure time to the liquid, and ambient pressure at the delivery site. When high concentrations of NO are utilized, therapeutic levels of NO delivery can be achieved with very small amounts of liquid. For example, a patient breathing pulsed NO at a dose of 6 mg/hr and breathing at 12 breaths per minute receives roughly 8 μg/breath. This is equivalent to the quantity NO delivered in 0.5 ml of water-based nanobubble solution made with pure NO and delivered as an aerosol delivered at room temperature.

When the liquid is kept at a low temperature, greater amounts of NO can be dissolved. In other words, the Henry's law constant increases as temperature decreases, enabling more moles of gas to be dissolved at a given pressure. The temperature dependency on kH is ideally characterized for every gas/liquid combination. Linear interpolation of kH between discrete data points at two temperatures is acceptable for short differences in temperature.

Higher viscosity liquids and solids take longer to release NO, thereby prolonging the NO release. In some embodiments, high viscosity liquid is utilized to generate a longer NO dose delivery period for a given amount of liquid. In some embodiments, NO is dissolved in biodegradable or bioresorbable materials (e.g., poly-lactic acid) that can be implanted and release NO as they degrade over time. In some embodiments, NO-loaded material is placed in a region of the body that has low circulation (e.g., knee meniscus, Achilles' tendon, bone). Increases in in-situ NO can dilate nearby blood vessels to increase nutrient flow, spur angiogenesis, promote healing and ward off infection. In some embodiments, the degradable material is in the form of beads that can be distributed/implanted around a target region to be dosed. In some embodiments, the degradable material is in the form of a strip or an extrusion. In some embodiments, the degradable material is delivered through the bore of a syringe. In some embodiments, the degradable material is delivered by surgical implantation. In some embodiments, the degradable material is delivered by ingestion or suppository. In some embodiments, the degradable material includes an enteric coating to prevent degradation until the material has passed through the stomach. In some embodiments, the degradable material is implanted in the form of one or more of a screw, plate, bead, plug, mesh, scaffold, stent, open cell foam and disk.

Figure 33:
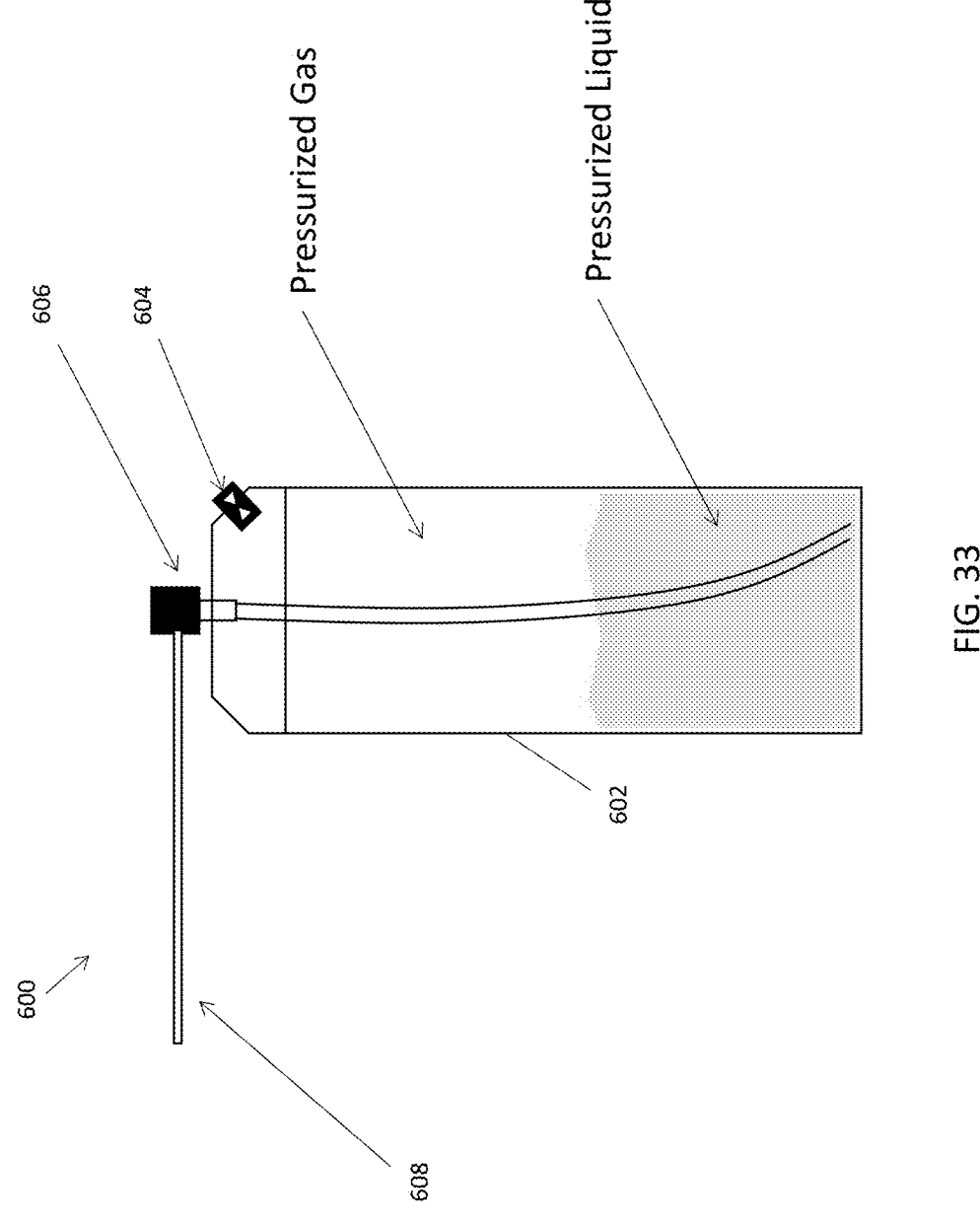
FIG. 33 depicts an embodiment of a device with a pressurized vessel for dissolved NO delivery within a liquid.

FIG. 33 depicts an embodiment of a pressurized reservoir, cannister, or vessel 600 for NO delivery within a liquid. The reservoir 600 includes a housing 602 that can withstand pressure, a fill port 604, a flow control valve 606, and a delivery device 608. In some embodiments, the delivery device can be detached from the reservoir and an array of delivery devices can be attached to the same pressurized reservoir. In some embodiments, the reservoir and/or delivery devices are single-use and disposable.

The reservoir and/or system tubing is prepared for use by flushing it with an inert gas (e.g., argon, $CO_2$, $N_2$) or non-oxygen containing gas to remove $O_2$ from inside. In some embodiments, the system is flushed with the medicinal gas (NO). In some embodiments, fluid pathways (e.g. tubing) is flushed before connecting to the reservoir. Without this step, NO within the reservoir would convert to $NO_2$ with any available oxygen. In some embodiments, the reservoir is heated before, during and/or after the flushing process to improve the release of $O_2$ from surfaces. In some embodiments, flushing is accomplished by introducing a flow of inert gas through the fill port while either continuously or periodically releasing the inert gas through the flow control valve. Completion of flushing is typically based on either a time or a gas volume measurement. In some embodiments, a vacuum is applied after flushing to decrease the amount of gas within the reservoir, thereby increasing the amount of liquid and NO-containing gas that can be introduced. Then, the reservoir is partially filled with liquid. In some embodiments, a vacuum is pulled after the liquid has been added. This is done by orienting the reservoir with respect to gravity such that the exit point is above the meniscus of the liquid to prevent escape of liquid. Applying vacuum to the liquid provides the advantage of pulling $O_2$ and other gases out of the liquid which otherwise might react with the NO. In some embodiments, the liquid is degassed or de-oxygenated prior to introduction to the reservoir. The final step involves introducing pressurized NO-containing gas to the vessel to a target pressure. In some embodiments, pure NO is used. In some embodiments, the gas includes NO and one or more inert gases (e.g., $N_2$).

In some embodiments, the housing includes a pressure gage (not shown) to indicate the pressure of contents within the reservoir. This can be helpful during filling and can indicate to a user the quantity of remaining liquid/NO. In some embodiments, the user can control the pressure within the reservoir. In these instances, the pressure gage/sensor provides feedback to the user so they can achieve a target pressure. In some embodiments, the pressure gauge is marked to indicate a maximum pressure that the pressure vessel is rated for. In some embodiments, the pressure gauge is marked with a minimum pressure required for therapeutic effect. Below the minimum pressure, there isn't sufficient dissolved gas content.

In some embodiments, the liquid is treated to remove dissolved $O_2$, $N_2$ and other gases before introduction to the reservoir. Removal of oxygen prevents formation of nitrogen dioxide within the pressure reservoir. Removal of all types of gas enables the liquid to hold a greater amount of NO. In some embodiments, dissolved gas is removed from the liquid by freezing the liquid, pumping a vacuum, then allowing the frozen liquid to melt and return to a liquid state. This step can be repeated multiple times, as needed to ensure that there are no other gases within the liquid that could interact with the nitric oxide. In some embodiments, dissolved gas is removed from a liquid by applying vacuum to the liquid. In some embodiments, vacuum is applied to one side of a gas-permeable membrane to remove gas from a liquid. In some embodiments, liquid is boiled to release dissolved gases and then cooled in a sealed container.

In some embodiments, the reservoir is flushed with non-oxygen containing gas (e.g., inert gas, medicinal gas) to remove oxygen, as before and filled with NO containing gas to a particular pressure. Then, a volume of liquid is introduced to the reservoir to bring the pressure up to the final pressure. In some embodiments, the reservoir is evacuated and then filled with liquid that already contains a target amount of dissolved NO.

Remaining oxygen within the liquid and gas headspace within the nanobubble generation system will react with the medicinal gas over time. In some embodiments (e.g., NO gas), the gas will react with any remaining oxygen in the solution. In the case of nitric oxide, reaction with oxygen forms nitrogen dioxide, which is water soluble, forming nitric acid and lowering the pH of a solution. In one embodiment the pH of a neutral liquid (e.g. saline, pH 7.2) lowers significantly to roughly 3.5 in a nanobubble generation system. To combat pH changes, a buffer can be added to the liquid. In some embodiments, the buffer selected targets a pH near that of blood, 7.4 pH. Example buffers include but are not limited to acetic acid, acetate, gluconic acid, lactic acid, tartaric acid, aspartic acid, glutamic acid, citric acid, potassium phosphate, boric acid, and citric acid cycle intermediate chemicals (e.g. isocitrate, succinate, fumarate, etc.). In some embodiments, NO nanobubbles are generated in lactated Ringer's solution, which includes alkalinizing agents that mitigate a drop in solution pH.

When the pH of a solution falls out of a target range, a nanobubble generation system can generate an alarm for the user to replace the solution. In one example, the buffer within a nanobubble solution is exhausted and the pH within the solution falls from a target rage of 6 to 8, down to 5.5. The system control generates an alarm based on the pH measurement from a pH sensor in liquid contact with the nanobubble solution.

Figure 34:
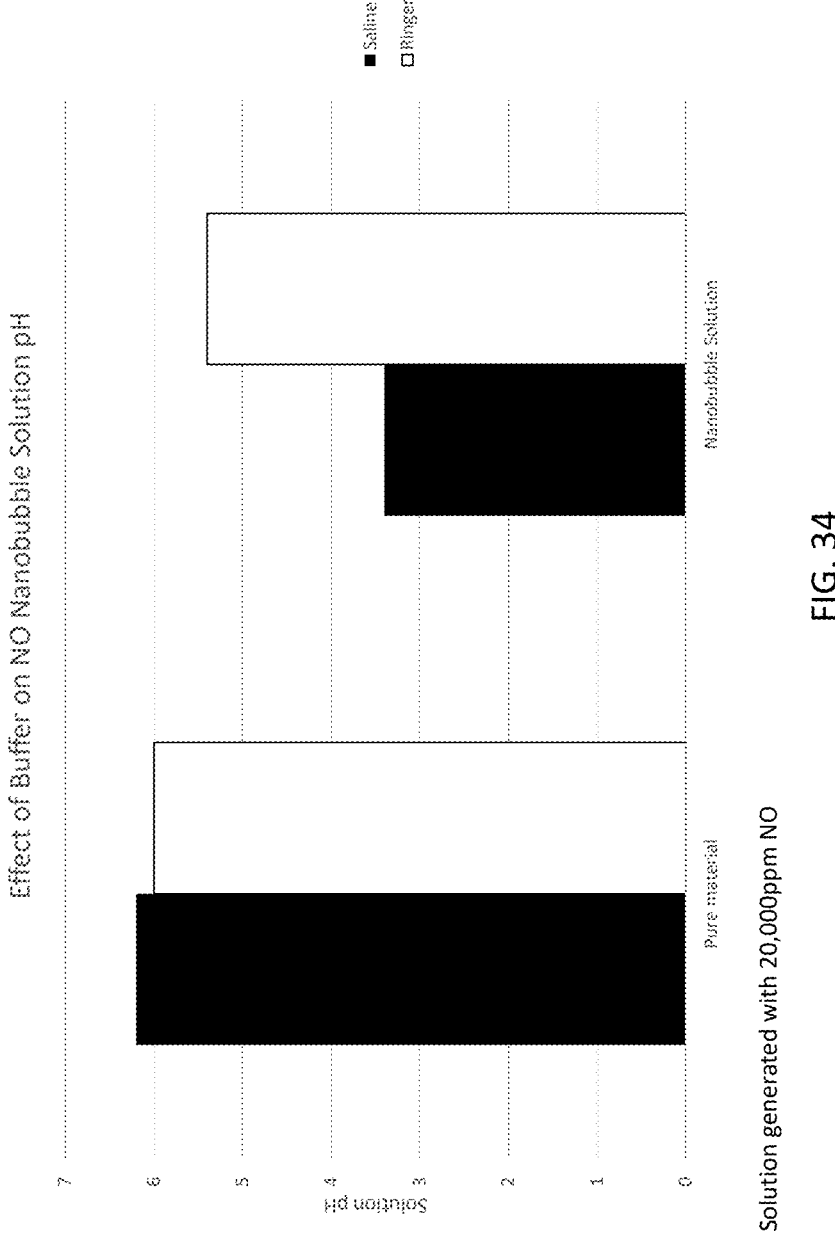
FIG. 34 depicts experimental data that show the effects of buffered solution on the pH of a NO nanobubble solution.
Figure 35:
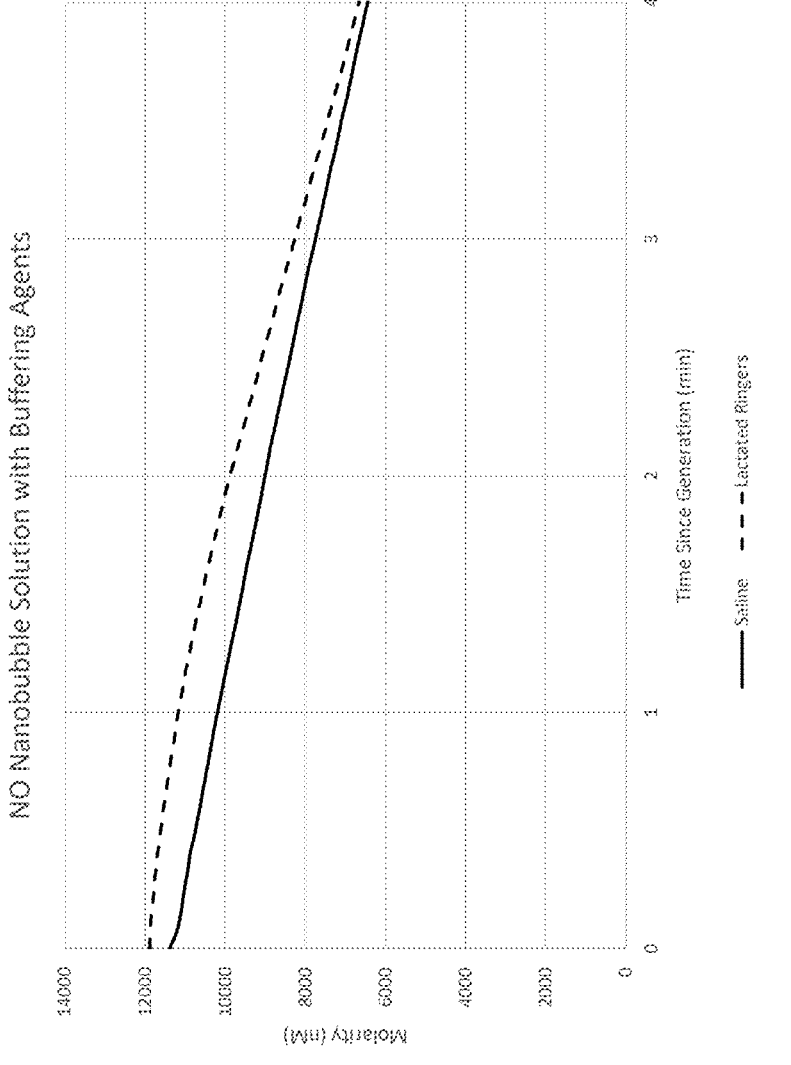
FIG. 35 shows a comparison of molarity over time for a buffered vs. non-buffered nanobubble solution.

FIG. 34 depicts an exemplary graph showing the effect of pH buffers on NO nanobubble concentration. NO nanobubbles were generated in normal saline and in lactated Ringer's solution, a solution comprised of saline, sodium lactate and electrolytes. The initial pH of the saline and lactated Ringer's solution was 6.2 and 6, respectively. After nanobubble generation, the pH of the saline and the lactated Ringer's solution were 3.4 and 5.4, respectively. The pH decreased 45% for the saline solution, but only 10% for the lactated Ringer's solution. FIG. 35 depicts an exemplary graph showing the NO molarity for the same saline and lactated Ringer's solution samples. The higher molarity exhibited by the lactated Ringer's solution may be related to one or more of the increased viscosity of the solution, the electrolyte effects on bubble charge. Hence, a nanobubble solution can be buffered to achieve a more physiologically compatible pH, as needed, while still achieving clinically relevant NO molarity.

In some embodiments, the delivery device consists of one or more of a needle, a catheter, a cannula, a trocar, a tube, a nasal prong, a mister, a spray nozzle, a squeeze bottle, an endoscope, a laparoscope, a colonoscope, a dropper, a nebulizer, and other liquid delivery and/or liquid-handling devices.

In an exemplary application, NO is pressurized within a liquid and delivered to the nasal cavity via an elongated spray nozzle. When the NO-containing liquid is delivered to the cavity, dissolved NO gas releases from the liquid, displacing other gas within the nasal cavity. In some embodiments, the user inhales during or after NO introduction to deliver the NO deeper within the airway and/or lungs. In some embodiments, the user refrains from inhaling or exhaling for a period of time (e.g., 15 sec), enabling the NO gas to treat the nasal cavity. This can be particularly effective in treating infections when high concentrations of NO are used (e.g., >150 ppm NO). In some embodiments, the user squeezes their nostrils around the delivery device to prevent loss of NO to the environment and prolong the dose. In some embodiments, a clip is used on the nostrils to hold them closed.

In some embodiments, the flow control valve is controlled by a mechanical or electronic and/or software-driven controller to produce specific flow rates and durations of NO-loaded liquid flow to a target area. The amount of liquid delivered is modulated by the degree of opening of the flow control valve and the duration of opening. In some embodiments, an electronic circuit opens a flow control valve in response to a trigger signal (e.g., closing of a switch) and holds a flow control valve open until a target change in pressure, as indicated by a pressure sensor, occurred in the vessel that corresponds with a target liquid volume change within the vessel.

In some embodiments, the quantity of NO delivered in a particular bolus is measured in moles of NO. A collection of boluses can be delivered to satisfy a dosing schedule, for example NO delivery in mgNO/hr or mgNO/hr/ideal body weight. The amount of gaseous drug (e.g. NO) delivered to achieve a specific dose can be a function of one or more of liquid type (i.e., Henry's constant), liquid volume delivered, NO concentration within the gas, pressure within the vessel, duration of exposure, permeability of target tissue, surface area treated, and target dose. In some applications, a minimum concentration is required for therapeutic effect (e.g. antibacterial effects require concentrations that exceed a minimum threshold). In some embodiments, a NO delivery device measures the amount of NO delivered by a change in pressure within the reservoir, based on the known volume of the reservoir and known volume of liquid within the reservoir. In some embodiments, a flow sensor measures the flow of liquid from the reservoir. In some embodiments, the flow rate of liquid is integrated over time to obtain a liquid volume. In some embodiments, a conductive strip on the side of the reservoir measures the level of the liquid meniscus in one or more locations. In some embodiments, an ultrasonic sensor detects the elevation of the liquid level within the cannister when the cannister is held in a specific orientation. In some embodiments, one or more load sensors in the handle of the device indicate the remaining mass of the delivery system, which is indicative of the remaining volume of liquid.

As the pressure within the vessel decreases, the partial pressure of NO gas acting on the liquid decreases resulting in lower NO content within the liquid. In some embodiments, the controller compensates for lower dissolved NO within the liquid by delivering more liquid so that a target number of moles of NO can be delivered.

As the pressure within a liquid-filled NO delivery device falls, larger amounts of liquid are required to deliver a target dose of NO. Eventually, the amount of liquid within the reservoir is exhausted or the amount of liquid required to be delivered for a therapeutic dose exceeds an acceptable volume. In some embodiments, a NO-laden liquid delivery device actively prevents further use when this threshold is reached. In some embodiments, a NO-laden liquid delivery device generates a visual, audible, and/or tactile alarm to indicate to a user that the device is at or near the end of its service life. This alarm threshold can vary with the amount of NO to be delivered.

Figure 36:
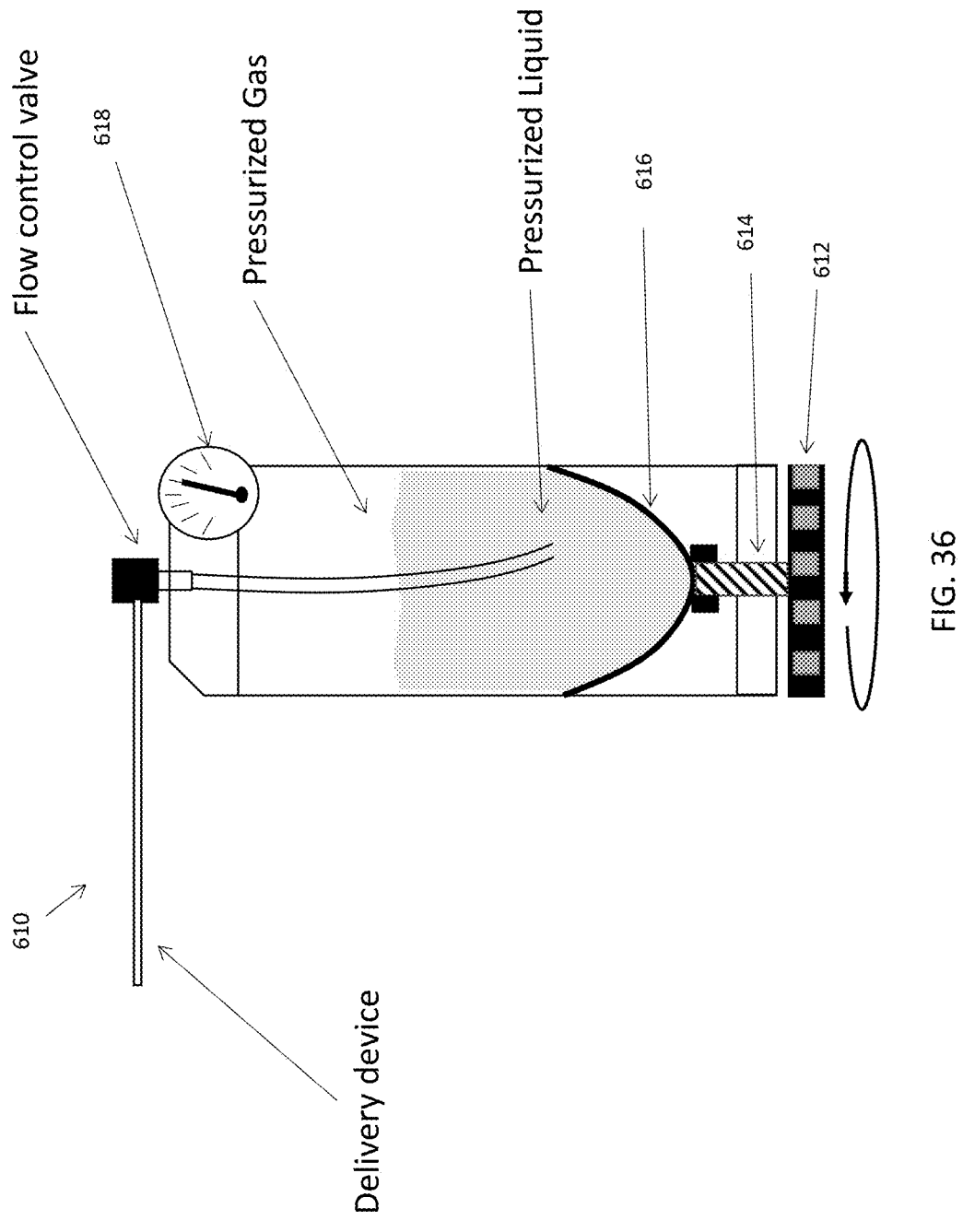
FIG. 36 depicts an embodiment of a device for NO delivery within a liquid that enables a user to achieve a target pressure prior to NO delivery.

In some embodiments, the volume within the reservoir is reduced to maintain high pressure on the liquid. FIG. 36 depicts an embodiment of a reservoir 610 that enables a user to achieve a target pressure prior to NO delivery. A knob 612 at the bottom of the reservoir is attached to a threaded rod or shaft 614. As the knob is turned, the threaded rod presses against a diaphragm 616 that compresses the liquid and gas within the reservoir. A pressure gauge 618 on the exterior of the device indicates the pressure within the reservoir. The concentration of NO within the liquid remains constant so long as the pressure within the reservoir remains constant.

Some embodiments use pistons or other features that take up volume within the reservoir, thereby increasing the pressure. In some embodiments, the pressure is passively maintained by a spring (e.g., compressed or in tension) acting on the diaphragm. In some embodiments, the process of maintaining a target pressure within the reservoir is automated by a controller that adjusts the position of a volume-displacement feature based on feedback from a reservoir pressure sensor. In some embodiments, a motor turns a threaded shaft that presses upon a diaphragm, for example.

In some embodiments, the target pressure within a NO-laden liquid reservoir is selected to achieve a specific partial pressure of NO on the liquid surface which, in-turn, produces a known amount of NO dissolved within the liquid for a given concentration of NO gas. This enables NO dose delivery to simply be a function of liquid volume delivered. In one exemplary embodiment, a device targets a pressure within the reservoir containing NO gas and a liquid. After delivery of a bolus of NO-laden liquid, the pressure in the reservoir will decrease, which will be indicated by a pressure sensor in fluid communication with the reservoir. The device automatically decreases the volume of the reservoir based on feedback from the pressures sensor to restore the pressure on the liquid to the target level. For example, a 1000 cc reservoir contains 500 cc of water and 500 cc of 1000 ppm NO pressurized to 1000 kPa (roughly 10 atmospheres). Delivery of 1 ml of water delivers 570 µg of NO. When 1 ml of water is delivered, the volume of gas increases to 501 cc. Using Boyle's law (i.e. P1V1=P2V2), the pressure within the reservoir decreases to 998 kPa and the amount of NO dissolved decreases to 569 µg of NO per ml. If the system decreases the volume of the chamber by the amount of water released, the original pressure within the reservoir (1000 kPa) will be retained and the amount of NO within the liquid will remain constant.

In some embodiments, the reservoir volume is altered after every bolus of liquid delivered. In some embodiments, the reservoir volume is altered every nth bolus of liquid since the changes in NO loading within the liquid can be slight.

In some embodiments, elevated pressure is only applied to the liquid and gas within the reservoir at the time of NO delivery. At other times, the reservoir is maintained at a lower pressure to increase safety and decrease strain on device components (e.g., seals, valves, diaphragms).

In some embodiments, the device is programmed to permit NO delivery by a user according to a particular dosing schedule. In some embodiments, the device reminds a user when it is time to deliver the next dose of NO. For example, a device can be programmed to deliver a dose equivalent to 400 ppm of NO within a patient's nose every hour. In some embodiments, the NO dose delivered is calculated as a function of the concentration of NO gas in the reservoir, the pressure in the reservoir, the volume of liquid delivered and the measured/inferred/assumed cavity volume.

Figure 37:
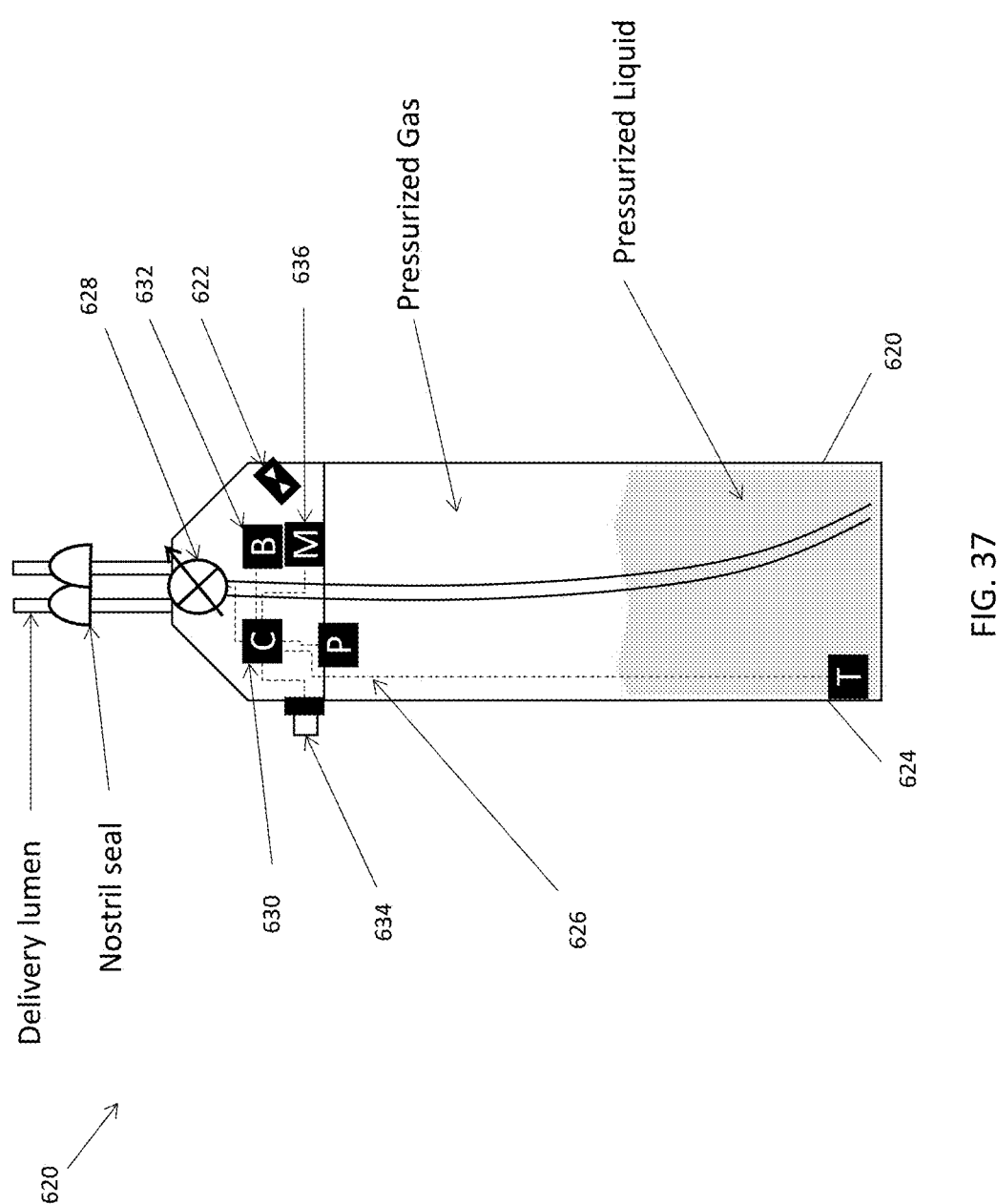
FIG. 37 depicts an exemplary embodiment of a software-controlled, electro-mechanical NO-laden liquid delivery device.

FIG. 37 depicts another exemplary embodiment of a NO-laden liquid delivery device. Liquid and gas are introduced to a reservoir 620 through a fill port 622. Temperature and pressure of the liquid within the device are measured by sensors 624, 626. The flow of pressurized liquid out of the reservoir is controlled by a flow controller 628 (e.g., proportional valve). The flow controller is controlled by a controller 630 (e.g., microprocessor) that is powered by a battery 632. A trigger sensor 634 (e.g., button) notifies the controller when to initiate liquid delivery. The controller is also connected to a memory device 636 for storing one or more of prescriptions, gas concentration, expiration date, manufacturing/loading date, planned dosing schedules, actual dosing schedules, alarm conditions, patient information, reservoir history (e.g., number of pressure cycles if reused) and other relevant information.

As shown in FIG. 37, a delivery device can include two lumens that are inserted into each nostril. The delivery device is inserted to a level that the sealing features press into the nostril and seal around the periphery. In some embodiments, the sealing features are stiff, hemispherical shapes. In some embodiments, the sealing features are a soft compliant feature. In some embodiments, the delivery device includes a mask (e.g., nose-cover, nose and mouth cover, or face cover).

Figure 38:
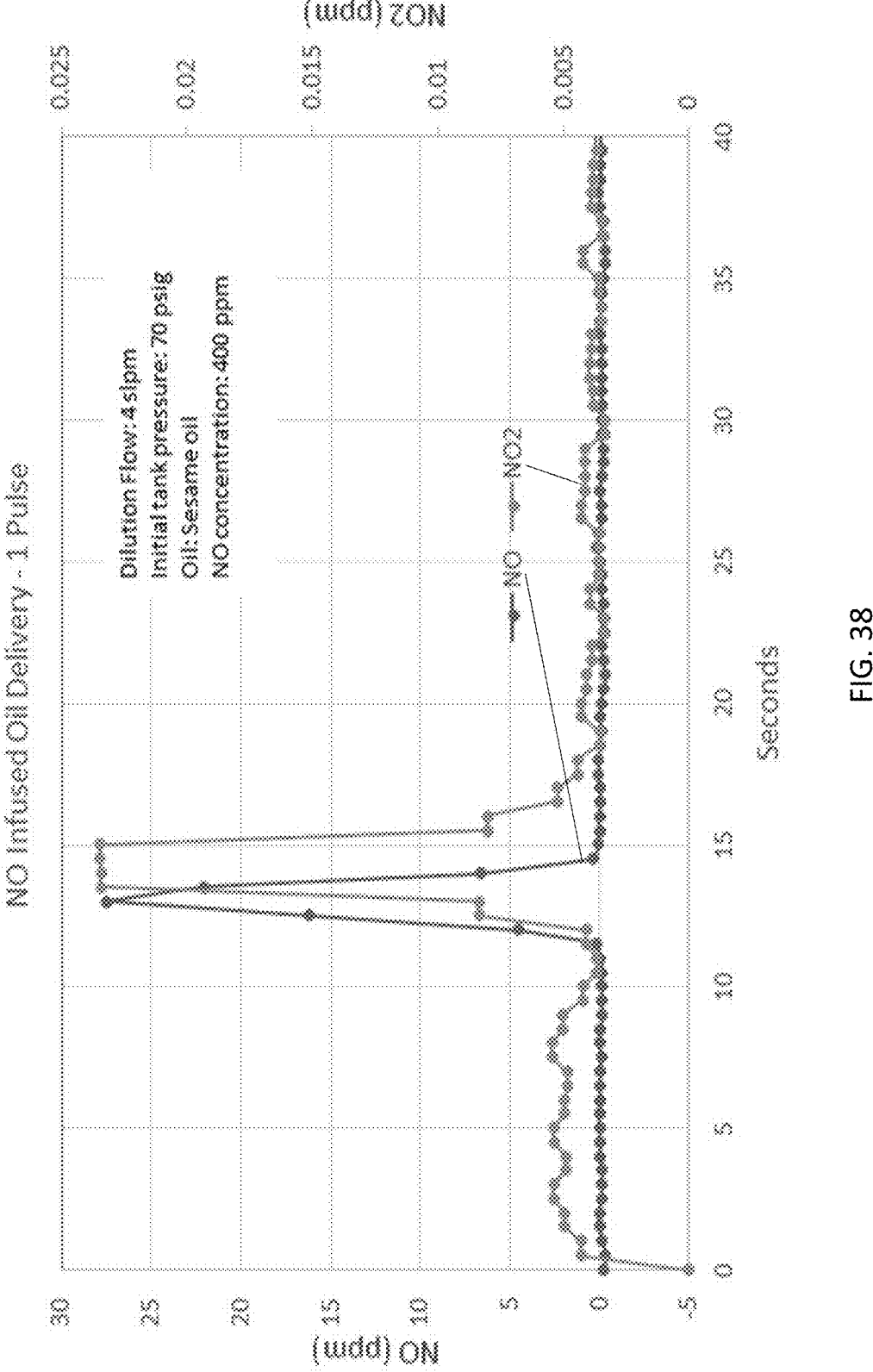
FIG. 38 illustrates an exemplary graph showing exemplary experimental data that demonstrates delivery of NO from a liquid.

FIG. 38 illustrates an exemplary graph showing exemplary experimental data that demonstrates delivery of NO from a liquid. In the example, sesame oil was introduced to a reservoir. The reservoir was then purged with nitrogen. The reservoir was then pressurized with 400 ppm NO in a balance of $N_2$ to 60 psi. A roughly 1-second-long pulse of oil/NO was introduced to a 5 lpm air flow. Gas measurements were made with a chemiluminescent analyzer for NO and IR spectroscopy for $NO_2$ downstream of the injection point. This exemplary graph demonstrates that the NO remained viable within the oil and was effectively delivered at a diluted concentration of 27 ppm with 23 ppb of $NO_2$.

Figure 39:
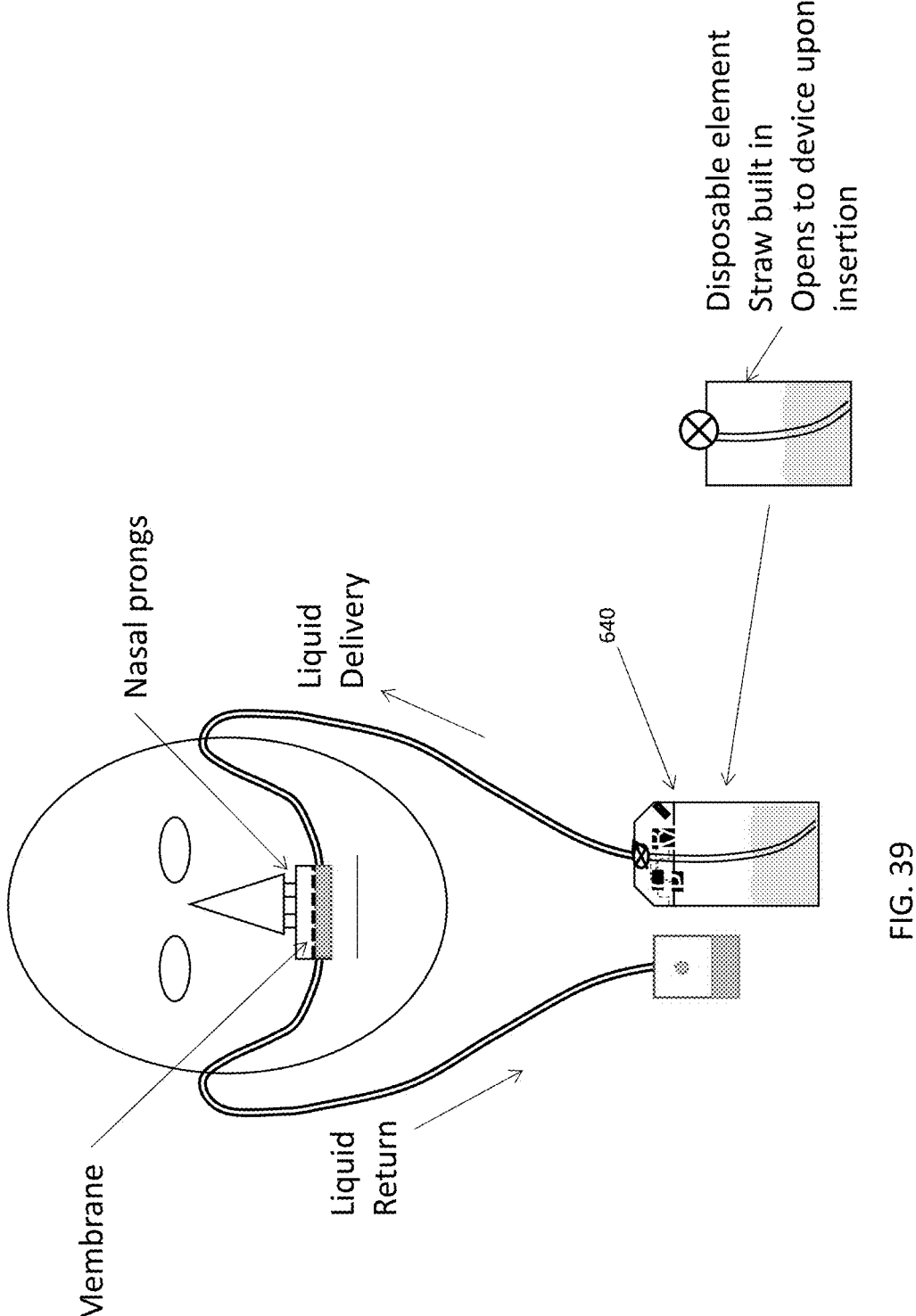
FIG. 39 depicts an embodiment of a device that utilizes a pressurized cannister of NO and a liquid.

In some embodiments, the delivery device releases the NO into a proximal reservoir that separates out NO from a liquid, delivers NO to a patient and collects spent liquid. FIG. 39 depicts an embodiment of a device that utilizes a pressurized cannister 640 of NO and a liquid. The pressurized cannister is removable and replaceable. The device releases liquid from the cannister either continuously or in pulses to a delivery device. In the depicted embodiment, flow of the liquid is propelled by the pressure in the cannister. In some embodiments, the device includes a mechanism to maintain a target pressure within the cannister despite the loss of liquid volume in order to maintain the same gas partial pressure. In some embodiments, a pump propels liquid through the system. In some embodiments involving a pump, the pump delivers liquid at a faster rate as the pressure within the cannister decreases to maintain a target delivery rate of NO to the patient.

The delivery device depicted is an exemplary cannula with two nasal prongs. The nasal prong assembly includes a chamber divided into two portions that are separated by a gas-permeable membrane. As liquid enters the lower chamber, NO-containing gas evaporates out for inhalation into the patient through the nasal prongs. The liquid continues to flow to a container, where it is collected.

In some embodiments (not shown), liquid containing NO is passed through a gas exchanger in an ECMO system. Dissolved NO within the liquid crosses a membrane in the gas exchanger to enter patient blood that circulating extracorporeally.

Figure 40:
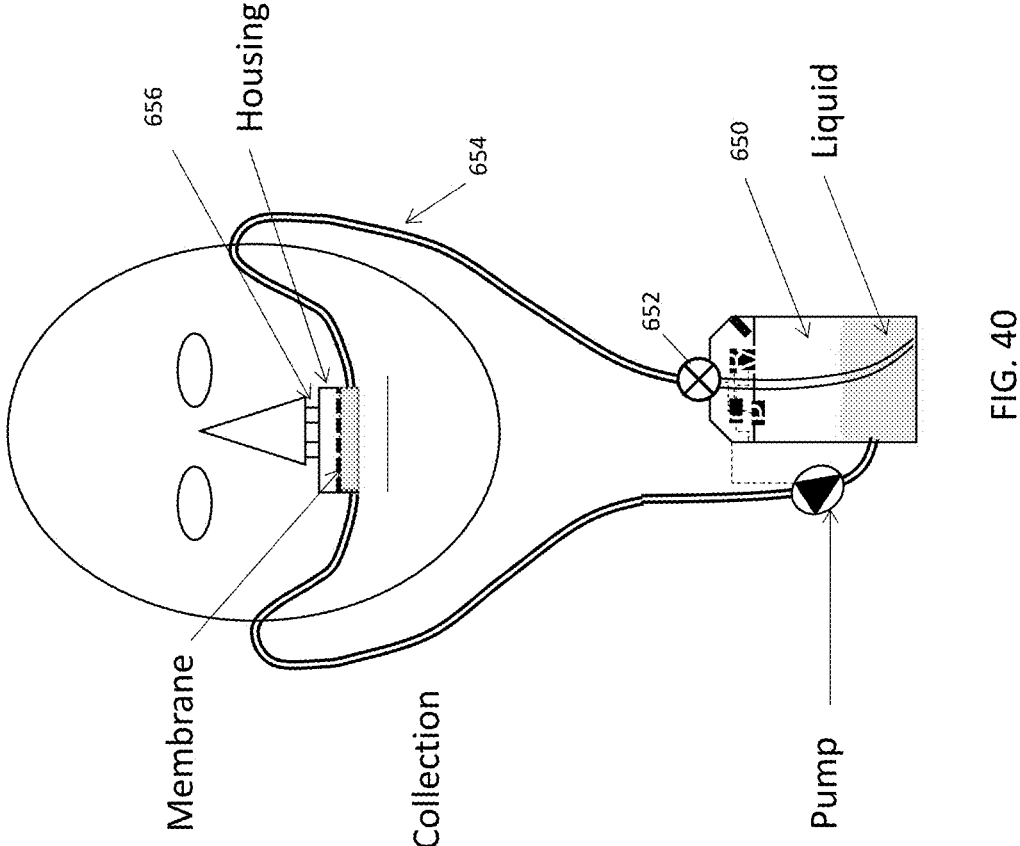
FIG. 40 depicts an exemplary system that utilizes a liquid in a closed loop to deliver NO to a patient.

FIG. 40 depicts another exemplary system that utilizes a liquid to deliver NO to a patient. NO gas and a liquid are located in a pressurized cannister 650. A flow controller 652 at the exit (top) of the cannister regulates the flow of NO-containing liquid through a delivery device 654. As liquid enters the nasal prong assembly 656, NO gas is exposed to ambient pressure, comes out of solution and is inhaled by the patient. The liquid continues to flow back down to the cannister. A pump pressurizes the liquid to maintain pressure within the cannister. This approach enables longer cannister use because the liquid is utilized multiple times and the only volume change occurring within the cannister is from loss of NO.

Figure 41:
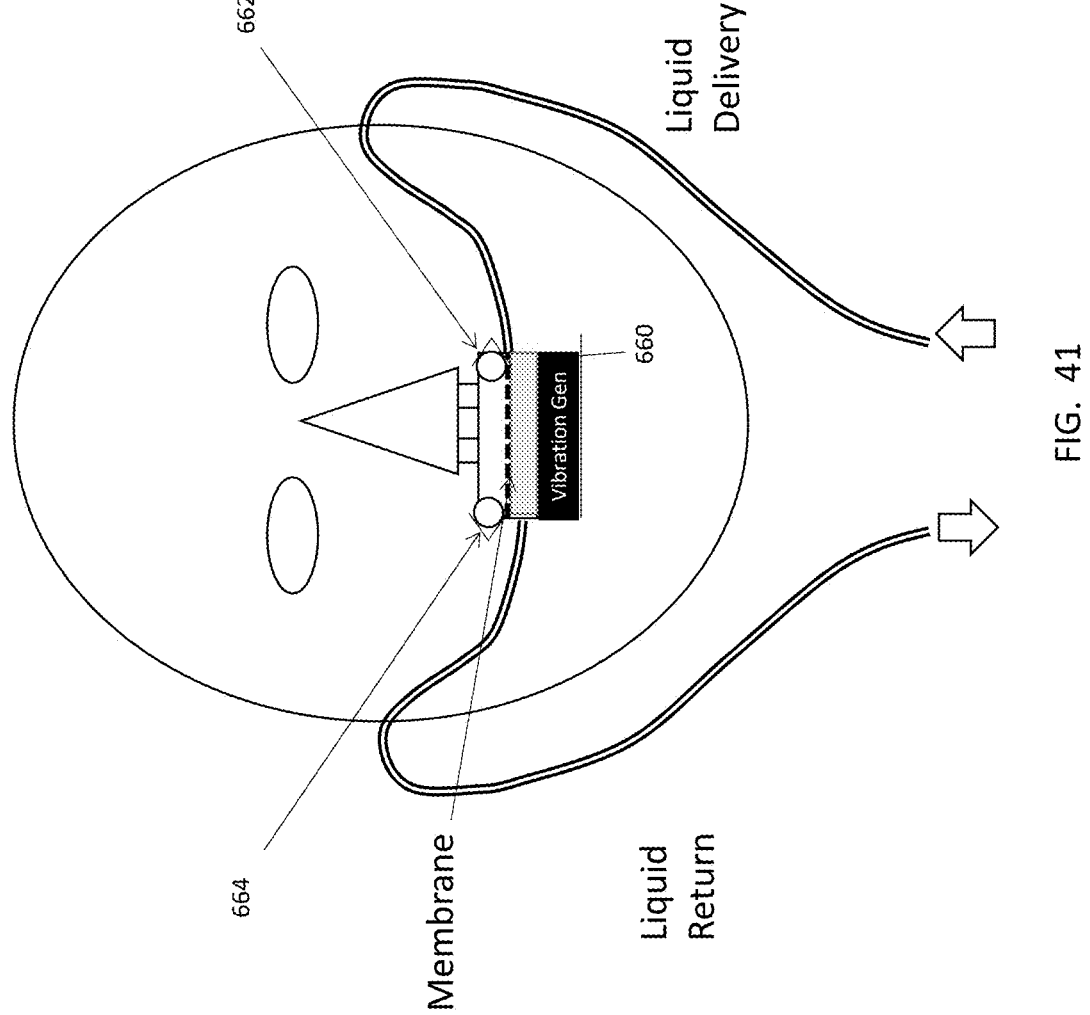
FIG. 41 depicts an embodiment of a delivery device that utilizes ultrasound to drive bubbles toward the membrane for more rapid and complete NO release.

FIG. 41 depicts a delivery device that utilizes a vibration generator 660 to drive bubbles toward the membrane for more rapid NO release. The vibration generator can be powered by battery or through wires in the delivery device. In some embodiments, the vibrations imparted to the liquid are in the ultrasound frequency range (>20 kHz). In some embodiments, a piezo actuator is utilized to induce motion in the liquid towards the membrane for more efficient release. This approach of utilizing ultrasound can operate down to the microbubble or nanobubble level to enhance the release of gas out of a liquid.

Another feature depicted in FIG. 41 is one-way valves, or check valves 662, 664 in the nasal prong assembly. As the patient inhales, air enters the patient from around the nasal prongs and through the nasal prongs. Air entering the patient through the prong passes over the NO release membrane, picking up NO. The check valves permit air to flow through the nasal prongs to pick up NO-containing gas crossing the membrane and deliver it to the patient more quickly, thereby shortening the NO delivery time and oxidation time.

In some embodiments, a heater is utilized to promote gas release from the liquid. In some embodiments, a resistive heater is located in the gas release zone. As gas-laded liquid enters the release zone, the temperature of the liquid increases, decreasing its ability to retain dissolved gases. In some embodiments, a temperature sensor (e.g., thermistor or thermocouple) is used to provide feedback to a temperature controller that maintains optimal temperature and temperature below safety thresholds (i.e., to prevent thermal damage to the patient).

In some embodiments, gas release from a nanobubble solution is hastened by application of external energy. In some embodiments, an increase in temperature, passively (e.g. warming to body temperature) or actively (e.g. infrared heat) hastens the release of gas from a nanobubble solution. In some embodiments, nanobubbles are stimulated with infrared light. Infrared light can permeate several centimeters into the body to release NO from nanobubbles non-invasively.

In some embodiments, ultrasonic energy is applied to a nanobubble solution to release gas from the solution. In some embodiments, nanobubbles are stimulated by ultrasound to burst the bubbles and release the gas at a targeted location. In some embodiments, liquid containing NO nanobubbles is introduced to a region of the body (e.g., a tumor). Then, the nanobubbles are stimulated with ultrasound. The ultrasound can be externally applied (e.g., to the skin) or internally applied (e.g., from the esophagus, intestine, or an incision). Greater amounts of ultrasound can be imparted to the bubbles when the ultrasound source is as close as possible. The ultrasonic energy applied to the bubbles promotes bubble rupture and permeation of the gas (NO) into cells and surrounding tissues. Application of ultrasound can assist in targeting specific tissues and/or organs for treatment with NO.

In some embodiments, microwave energy is applied to the nanobubble solution to hasten the release of gas form the solution.

Figure 42:
FIG. 42 depicts an embodiment of a liquid NO delivery device with flow control at the patient.

FIG. 42 depicts an exemplary embodiment of a liquid NO delivery device 670 with flow control at the patient. A compact assembly of a breath detection sensor 672 (e.g., pressure sensor, flow sensor, microphone, temperature sensor), processor or controller 674, battery 676, memory, and flow control valve 678 are located near the point of delivery. In some applications, the device is located at the patient's ear, rather than at the nose. In some embodiments, an additional lumen within the delivery device enables remote detection of patient respiratory events from a sensor within the main NO device. The flow control device depicted permits the flow of NO-containing liquid upon detection of breath. This design allows for the pressurized liquid to be located adjacent to the location of delivery, thereby improving the response time and accuracy of NO delivery. In some embodiments, NO is sourced from an electrical generator. This form of generation often generates a quantity of $NO_2$ as well. Given that $NO_2$ is soluble in water, turning into nitric acid, when water is utilized as the liquid carrier, the $NO_2$ remains in solution and the NO is released.

It will be understood that any embodiments shown using a nasal cannula as a delivery device such that the gas is released into a nasal prong can also use various other forms of delivery devices, including but not limited to a mask, an inspiratory limb, ECMO gas exchanger module, and a topical application.

Figures 43A, 43B, 43C:
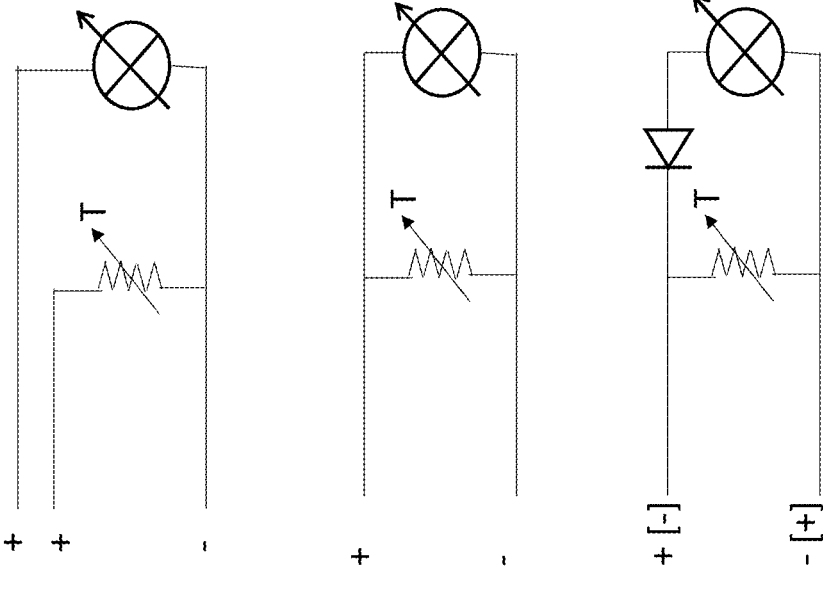
FIG. 43A depicts an embodiment of a 3-wire approach where the breath detection sensor (a thermistor in this case) and the flow control valve have separate power lines and a common ground line.
FIG. 43B depicts an embodiment of a two-wire design that powers a thermistor for breath detection and a flow controller for NO-laden liquid.
FIG. 43C depicts an embodiment of a 2-wire approach with reversing polarity to achieve breath detection and flow control.

FIGS. 43A, 43B and 43C depict exemplary embodiments of circuits for powering a remote device that detects breath and manages liquid flow control. These approaches can be utilized with AC or DC voltage. The remote device can be small and does not require a battery. In some embodiments, wires are routed through or adjacent to lumens within the delivery device. In some embodiments, wires are insulated with varnish or silicone to be very thin in cross-section. FIG. 43A depicts a 3-wire approach where the breath detection sensor (a thermistor in this case) and the flow control valve have separate power lines and a common ground line. FIG. 43B depicts a two-wire design where a thermistor is used to detect breath when it starts to cool down from the heating of exhalation. A low voltage is initially applied to the thermistor to monitor for breath detection. When the liquid NO delivery system determines to deliver NO, the voltage applied is increased to the level required to actuate the valve. The thermistor resistance is high enough that it doesn't affect the ability to deliver power to the valve. FIG. 43C depicts another 2-wire approach to achieve remote breath detection and flow control. Voltage is applied in a first polarity to monitor a breath detection sensor. When the device initiates NO delivery, it reverses the polarity of the voltage on the 2 wires and applies adequate voltage to actuate the flow controller. A diode on the leg of the flow controller prevents electrical current from flowing through the flow controller during breath detection monitoring. After NO delivery, the device reverses the voltage polarity and lowers the voltage (as needed) to resume monitoring for respiratory events.

Figure 44:
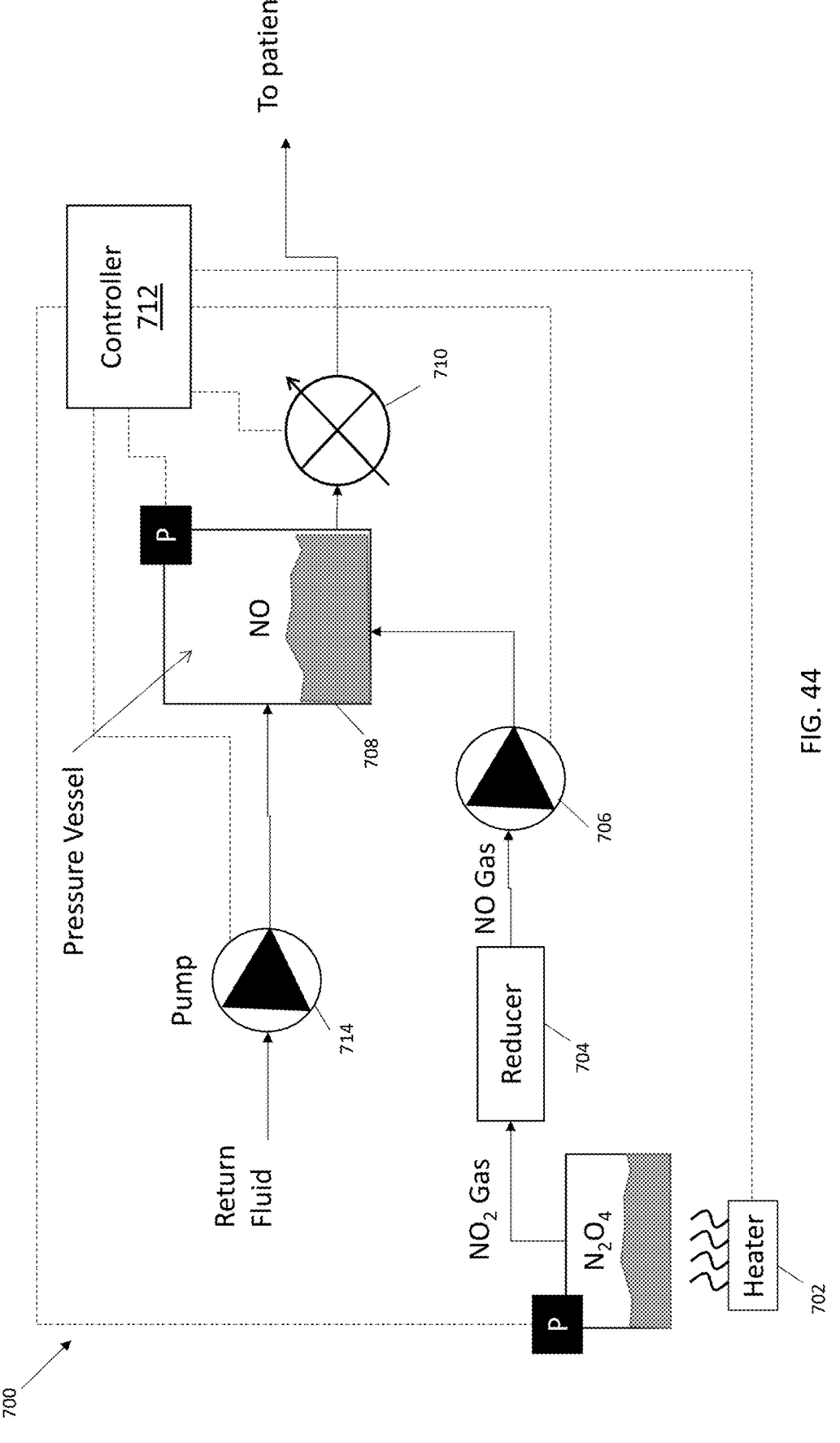
FIG. 44 depicts an embodiment of a combination NO generator and nanobubble generator.

FIG. 44 depicts an embodiment of a combination NO generator and nanobubble generator 700. In this example, NO is sourced from a system that variably heats $N_2O_4$ using a heater 702 to create $NO_2$. The $NO_2$ passes through a reducer 704 that removes oxygen from the $NO_2$, forming NO. The NO is delivered by a pump 706 to a pressure vessel 708, where it dissolves into the liquid according to Henry's law. A flow controller 710 regulates the flow of NO-containing liquid to the patient. A controller 712 manages the operation of the device based on a pressure measurement in the $N_2O_4$ chamber and pressure within the liquid pressure chamber. The controller 712 modulates the temperature of the $N_2O_4$ to maintain a target pressure within the $N_2O_4$ chamber. The controller 712 modulates the pump speed to maintain a target pressure within the pressure chamber. The controller 712 modulates the flow controller to deliver a target dose profile to the patient. In some embodiments, liquid returns from the patient for reuse. A return liquid pump 714, also under the direction of the controller, directs returned liquid and/or fresh liquid to the pressure chamber 708. In some embodiments, the returned liquid is filtered for particulate and scrubbed of NO (e.g., activated carbon filter) before reuse.

Figure 45:
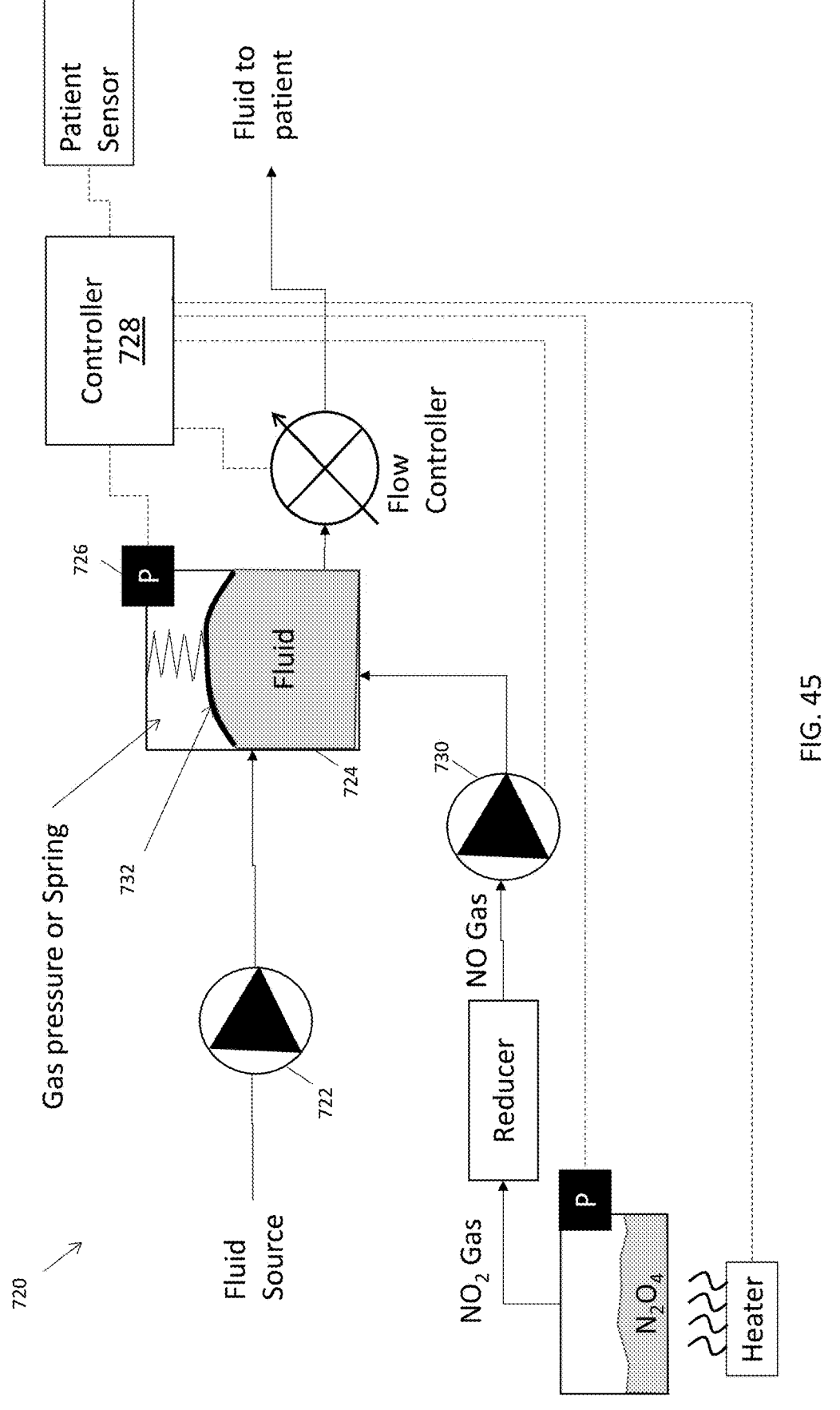
FIG. 45 depicts an embodiment of a NO-containing liquid device with a diaphragm that maintains pressure on liquid.

FIG. 45 depicts another embodiment of a NO-containing liquid device in a NO generator and nanobubble generator 720. Fresh liquid is sourced and flows through a pump 722 into a pressure reservoir 724. The pressure within the reservoir is measured with a pressure sensor 726 in fluid communication with the reservoir and electrical or wireless communication with the controller 728. A second pump 730 pressurizes NO from an NO source for it to dissolve in the liquid. A diaphragm 732 within the pressure chamber is utilized to maintain constant pressure and minimize pressure spikes resulting from pump pulsatility. In some embodiments, the diaphragm is spring-actuated. In some embodiments, the diaphragm has high pressure gas on one side to push against the liquid and maintain a high pressure. In some embodiments, the diaphragm is gas permeable (not shown), allowing excess gas to escape through the diaphragm and exit the system. In some embodiments, escaped gas is one or more of scrubbed, collected, or reused (i.e. pumped up to pressure and reintroduced through the nanobubble generator). In some embodiments, the high-pressure gas is sourced from a pump. In some embodiments, a rolling diaphragm is utilized with a piston. In some embodiments, high pressure gas above the diaphragm is provided by a compressed gas (e.g. $CO_2$) cylinder that contains liquid gas so that the pressure remains consistent over a longer period of time until all of the liquid has evaporated. Either one or both of the pumps is controlled to maintain a pressure level in the liquid pressure reservoir in order to maintain a specific partial pressure of NO within the liquid. The controller monitors a parameter at the patient (e.g., inspiratory pressure) to determine when to deliver NO through the flow controller.

Clinical Applications

NO delivered as a dissolved gas or nanobubble can applied to a myriad of clinical indications ranging from cancer to infections.

Cancer Treatment

In cancer, NO can alter the tumor micro-environment (TME) and polarization of tumor associated macrophages (TAMs). TAMs can be a barrier to nanoparticle drug delivery because their role in physiology is to collect nanoparticles. Nanoparticle drugs collected by TAMs never reach the target cancerous tissue. It has been demonstrated that increasing NO concentration within the tumor switches the polarization of the TAMS and makes them attack cancerous tissue. In addition, the presence of elevated levels of NO will increase vasodilation to convey more drug to the tumor in addition to switching TAMs. For drugs that place antigens on the cancerous cells to target them for destruction by the immune system, this could improve the efficacy of current treatments.

Another aspect to NO treatment relates to NO's ability to promote blood vessel growth (i.e., angiogenesis). Tumors can have a very low level of interstitial NO within them. This turns off TAMs and can result in atypical blood vessel pathways. Elevating local NO levels within the tumor with NO nanobubbles has the potential to restore typical physiologic NO levels which will promote more healthy blood vessel patterns. This will improve the distribution of other drugs within the cancerous tissue (e.g., chemotherapy and immune-response modifying drugs).

In cancer treatment, NO nanobubbles can be delivered systemically by ingestion, IV, and/or injection. The NO-containing liquid can be used to treat solid tumors, melanoma, lung cancer and more. In some embodiments, nanobubble NO is delivered (either locally or systemically) during a systemic treatment (e.g., chemotherapy) to increase circulation of systemic drugs (e.g., chemotherapy drugs) within the lung. In some embodiments, NO nanobubble solution is delivered to the pulmonary artery to expose lung tissue to elevated NO levels. This approach can be used to treat ailments of the lung (e.g., mesothelioma, NSCLC). In some embodiments, local delivery is preferred to systemic delivery because there is greater control of medicinal gas concentration at the target tissue and less risk of systemic side effects and medicine loss.

In some embodiments, NO is introduced to the bowel as a nanobubble in a liquid that is used to flush the intestines of a patient. The NO acts on the smooth muscle within the blood vessel walls with the intestine, making the smooth muscles relax. This increases blood flow through the intestines, helping ensure circulation of systemic drugs to the intestinal cancers.

Additional types of cancerous tumor that can be treated with NO nanobubbles include but are not limited to cancers of the breast, brain, nerves, uterus, colon, rectum, skin, liver, lymph nodes, thyroid, bones, prostate, ovary, pancreas, stomach, mouth, throat and lung. In another application, NO nanobubble solution is utilized to treat non-cancerous tumors, hyperplasia, intrauterine fibroids, benign prostatic hyperplasia (BPH), lipomas, and hemangiomas.

In another embodiment, cancerous tissue is exposed via injection or intravascularly to NO nanobubble solution. The solution increases local NO concentration within the cancer. The elevated NO concentration increases sensitivity of the cancer cells to ionizing radiation, as utilized during radiation therapy.

Figure 46:
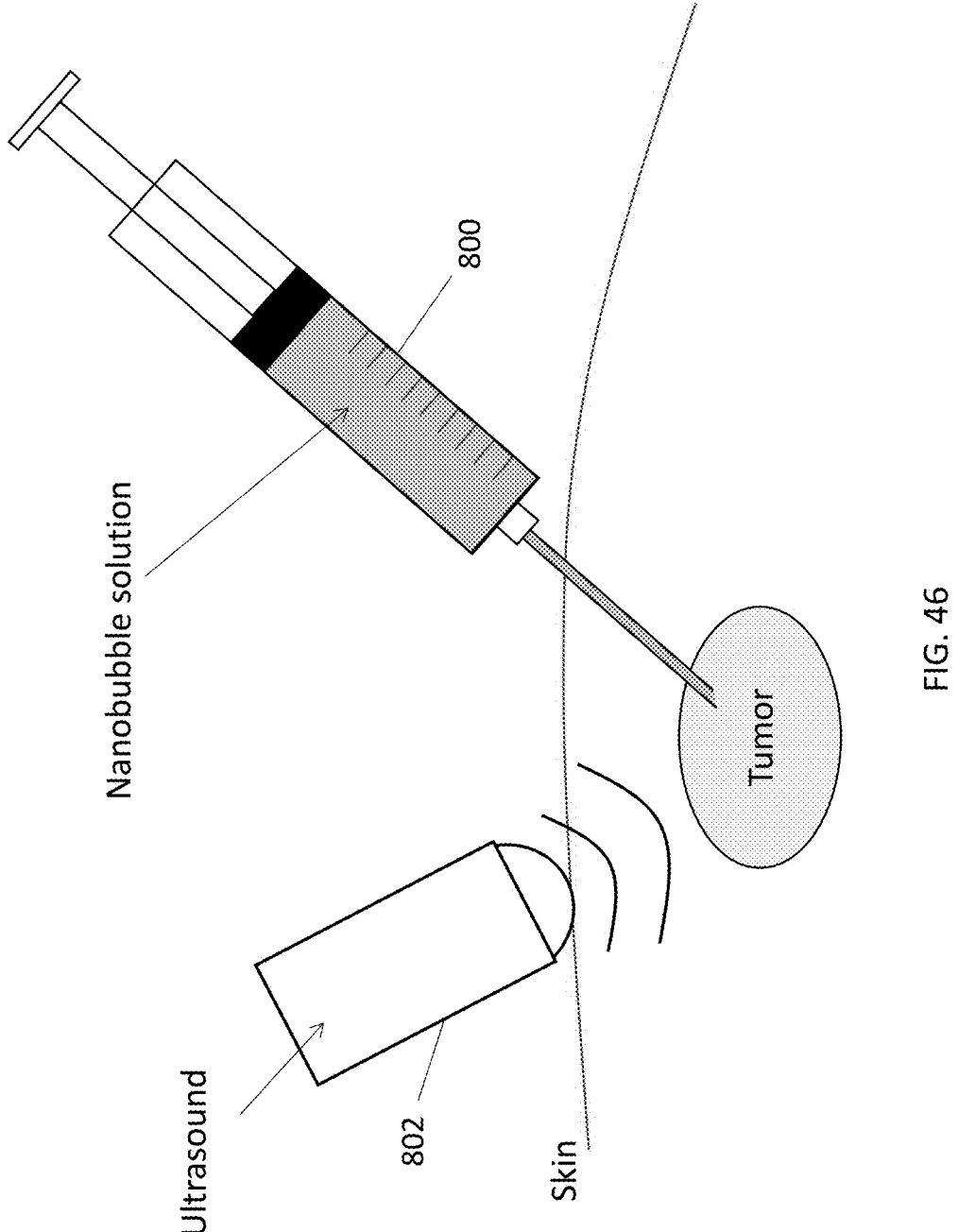
FIG. 46 depicts an exemplary treatment of a solid organ tumor with NO nanobubbles.

FIG. 46 depicts an exemplary treatment of a solid organ tumor with NO nanobubbles. Nanobubble solution is loaded within a syringe 800 or other delivery device. The syringe is inserted into a target tissue (e.g., tumor, muscle, etc.). In some methods, the syringe is aspirated (handle pulled back) to ensure that the tip is not in a blood vessel) before introduction of nanobubble solution. This can ensure delivery of the solution to the interstitial space within tissue. In some applications, nanobubble solution is introduced to the blood flow upstream of a tumor to distribute NO throughout the tumor.

In this example, ultrasound is utilized using an ultrasound device 802 to locate a tumor and provide visual guidance for placing one or more needles into the tumor for nanobubble solution delivery. An optional filter at the exit of the syringe can ensure sterility of the nanobubble solution as it is delivered. Injected nanobubbles can serve as contrast in the ultrasound imaging to enable viewing of the treated tissues. As explained above, the ultrasound can also be used to burst the nanobubbles to release the gas at the target location.

In some embodiments, MRI is utilized to track the location of NO-containing nanobubble solution. In some embodiments, an MRI contrast solution (e.g. gadolinium) is loaded with nanobubbles. The contrast solution is introduced to the patient (e.g. orally, intravascular, interstitially) and the location of the contrast is tracked with an MRI system. The MRI enables the clinicians to visualize and identify the tissues and regions that are receiving treatment from the injected nanobubble solution.

Figure 47:
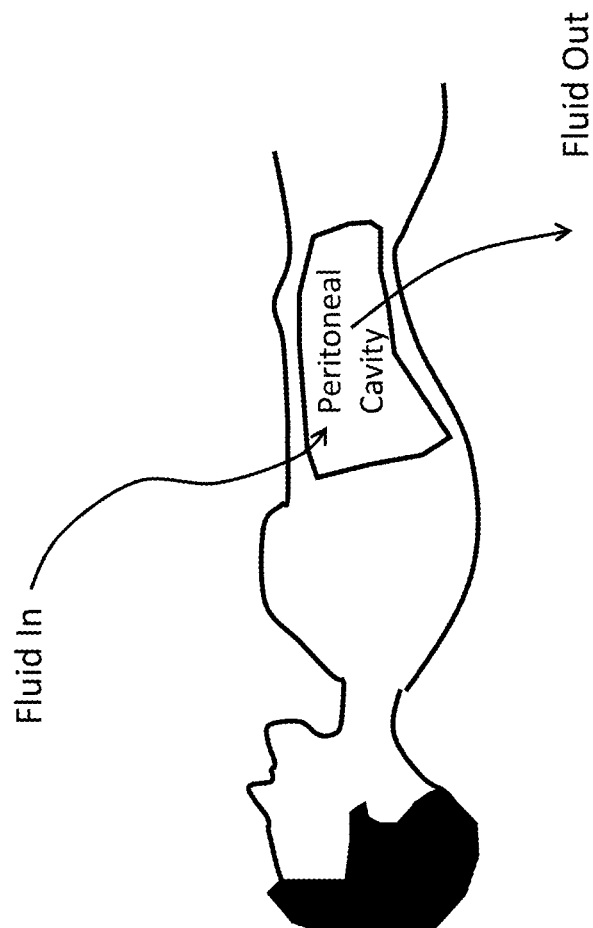
FIG. 47 depicts an exemplary embodiment of peritoneal cavity lavage with NO nanobubble solution.

FIG. 47 depicts an exemplary embodiment of peritoneal cavity lavage with NO nanobubble solution. This approach can be helpful in treating and/or preventing infection, enhancing peritoneal dialysis, and/or treating cancerous tumors of the abdomen. In some embodiments, the peritoneal cavity is lavaged with a solution containing oxygen and/or NO nanobubbles. An oxygen nanobubble solution can be utilized to deliver oxygen to the circulatory system of a patient. This can provide supplemental oxygen to patients that have impaired lungs or are undergoing surgery that affects the lungs (e.g. lung transplant). In some embodiments, the peritoneal cavity is lavaged in an alternating pattern of NO nanobubbles to dilate blood vessels followed by $O_2$ nanobubble solution to oxygenate. In some embodiments, NO nanobubble solution is utilized to wash harvested organs to disinfect before transplant.

Bladder Treatment

In some embodiments, NO nanobubble solution is introduced to the bladder and/or urinary tract to treat infection and/or cancer. In one exemplary embodiment, a patient with bladder cancer is treated by at least partially filling the bladder with a combination of Bacilius Calmette-Guerin (BCG) solution and nitric oxide nanobubble solution. In some embodiments, NO nanobubbles are generated within BCG solution prior to deliver to the patient. The NO nanobubbles can increase blood flow to the bladder, hastening the immune system response to the BCG solution.

Organ Transport

In some embodiments, oxygen nanobubble solution is utilized as a preservation media for harvested organs to provide oxygen during organ transport. In some embodiments, the oxygen nanobubble solution is pumped through the vasculature of the organ to perfuse the tissue with oxygen.

In some embodiments, vasculature of the lungs is perfused with a nanobubble solution containing NO and/or oxygen. This can be done for treatment and/or prevention of infection and/or to improve tissue oxygenation.

Figure 48:
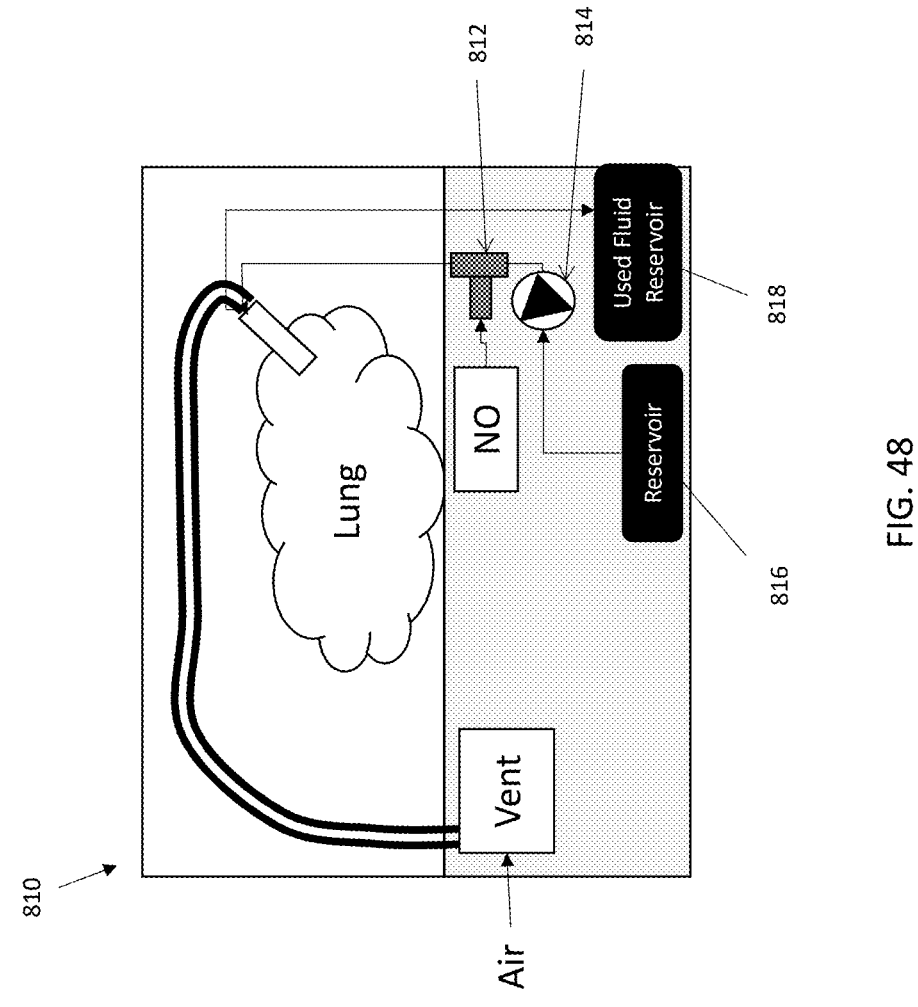
FIG. 48 depicts an organ transport device that perfuses tissue with nanobubble solution.

NO nanobubbles in solution can also be utilized during organ transport to help prevent infection and improve oxygenation. FIG. 48 depicts an exemplary embodiment of an organ transport device 810 that introduces NO nanobubbles to the perfusate using a nanobubble generator 812. The NO dilates vessels within the organ to decrease flow resistance, increase perfusion and decrease the potential for blood vessel blockage. The lung is ventilated with an oxygen-containing gas (e.g. air). A pump 814 pulls perfusate from a reservoir 816 of fluid. An optional degassing mechanism (not shown) removes larger bubbles and gas prior to entry into the organ. Nanobubble perfusate is pushed through the lung and back to a second reservoir 818 that houses used fluid. In this way, methemoglobin (the product of reaction between hemoglobin and nitric oxide) accumulation within the perfusate is not a concern because fresh perfusate is continuously utilized. In some embodiments (not shown), the perfusate is scrubbed of one or more of $CO_2$, metabolism byproducts, and methemoglobin and reused. In some embodiments, NO nanobubbles are generated in a liquid (e.g. saline) that is subsequently mixed with perfusate (e.g. blood). The NO can be sourced from multiple sources, including but not limited to gas cylinder, electric NO generator, NO donor molecules, $N_2O_4$ and other approaches.

Eye Surgery

In some embodiments, NO solution is delivered to the eye to treat infection and/or dilate blood vessels and increase blood supply to the tissues of the eye. In some embodiments, NO solution is applied to the exterior surfaces of the eye. In another embodiment, NO solution is utilized to flush out the lens fragments during cataract surgery to prevent infection. In some embodiments, NO solution is injected into the vitreous body of the eye to treat/prevent infection.

Open Wounds

Another clinical application for NO nanobubbles is the treatment of open wounds to prevent infection and/or cause vasodilation for increased blood flow. In wound applications, NO nanobubble solutions are placed directly on the wound. In some embodiments, higher viscosity fluids (e.g., gels) are preferred to prevent medicine migration. In some embodiments, a liquid, gel or liquid/gel mixture (e.g. saline with glycerin) is stored in a container. Pressurized NO is utilized to propel the mixture out of the container while also adding NO nanobubbles and dissolved gas to the mixture. In some embodiments, specialized bandages secrete NO nanobubble solution over time (continuously or periodically) to replenish the supply of NO at the surface of the wound.

Figure 49:
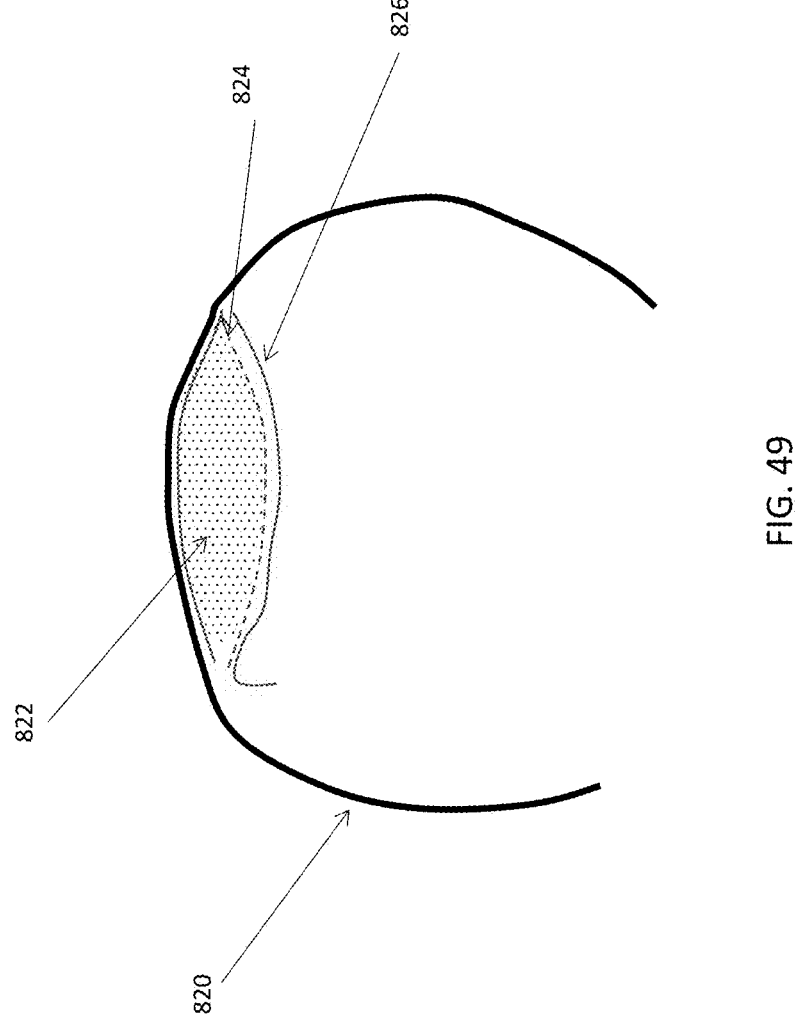
FIG. 49 depicts an adhesive bandage loaded with nanobubble solution for external application.

FIG. 49 depicts an exemplary bandage 820 that secretes a nanobubble solution over time. The bandage consists of a medicine chamber 822 with a perforated wall or membrane 824. The chamber walls are under tension. During storage, an impermeable membrane shield or storage shield 826 is adhered to the perforated surface to hold the nanobubble solution within the chamber. Prior to use, the shield is removed to initiate release of the nanobubble solution. The medicine chamber is held the surface of a wound with an adhesive bandage. In some embodiments, the bandage is packaged for storage and transport in a pressurized container to inhibit nanobubble loss. For example, a NO nanobubble bandage can be packaged in a nitrogen pressurized pouch.

Transplants & Grafts

Another area of medicine that can benefit from increased NO is the field of organ transplants and tissue grafts. Transplants and grafts involve integrating either autologous or donated tissue into a patient. The host tissue must integrate with the new tissue to provide vasculature to nutrient delivery and waste removal. NO-donating compounds and/or bubbles have the ability to promote angiogenesis (i.e., formation of new blood vessels) to facilitate integration of new tissue. Introduction of new materials to a patient can involve the unintended introduction of infectious organisms. The antiseptic properties of NO can also aid in preventing infection from taking root in and around newly implanted tissue. In one exemplary application, NO-releasing material is delivered to the location of a muscle graft site at the time of implantation. In another exemplary application, NO-releasing material is delivered to a graft treatment site periodically afterwards to combat clotting and necrosis.

Infections

NO nanobubble solution provides a potent antimicrobial (i.e. fungal, bacterial, viral) properties for treating infection. In addition, NO stimulates the immune system at low concentrations ($10^{-12}$ to $10^{-9}$ M). Local treatment is preferred over systemic treatment to minimize side effects, including harm to the gastrointestinal biome associated with systemic antibiotics and antifungal medications.

In some embodiments, NO nanobubble solution is utilized to sanitize a surface (e.g., hand sanitizer, surgical skin preparation) to prevent an infection. In some embodiments, NO nanobubble solution is utilized to treat one or more of bacterial, fungal and/or viral infections. In an exemplary embodiment, a NO nanobubble solution is placed in the ear canal to treat an infection. In another exemplary embodiment, NO nanobubble within mouthwash can be used to kill bacteria and microbes in the mouth and throat. In another exemplary embodiment, NO nanobubbles in an ointment or gel or cream are utilized to prevent and/or treat acne. In another embodiment, NO nanobubble solution is utilized to treat lesions (e.g., skin lesions) to prevent and/or treat infection. In some embodiments, a NO nanobubble solution is applied to a patient's feet to treat or prevent fungal infection (e.g., athlete's foot, infected to nail). In some embodiments, a NO nanobubble solution is placed on a wart to kill virus and promote blood flow.

NO nanobubbles can be used to treat internal infections as well. Nitric oxide has been shown to eradicate biofilms formed by bacterial colonies. NO nanobubbles can be injected in the location of the colony, for example. In other applications, NO nanobubbles can be applied to an area at risk of infection (e.g., percutaneous catheter site). For example, a site can be exposed to NO nanobubbles periodically to prevent an infection/biofilm from forming. In some embodiments, an indwelling catheter is constructed from or is coated with a NO-releasing material (e.g. NO nanobubble coating or NO-donor molecule) that releases NO over time to prevent infection. NO release from a donor molecule can be initiated by a variety of mechanisms, depending on the donor material chemistry, including but not limited to pH, water exposure, electrical voltage, temperature, enzymatic breakdown, ionic interaction and exposure to specific frequencies of light.

Kidney Dialysis

The disinfectant and vasodilative properties of NO can also be relevant to peritoneal dialysis. NO nanobubbles added to peritoneal dialysate aid in preventing peritoneal infection while also relaxing the smooth muscles in blood vessels within the peritoneal cavity. The dilated blood vessels promote blood flow through the peritoneal cavity, thereby increasing the rate of chemical transport into and out of the blood supply and shortening overall treatment time.

Kidney Protection

A bypass machine causes hemolysis, releasing hemoglobin (Hb) into the bloodstream. This loose hemoglobin scavenges NO from the blood vessels and plasma, causing depletion of NO in the vasculature, including the kidneys. As a result, kidney vessels can collapse and encounter permanent damage. In some embodiments, NO nanobubbles are utilized to prevent acute kidney failure. To prevent kidney damage, hemoglobin within the blood can be saturated with NO prior to flowing through the kidney. NO nanobubbles are introduced to the blood stream upstream of the kidney. In some embodiments, the NO nanobubbles are introduced via a blood oxygenator (e.g., ECMO). The NO nanobubbles are provided in a fluid (e.g., saline, lactated Ringer's solution, plasma, etc.). This method protects the kidney by preventing NO removal from the kidney by hemoglobin.

Fungal Infections

NO nanobubble solutions can be utilized to treat fungal infections (e.g., eczema, athlete's foot).

Diabetes

One of the complications associated with diabetes is chronic wounds worsened by infection and insufficient tissue oxygenation. Chronic wounds are most prevalent in the extremities (i.e., feet). The unhealthy tissue is more susceptible to infection and ultimately can lead to amputation. NO nanobubble solution applied to diabetic lesions can improve the patient's condition by treating infections, inducing vasodilation to improve blood flow and promoting angiogenesis and fibroblast activation. Nanobubble solutions can be applied topically as a gel or salve and also be injected via needle. In some embodiments, degradable material is implanted for sustained release of NO nanobubbles in the vicinity of a lesion.

Toothpaste

In some embodiments, NO nanobubbles can be included in toothpaste to disinfect the mouth. In some embodiments, nanobubbles of an anesthetic gas (e.g. nitrous oxide ($N_2O$), xenon, etc.) act as a numbing agent for sensitive teeth and gums. In some embodiments, nitrous oxide nanobubble solution is utilized as a mouth wash.

Non-Pulmonary Oxygenation

In some embodiments, oxygen level in a patient's blood is increased by oxygen transport through the rectal/colonic/intestinal wall. In some embodiments, this is done with gaseous oxygen plus NO. The NO dilates the blood vessels within the intestines to increase blood flow and oxygen transport. Gas can be introduced through the anus. In some embodiments, the gas is humidified to prevent drying out of tissues. The flow rate of gas is sufficient that transit time of the $NO/O_2$ mixture is short, preventing $NO_2$ formation. In some embodiments, a tube (e.g., endoscope) is navigated through the patient to a depth. Gas is introduced through the end of the tube and travels back along the intestinal track to exit the patient at the entry point. In some embodiments, exiting air passes through a scrubber (e.g., NOx scrubber, $NO_2$ scrubber, activated carbon, potassium permanganate, soda lime) prior to release to atmosphere. In some embodiments, exiting air is released to house vacuum.

In some embodiments, liquid with oxygen nanobubbles is introduced to the intestinal tract to increase oxygenation in the blood. In some embodiments, a volume of liquid is introduced and permitted to dwell for a period of time prior to being exchanged. In some embodiments, a continuous flow of liquid is introduced to the intestinal tract and exits the patient. In some embodiments, the liquid includes NO nanobubbles to promote blood flow through the intestines.

Non-pulmonary oxygenation is utilized in clinical applications where the pulmonary system is either not functioning sufficiently or is temporarily offline (e.g., lung transplant, trachea surgery, etc.). In one application, hypoxic neonates receive non-pulmonary oxygenation to supplement the limited amount of oxygen received through their pulmonary system.

Adjunct to Inhaled Medication

In some embodiments, inhaled surfactant can be utilized in neonates. In some embodiments, surfactant delivered to neonates to relieve surface tension in the lung is delivered in combination with NO nanobubbles to relax blood vessel walls and increase blood flow. In some embodiments, inhaled NO or NO nanobubble solution is delivered in combination with inhaled Tyvaso (nebulized liquid or dry powder) for treatment of pulmonary hypertension.

Adjunct to Systemic Medication

In some embodiments, NO liquid is delivered in combination with other therapy to increase the uptake and/or distribution of another drug due to blood vessel dilation. For example, NO nanobubbles can be delivered in combination with a chemotherapy drug. The NO nanobubbles dilate blood vessels within cancerous tumors, increasing the uptake of chemotherapy drug. In some embodiments, the nanobubble solution is delivered systemically (e.g., intravenous or oral route). In some embodiments, nanobubble solution is introduced to the blood vessels entering the tumor. In some embodiments, nanobubble solution is injected interstitially within the tumor to dilate blood vessels.

Myocardial Infarct and Stroke

In some embodiments, NO nanobubbles are delivered to a blood vessel locally via catheter prior to clot extraction (myocardial infarct (MI)I, stroke). The smooth muscle relaxation and blood vessel dilation facilitates clot removal. In some embodiments, the catheter is flushed with an non-NO-containing liquid (e.g. saline, heparinized saline) after NO solution bolus delivery. This ensures that all NO solution is delivered and non is left to age in the catheter.

Continuous delivery of NO nanobubbles after clot removal can also improve reperfusion of the tissue and decrease the risk of reperfusion injury. Upon removal of a thrombus and/or atherosclerotic lesion, NO travels downstream of the thrombus, dilating the blood vessels and decreasing the potential for fragments of emboli from the removal process from clogging vessels downstream.

In some embodiments for reperfusion in acute myocardial infarct (AMI) and ischemic stroke, NO is administered locally as a liquid formulation through an invasive catheter. NO has been shown clinically to inhibit platelet adhesion and aggregation as well assist in breaking apart platelet aggregates. In some embodiments, NO solution is delivered as an adjunct to other treatments (thrombolytics, [low molecular weight] heparin, antiplatelet drugs and other blood thinners. In other embodiments, NO solution is delivered as an adjunct to clinical procedures (e.g. thrombectomy, percutaneous transluminal coronary arthroplasty (PTCA), stent placement). The local administration of NO as a liquid formulation delivers in-vivo free NO that provides the following benefits: i) local vasodilation to facilitate the procedure and enhance thrombolysis ii) downstream vasodilation to prevent downstream micro embolism, iii) prevention of early oxygen-toxicity associated with reperfusion of the injured tissue, and iv) anti-platelet aggregation properties.

Atherosclerotic/Thrombo-Embolic Lesion Treatment

Atherosclerotic lesions and thrombus (blood clot) are frequently treated in the ambulance or very quickly after arrival at the hospital with tissue plasminogen activator (TPA) to dissolve clots. In some embodiments, a combination of TPA and nanobubble NO are delivered to the blood stream to dissolve the lesion and dilate the blood vessel, respectively, to reduce the time to reperfusion. In some embodiments, the NO nanobubbles are delivered systemically through an IV or syringe. In other embodiments, the NO nanobubbles are delivered locally at the location of the thrombus via catheter. One benefit of NO nanobubbles for thrombus application is that the NO is chemically active immediately after delivery, as compared to NO donor molecules that can take longer to breakdown into intravascular NO.

Blood Diseases

Nanobubbles with NO can be used to treat various blood diseases, such as sickle cell disease. In some embodiments, sickle cell crisis is treated with NO nanobubble solution. Sickle cell crisis occurs when a blood vessel becomes blocked by a collection of blood cells. This condition induces hypoxemia in downstream tissue and intense pain that lasts days to weeks. In some embodiments, a patient experiencing a sickle cell crisis event is delivered intravenous NO nanobubble solution upstream of the blood vessel blockage. The NO solution induces vasodilation in the region of the blockage, potentially dislodging the blockage and/or facilitating the blockage removal.

Catheter Navigation

In some embodiments, NO nanobubbles are delivered through a catheter to locally dilate blood vessels to make them easier to navigate.

In some embodiments, contrast solution for computed tomography (CT) visualization is loaded with nitric oxide nanobubbles to provide simultaneous visualization and dilation to facilitate catheter navigation.

In some embodiments, NO nanobubbles are delivered to a blood vessel before and/or during stent delivery to relax blood vessel. This approach reduces the forces on the stent delivery system to improve safety. It also enables stent to expand further without the contraction of the blood vessel working against it. In some embodiments, the stent delivery catheter is flushed with NO nanobubble solution before, during or after stent delivery. In some embodiments, the balloon used to dilate the blood vessel and/or balloon is made from a permeable material that permits the transfer of NO as a gas or nanobubble through the balloon wall during inflation.

Vasospasm

Vasospasm is a reaction of the smooth muscle in a blood vessel wall to physical stimulation. The smooth muscle contracts, decreasing the inner diameter of the blood vessel. A 50% reduction in vessel diameter due to vasospasm is not uncommon. This, in turn, increases resistance to blood flow and introduction of medical instruments (e.g., catheters). NO, is the active ingredient in nitroglycerin, which is typically taken systemically and reduces vascular tension systemically. Nitroglycerine use can result in significant reduction in blood pressure. In some embodiments, NO nanobubble solution or NO donor molecules (e.g., nitroglycerin, N-diazeniumdiolates, S-nitrothiols, N-nitrosamines, nitrates, metal-NO complexes, and nitrites) are introduced locally (e.g., by needle or catheter).

In some embodiments, NO solution is introduced through a catheter to facilitate catheter navigation. The NO solution can be introduced to the blood stream from the insertion sheath of the catheter or the catheter, itself. In some embodiments, the catheter includes openings along its length for release of NO-containing solution. In some embodiments, NO solution is introduced through the sheath to facilitate insertion of a catheter in the direction of blood flow. In some embodiments, NO solution is introduced through the inserted end of a catheter when the catheter is inserted against the direction of blood flow.

In some embodiments, NO solution is introduced systemically pre-operatively to prophylactically mitigate against vasospasm. For example, in one embodiment, 25 ml of 13 uM NO/Lactated Ringer's solution was introduced intravenously to a 70 kg female porcine test subject three times at 10-minute intervals. After the third delivery of solution, aggressive stimulation of the superficial femoral artery (SFA) with a balloon catheter resulted in no vasospasm response.

Figure 50:
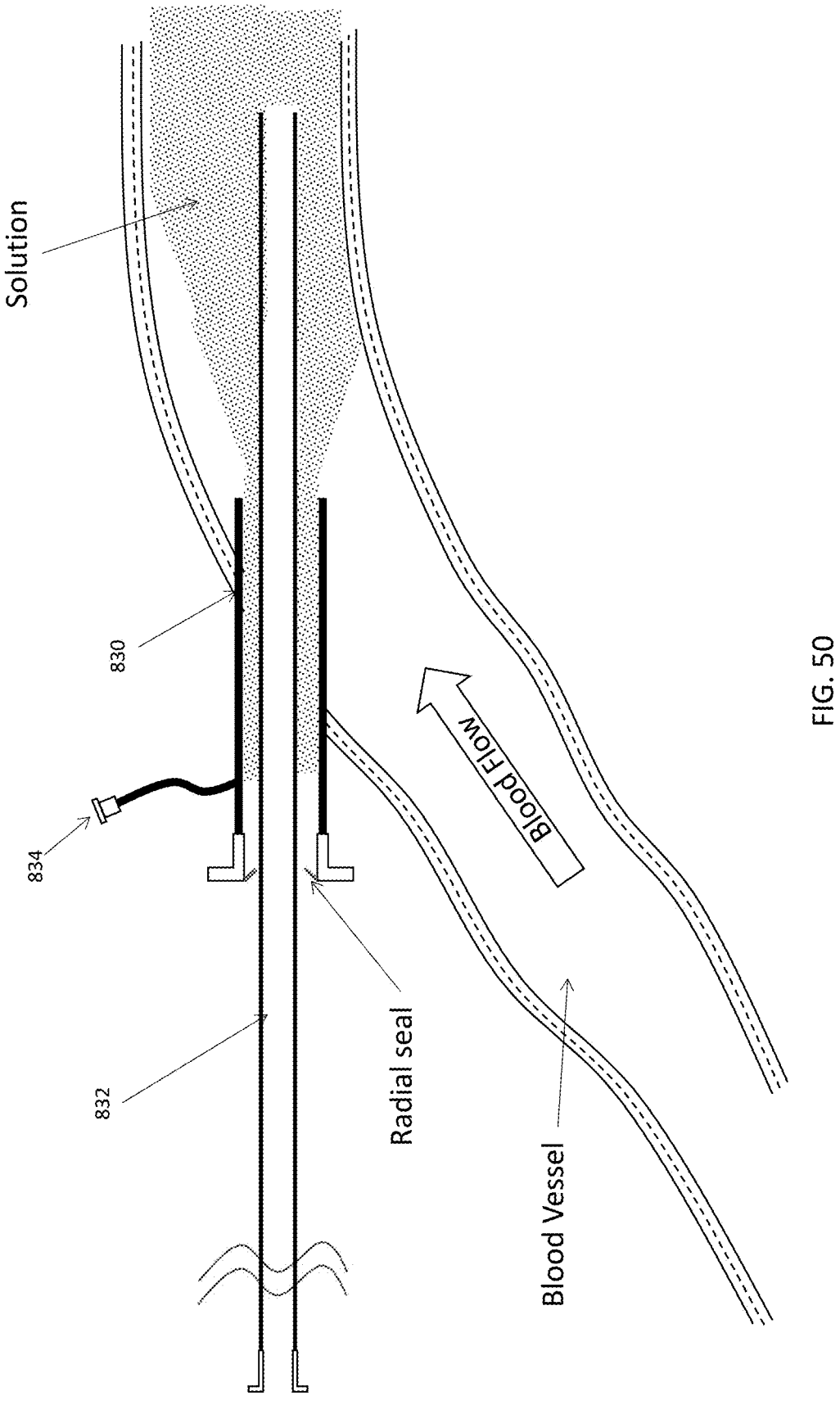
FIG. 50 depicts exemplary delivery of nanobubble solution through a catheter sheath.

FIG. 50 depicts an exemplary intravascular application of NO solution. A needle and access sheath 830 are utilized to gain access to the blood vessel. A catheter 832 is inserted into the vessel through the sheath 830. Using an injection port 834, NO solution is introduced through the annular space between the catheter and the sheath and travels downstream in the blood, along the inserted length of the catheter. The NO solution dilates the blood vessel along the inserted length of the catheter and further downstream, thereby facilitating insertion of the catheter. In some embodiments, NO solution is introduced through one or more lumens in the catheter instead of or in addition to the access sheath.

Figure 51:
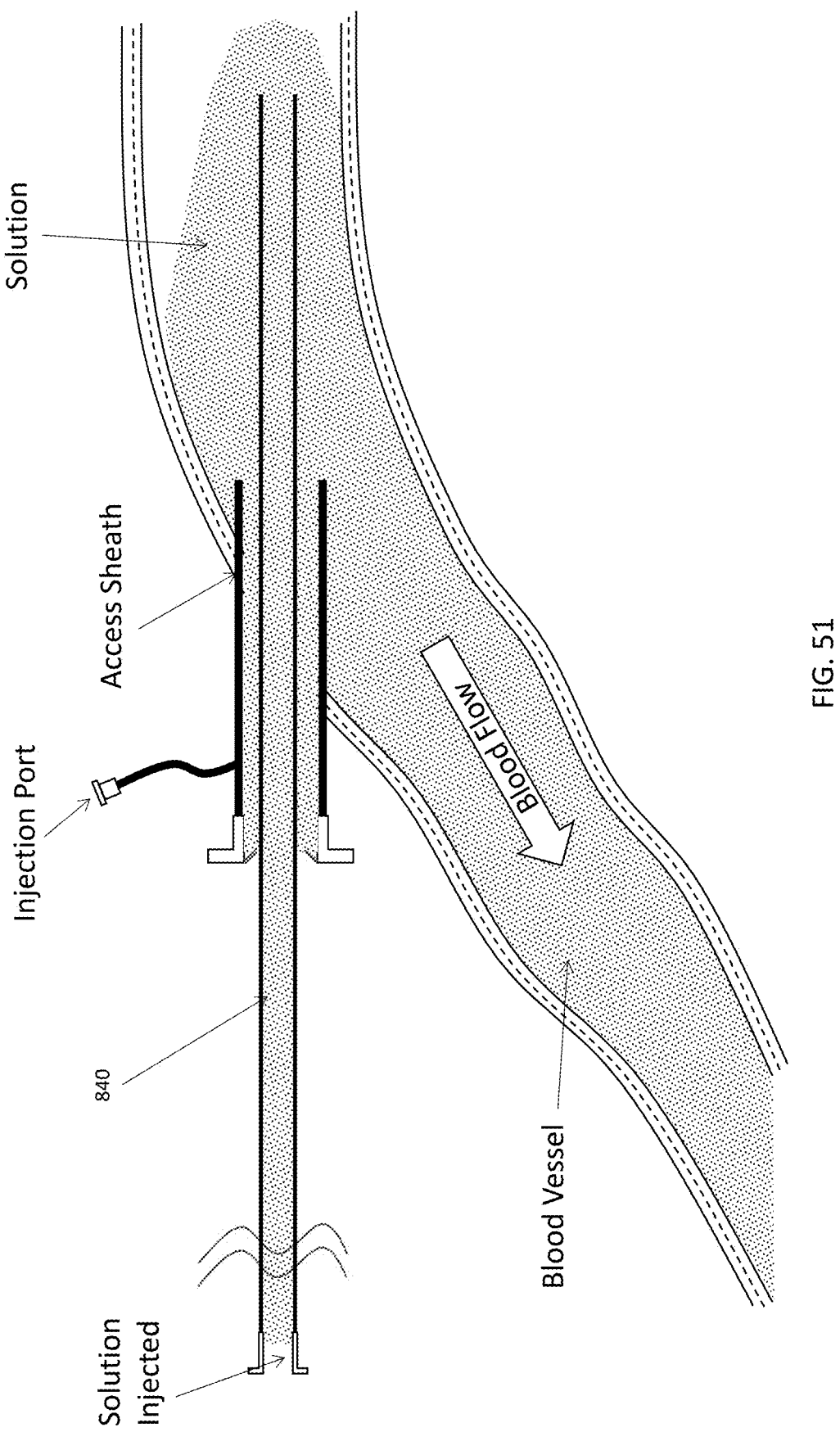
FIG. 51 depicts exemplary delivery of a nanobubble solution through a catheter.

FIG. 51 depicts another exemplary intravascular application of NO solution. A catheter 840 is advanced against the direction of blood flow. NO solution is introduced through one or more lumens in the catheter 840. The NO solution is carried with the blood along the inserted length of the catheter, dilating the vasculature around the catheter and facilitating catheter insertion. In another embodiment (not shown), NO solution is delivered through the catheter to dilate the vasculature downstream of the catheter.

Figure 52:
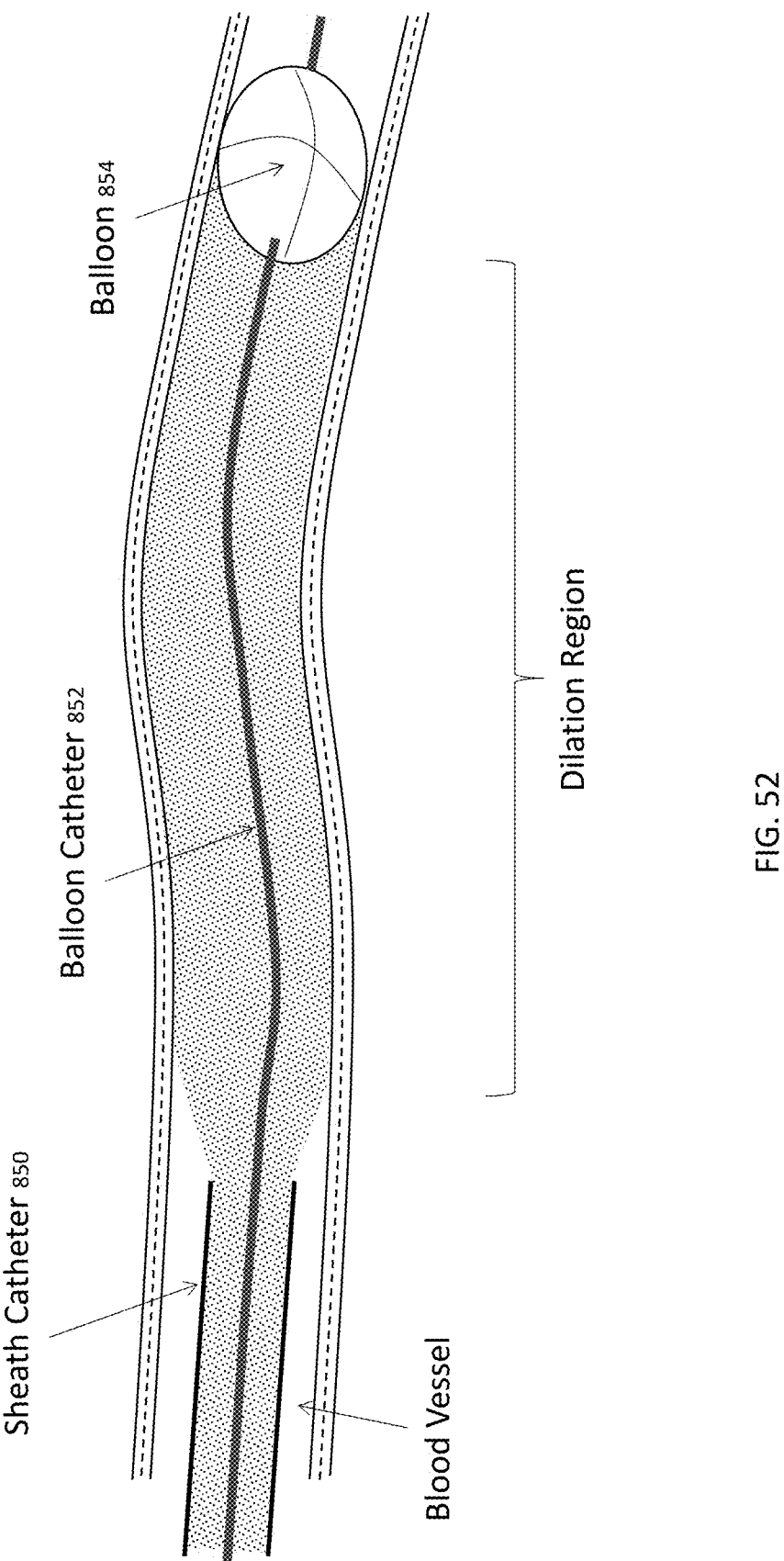
FIG. 52 depicts exemplary delivery of a nanobubble solution through a catheter to an obstructed blood vessel.

FIG. 52 depicts an exemplary embodiment of local delivery of NO solution to a blood vessel. A catheter sheath 850 has been inserted to a specific anatomical location. A balloon catheter 852 is inserted beyond the target anatomical location. The balloon 854 is inflated to temporarily block blood flow. NO solution is introduced to the location through either a lumen in the balloon catheter or the catheter sheath. The NO solution acts upon the smooth muscle in the local area to increase the diameter of the blood vessel. In one application, a stent is delivered to the anatomical location during vessel relaxation. This decreases the force required to deploy the stent and helps maximize expansion and/or deployment of the stent.

In one exemplary embodiment, an experiment was performed in which the right renal artery of a 70 kg Yorkshire pig was stimulated with a catheter. The internal diameter of the superior branch of the artery decreased from a initial diameter of 4.1 mm to a diameter of 1.1 mm, 4 minutes after stimulation with a guide wire and balloon. A balloon was inflated downstream of the vasospasm region and 25 ml of 13 uM NO solution was introduced into the vessel in the region of the vasospasm. The vasospasm resolved within 2 minutes of delivery of NO. In another example of the same test subject had an initial internal diameter of 4.3 mm. The hepatic artery was stimulated with a guide wire and balloon. Two minutes after stimulation, the diameter of the hepatic artery had decreased to 2.3 mm. A balloon was placed downstream of the region of vasospasm and 25 ml of 13 uM NO solution as introduced to the blocked blood vessel slowly, over the course of two minutes. Two minutes after the last of the NO bolus was delivered, the internal diameter of the hepatic artery returned to 4.0 mm. Similar treatments have been performed on the spleen, carotid arteries, coronary arteries, peripheral arteries, maxillary artery and other arteries within a living system. In another exemplary embodiment, vasospasm was triggered in a right coronary artery with a guide wire. A vasospasm occurred reducing the internal diameter of the right coronary artery from 3.5 mm to 1.4 mm. Four 5 ml injections of NO nanobubble solution were slowly delivered (~30 seconds delivery) to the vasospasm location every 1 minute for four minutes. After the fourth delivery of solution, the vasospasm was resolved and the artery had returned to its initial internal diameter.

Figure 56:
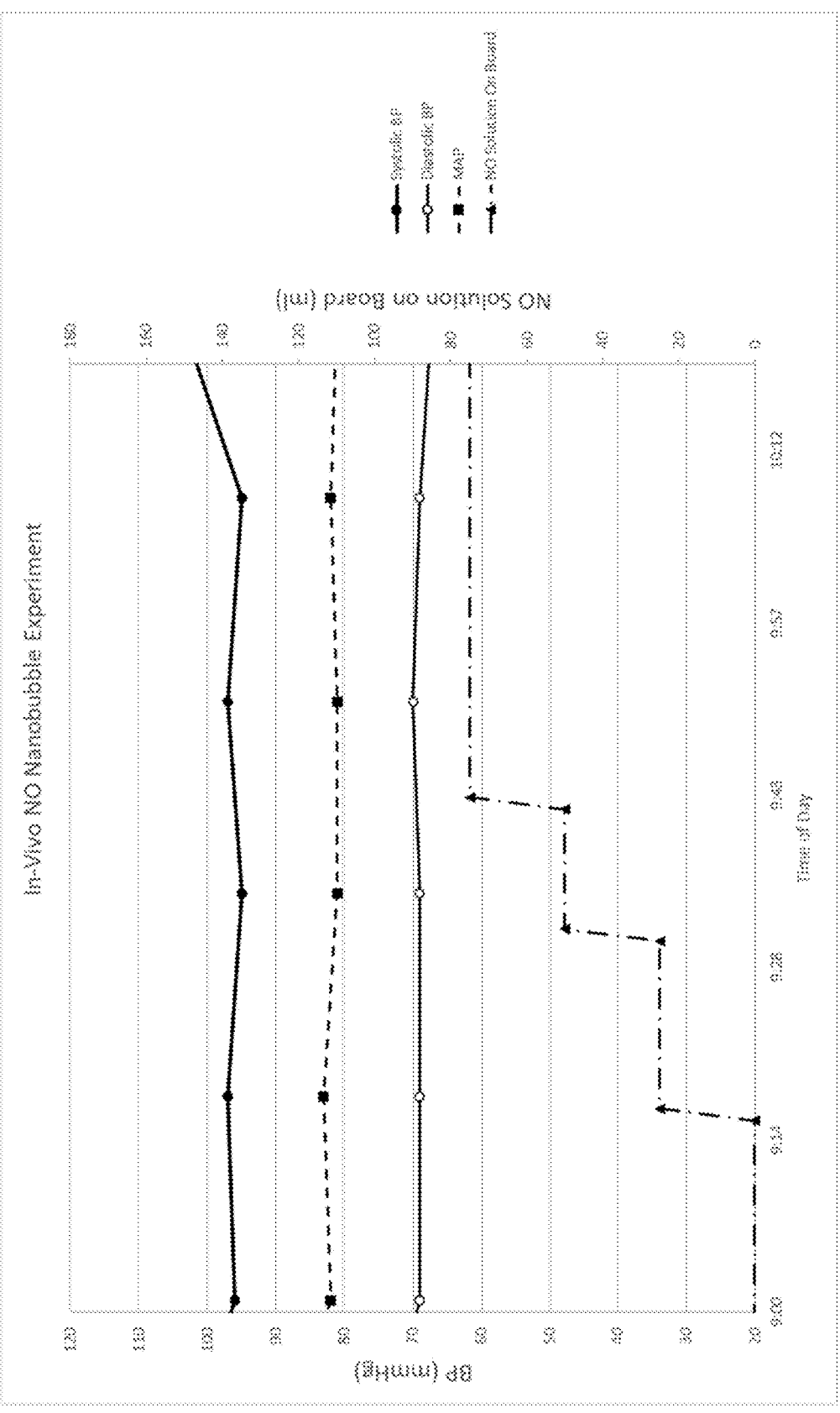
FIG. 56 shows an exemplary graph of data from an experiment performed on the in-vivo pig showing the effect of NO nanobubbles on blood pressure of the animal.

Nitroglycerine and verapamil hydrochloride are commonly used to suppress vasoconstriction; however they decrease systemic blood pressure. When NO nanobubble solution was utilized, there was no effect on systemic blood pressure. FIG. 56 shows an exemplary graph of data from the experiment performed on the in-vivo pig showing the effect of NO nanobubbles on blood pressure of the animal.

FIGS. 53A, 53B, and 53C depict a progression of a catheter inserted into a vessel. FIG. 53A illustrates an exemplary catheter inserted within a blood vessel. The intention is to steer the catheter into a side branch, similar to entering the renal arteries from the aorta. NO nanobubble solution is ejected from the catheter into the blood stream in FIG. 53B. The NO solution induces vasodilation within the local vasculature, making the side branch larger and easier to steer the catheter, as shown in FIG. 53C. In some embodiments, a guide wire (not shown) is utilized with the catheter to assist in navigating the anatomy.

Figure 54C:
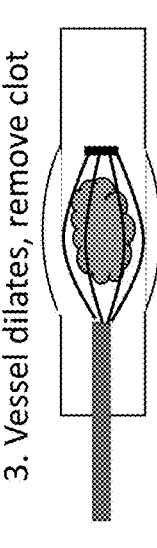
FIGS. 54A, 54B, and 54C depict exemplary delivery of a nanobubble solution through a catheter to facilitate clot removal.
Figure 54B:
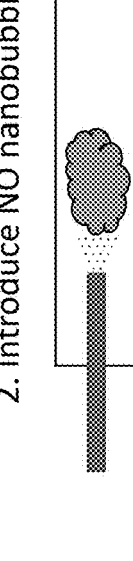
Figure 54A:
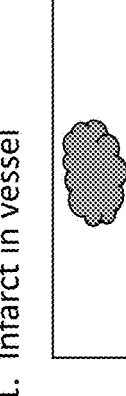

FIGS. 54A, 54B, and 54C depict a progression of a catheter inserted into an infarcted vessel. FIG. 54A illustrates an exemplary catheter inserted into an infarcted blood vessel. NO nanobubble solution is ejected from the catheter into the blood stream, as shown in FIG. 54B. The blood vessel walls relax, enlarging the cross-sectional diameter of the blood vessel. The large cross-section facilitates removal of the infarct, as shown in FIG. 54C.

Adjunct to Other Vascular Therapies

In other applications, nanobubble solutions are delivered before, during and/or or after intravascular RF/microwave and cryotherapy ablation of neoplastic lesions. In some embodiments, NO nanobubble solution is delivered to decrease the effect of embolic material on downstream tissue. In another embodiment, anesthetic nanobubble solution is delivered locally to decrease pain and/or arrythmia. In another embodiment, NO nanobubble solution is utilized during RF/microwave/cryotherapy device placement and/or adjuvant therapy to minimize vasoconstriction. In some embodiments, intravascular ultrasound is utilized to hasten the release of nanobubble gas locally.

In some embodiments, a catheter external surface is covered with a NO releasing compound (e.g. NO nanobubbles trapped in a matrix material, NO-donor molecules). In some embodiments, the catheter surface is coated with the NO donor molecule. In some embodiments, the NO donor molecule is chemically bonded to the surface of the catheter. In some embodiments, the compound is activated by one or more of exposure to blood, application of electricity (e.g. current, voltage), exposure to an acid, exposure to a base, exposure to water molecules, and exposure to a pH. The inserted portion of the catheter releases NO into the surrounding tissue (e.g. bloodstream, interstitial space, muscle, etc.).

In some embodiments, one or more lumens of a catheter include a NO donor molecule. In some embodiments, the NO donor molecule is in the form of a lining or coating to the lumen. In other embodiments, the NO donor molecule is in the form of an insert within the lumen of the catheter that fluid flows along and around. As liquids are introduced to the patient, the fluid picks up NO from the NO donor molecules and carries the NO in the liquid out the end of the catheter and into the target tissue and/or bloodstream.

In some embodiments, NO release from a NO donor molecule on a surface requires exposure to an activation chemical. In some embodiments, an activating material (e.g. enzyme, electrolyte solution, acid, base) is passed through the catheter to activate the release of NO donor compounds in or on the catheter. In a similar but opposite embodiment, a donor molecule is passed through the catheter and contacts activator material on one or more surfaces of the catheter.

These NO release concepts are equally applicable to implanted materials in the prevention of infection and biofilm formation.

Local delivery of NO solution offers the following improvements: reduced side effects, reduced cost, ease of administration, shortened time to effect, and local administration. There are also systemic applications of NO solution that can provide benefit. In some embodiments, a patient with sepsis receives an intravascular (IV) infusion to treat the infection. In some embodiments, the infusion is continuous. In other embodiments, the infusion is intermittent. In some embodiments, delivery of NO solution is limited based on a methemoglobin measurement to keep methemoglobin levels below a threshold.

Patients with acute respiratory distress syndrome (ARDS), pneumonia, trauma and other lung injuries experience sheering and tearing of the lung tissue that results in fluid leakage into the lungs and pathogen leakage into the circulatory system. Pathogen detection by the immune system triggers an inflammatory response (cytokine storm) which, in turn, triggers additional inflammatory responses throughout the body and organs. This systemic inflammation can lead to multi-organ failure and death. In some embodiments, NO solution is infused systemically to combat the inflammatory process with vasodilation and kill pathogens. In some embodiments, NB are generated in fluid that is flowing from an IV bag to the patient blood vessel.

This approach is applicable to multiple locations within the vascular system, including but not limited to the carotid, coronary, renal, hepatic, and peripheral arteries as well as neurovasculature.

Owing to the fact that NO rapidly reacts with hemoglobin to form methemoglobin and increased methemoglobin levels can be dangerous to the patient, methemoglobin levels are typically monitored in a patient undergoing vascular delivery of NO to ensure that safe levels of methemoglobin are not exceeded. In some embodiments, a methemoglobin measurement system is integrated into an NO solution delivery system.

Injected Anesthesia

Nanobubble technology can also be utilized to induce anesthesia. The anesthesia can be local (e.g. intramuscular injection, subcutaneous injection) or systemic (e.g. IV delivery). The solution is formed by passing anesthetic gas through a nanobubble generator to form nanobubbles of anesthetic gas in a liquid medium. Excess anesthesia gas (i.e. gas that does not become nanobubbles) can be vented or reused, as shown in multiple nanobubble generation system embodiments throughout this document. This approach provides faster induction and uses less anesthetic gas than inhaled anesthesia. Example gases are nitrous oxide, halothane, isoflurane, desflurane, sevoflurane, halothane, and S flurand.

When anesthesia is induced by inhalation, it is common to recirculate the anesthetic gas to conserve the anesthetic gas. This presents a challenge in knowing the concentration of anesthetic gas in the respiratory circuit. One of the benefits of intravascular anesthesia is that it separates ventilation from anesthesia, eliminating the need for rebreathing (i.e. gas reuse) in the respiratory circuit. In some embodiments, anesthetic nanobubble solution is introduced to an arterial line or IV to act on the heart or brain, for example. In some embodiments, the anesthetic gas nanobubble solution is generated to a known concentration (e.g. the maximal concentration) prior to introduction to the patient vasculature. In some embodiments, the anesthetic nanobubble solution is delivered at a constant rate (e.g. IV drip). In other embodiments, the anesthetic nanobubble solution is delivered in periodic boluses. Nanobubble technology enables the delivery of anesthetics that are a gas at room or body temperature in a liquid. In another embodiment, nanobubble of anesthetic gas in a saline medium is injected in the vicinity of a target nerve to temporarily anesthetize the nerve.

Nanobubbles with Other Gases

Helium has been shown to protect myocardial tissue from ischemia, reducing the amount of infarcted tissue by inhibiting mitochondrial permeability transition pore opening. In some embodiments, helium nanobubbles are delivered to an infarcted region to protect against necrosis. Delivery to the infarcted region before, during and after infarct removal have been contemplated.

Xenon and nitrous oxide have been shown to have anesthetic properties. Nanobubble solutions of anesthetic gases enable the safe delivery of gases in an open environment. In some embodiments, a nanobubble solution with anesthetic gas is used as a topical agent to anesthetize tissue (e.g., skin). In some embodiments, anesthetic nanobubble solution is utilized in toothpaste or mouthwash to reduce mouth pain.

Hydrogen is known to detoxify a patient's physiology of the hydroxyl radical. Hydrogen is currently delivered to patients through inhalation or ingestion (drinking water with dissolved hydrogen). Liquids with hydrogen nanobubbles can provide more hydrogen per unit volume of liquid than dissolved gas. In some embodiments, hydrogen nanobubble solution is delivered to the blood stream. Hydrogen nanobubbles may provide treatment by dampening immune cascade reactions, treatment of inflammatory disease (e.g., rheumatoid arthritis), and treatment of inflammation related to cardiac disease and stroke.

Figure 55A:
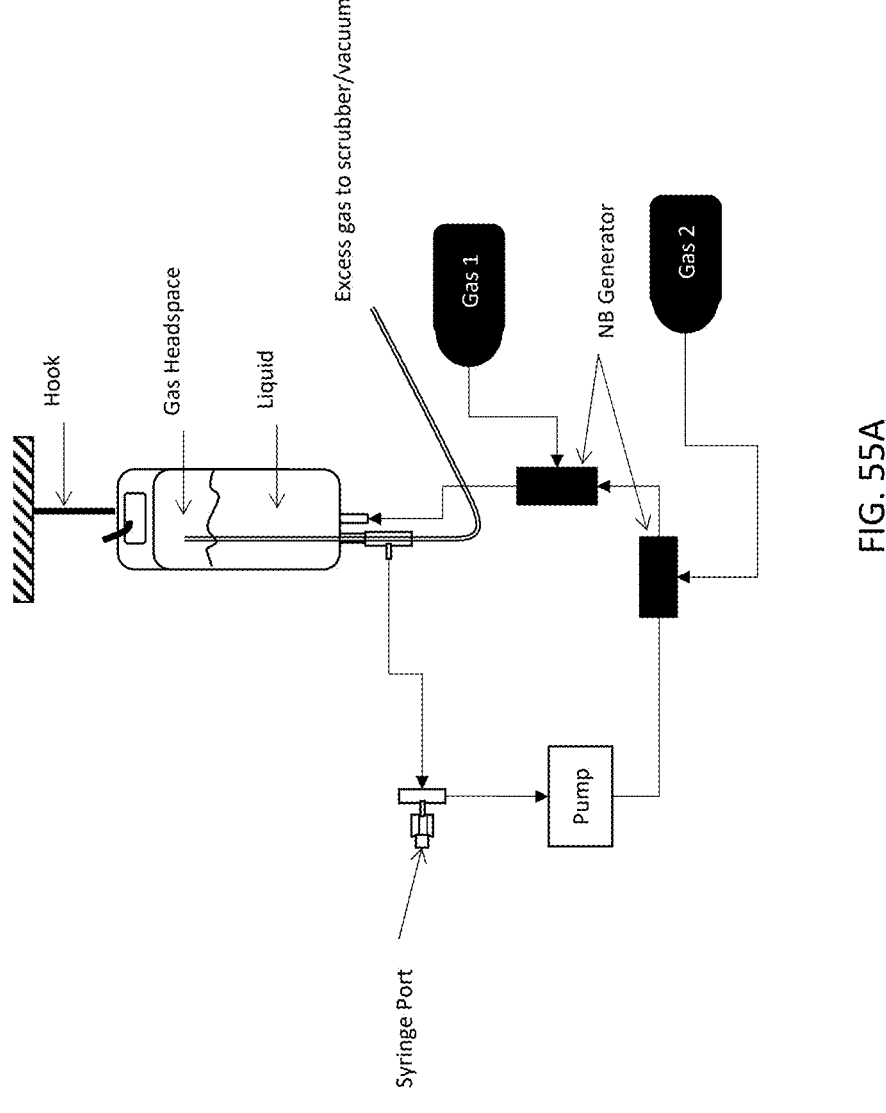
FIG. 55A depicts a nanobubble generation system that generates bubbles from two gas sources.

In some embodiments, nanobubbles are generated from a gas mixture (e.g. NO+xenon). In another embodiment, a solution is created with nanobubbles made from two or more different gases. In other words, the solution could contain both nanobubbles from a first gas and nanobubbles from a second gas. FIG. 55A depicts a nanobubble generation system that sources two independent gas reservoirs. The two gases passes through two independent nanobubble generators (e.g. venturi) to form nanobubbles in a flow of liquid. In some embodiments, the two gases are the same type of gas for one or more of redundancy, higher through-put, or shorter time to maximum bubble concentration. In other embodiments, the two gas types are different.

Figure 55B:
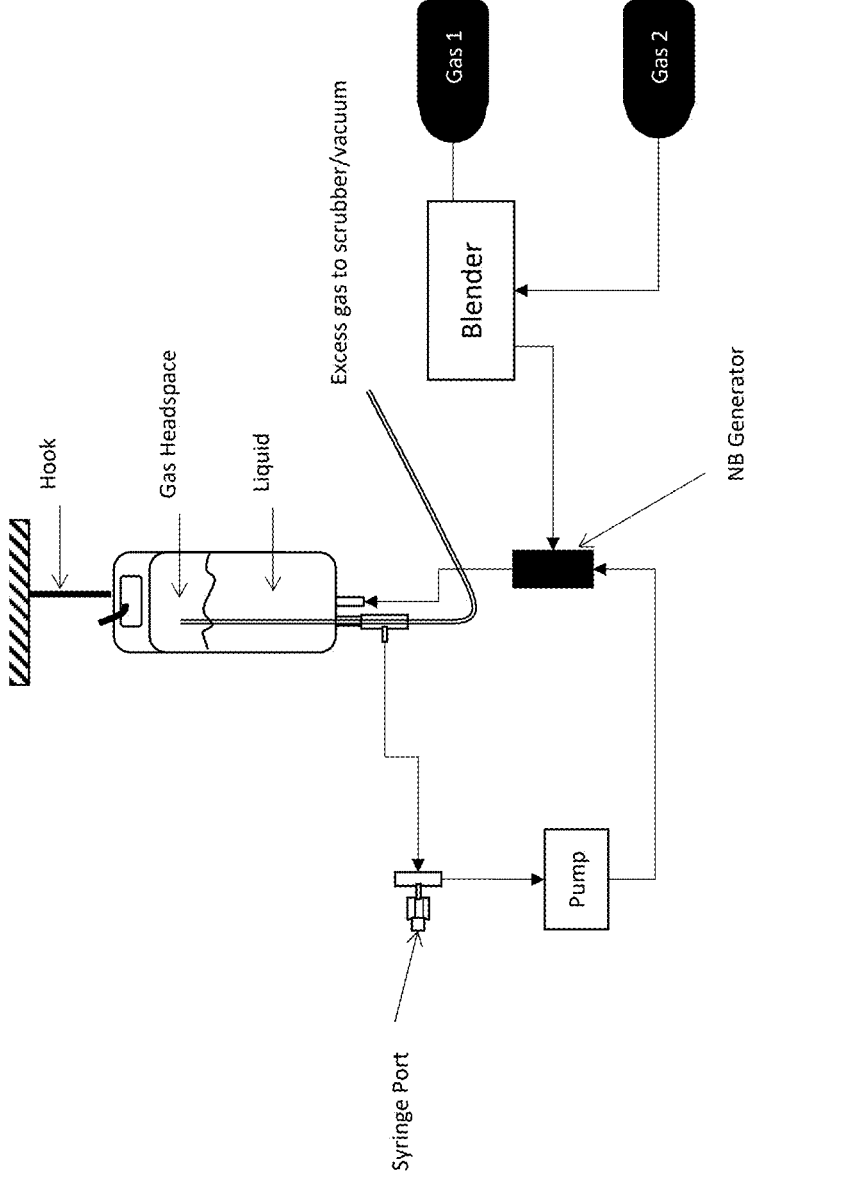
FIG. 55B depicts a nanobubble generation system that includes a gas blender.

FIG. 55B depicts a nanobubble solution that sources gas from two independent sources. The gases flow through a blender that is set to mix the two gases to a target ratio. The gas mixture then passes through a nanobubble generator to form nanobubbles in a liquid flow. In some embodiments, pressure regulators (not shown) are utilized to reduce the pressure of the gases from their reservoir pressure to a target input pressure for the blender. In other embodiments, a pressure regulator between the blender and nanobubble generator (not shown) reduces the gas pressure to a target input level for the nanobubble generator.

Treatment of Sexual Dysfunction

Some sexual dysfunction in females and males is attributed to insufficient blood supply to the affected region of the anatomy. Application of NO nanobubble solution in the form of a gel, hydrogel or liquid to the affected area can improve blood flow owing to the vasodilative properties of NO. The NO nanobubble solution can be applied either topically or infused. In some embodiments, a liquid (e.g., gel, hydrogel, oil, salve, lubricant) containing NO nanobubbles is applied directly to tissue. In some embodiments, a bandage with one or more needles (e.g., microneedles) introduces NO nanobubble solution subcutaneously. In some embodiments, NO nanobubbles are utilized as an adjunct therapy for existing hormone or systemic vasodilator therapy (i.e., estrogen and sildenafil).

General Cleaning and Disinfection

NO solutions (dissolved or nanobubble) can be utilized as a disinfectant and odor remover. In some embodiments, NO solution is utilized as a liquid or aerosol to remove odors from a pet.

In some embodiments, a nanobubble solution containing nitric oxide is utilized to clean surfaces (e.g., walls, chairs, keyboards, toilets).

Medical Instrument Cleaning

In some embodiments, a NO nanobubble solution is utilized to sterilize medical equipment. In some embodiments, an endoscope is one or more of flushed with or submerged in a NO nanobubble solution for disinfection.

Nanobubble Measurement

The amount of gas within a liquid is a function of the dissolved gas and gas in nanobubble form. The amount of gas in nanobubble form is a function of the size and quantity of nanobubbles as well as the concentration of gas within the nanobubbles. The size of nanobubbles is typically a distribution (e.g., 50-200 nm). The gas concentration can vary as well from a few ppm to tens of thousands of PPM to pure gas. When the gas is not pure, it is typically balanced with an inert gas (e.g., nitrogen).

Prior to clinical delivery, it is important to quantify the amount of nanobubble gas within the liquid. Several methods have been described.

In some embodiments, the volume change of liquid is measured and utilized to quantify the amount of gas introduced. In some embodiments, the density of the nanobubble solution is indicative of the amount of gas in solution (i.e., more nanobubbles results in less dense fluid).

In some embodiments, the amount of gas introduced to the water is measured as the difference between the quantity of gas introduced to the nanobubble generator minus the amount of gas released from the generation process.

Optical Measurement

In some embodiments, a fluid can be excited with ultrasound to release the nanobubbles and measure gas in a sweep gas with a gas analyzer. In some embodiments, an optimal ultrasound frequency is utilized for nanobubble rupture. The optimal ultrasound frequency is identified as the frequency that releases all of the nanobubbles the fastest.

In some embodiments, Diaminofluorescein-FM (DAF-FM)), a dye, is introduced to the nanobubble solution. The DAF-FM becomes fluorescent when it reacts with nitric oxide in the solution. The amount of fluorescence in the solution is measured (e.g. by fluorometer) to determine the quantity of nitric oxide in solution.

In some embodiments, ultrasound is utilized to release NO from a nanobubble solution into a headspace. A NO sensor (e.g. electrochemical sensor) measures the concentration of NO within the headspace after ultrasonic stimulation of the liquid solution. The quantity of NO that was in nanobubble form can be calculated based on the volume of the headspace and the concentration of NO indicated by the sensor. This approach eliminates the need for a sweep gas and integration via calculus of experimental data.

Sterilization

Clinical applications of medicinal gas in a liquid media often require sterility. In some embodiments, the gas-loaded liquid (e.g. dissolved, nanobubble) is prepared under aseptic conditions to yield a sterile product. In other embodiments, the gas-loaded liquid is prepared and then passed through a filter to remove pathogens and other contaminants. Typical sterile filters are roughly 0.2 micron which is sufficient to remove bacteria. Nanobubbles are small enough to pass through a 0.2 micron filter without significant losses. When a delivery device is utilized (e.g. catheter, syringe), the gas-loaded liquid can either be sterilized prior to loading the delivery device or be sterilized as it is dispensed from the delivery device.

Post-Use

After a desired quantity of nanobubble solution has been delivered to a patient, the remaining solution can be deactivated to prevent exposure to care givers and/or introduction of hazardous compounds to the waste stream. In some embodiments, an NO nanobubble solution is neutralized by adding one or more of DAF-FM DA (Diaminofluorescein-FM diacetate), TBAPF6 (Tetrabutylammonium hexafluorophosphate), CO-OMX (cobalt tetraphenylporphyrin), and DNICs (dinitrosyl iron complexes) prior to disposal.

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

The invention claimed is:

1. A nanobubble generation system for generating a medicinal solution, comprising:
    a reservoir configured to store a liquid;
    a source of medicinal gas;
    a pump configured to propel the liquid from the reservoir;
    a nanobubble generator in the form of a venturi and in fluid communication with the reservoir and the source of medicinal gas, the nanobubble generator configured to form a nanobubble solution comprising nanobubbles of the medicinal gas in the liquid;
    a return flow path configured to deliver the nanobubble solution exiting the nanobubble generator to the reservoir such that the nanobubble solution passes through the nanobubble generator and the reservoir a plurality of times; and
    a controller configured to modulate a concentration of nanobubbles in the nanobubble solution using one or more inputs, the one or more inputs comprising the plurality of times the nanobubble solution passes through the return flow path.

2. The system of claim 1, further comprising a delivery device configured to deliver a portion of the nanobubble solution exiting the reservoir to a target tissue to treat a medical condition in a patient.

3. The system of claim 2, wherein the delivery device comprises a syringe port, a syringe, a needle, and a catheter to deliver the nanobubble solution to the target tissue.

4. The system of claim 1, wherein the pump is at least one of a peristaltic pump, a syringe pump, a screw pump, a gear pump, and a diaphragm pump.

5. The system of claim 1, wherein the reservoir is removable.

6. The system of claim 1, wherein the reservoir is in the form of a bag.

7. The system of claim 1, wherein the liquid is in the form of at least one of an aqueous solution, a lipid, and an alcohol.

8. The system of claim 1, wherein the liquid is at least one of sesame oil, silicone oil, mineral oil, ethanol, isopropyl alcohol, heparin, saline, heparinized saline, lactated Ringer's solution, phosphate-buffered saline, and biological fluids.

9. The system of claim 1, wherein the liquid includes a pH buffer.

10. The system of claim 1, wherein the gas is one or more of nitric oxide, carbon monoxide, carbon dioxide, ozone, oxygen, helium, nitrogen, nitrous oxide, argon, xenon, and an anesthetic.

11. The system of claim 1, wherein the one or more inputs comprises one or more of temperature, a concentration of the gas, pH of the liquid, a flow rate of the liquid, pressure of the medicinal gas from the source, pressure of gas in the reservoir, quantity of gas added to the liquid, viscosity of the liquid, time since nanobubble solution creation, nanobubble generator operating time, and osmolality.

12. The system of claim 1, wherein a dose of nanobubble solution is configured to be modulated by one or more of a quantity of dissolved and nanobubble gas in the liquid and the quantity of liquid delivered.

13. The system of claim 1, wherein the nanobubble solution is configured to be removed from the system intermittently.

14. The system of claim 1, wherein the nanobubble solution is configured to be removed from the system continuously.

15. The system of claim 1, further comprising a flow path configured to vent excess gas from the system.

16. The system of claim 1, further comprising a scrubber configured to scrub excess gas before release from the system.

17. The system of claim 16, further comprising one or more of a valve and a pump to control a flow of the excess gas through a vent.

18. The system of claim 1, wherein a molarity of the gas in the liquid is from about 0.1 mM to 3 mM.

19. The system of claim 1, further comprising a temperature modulation component configured to chill at least one of the liquid upstream of the nanobubble generator, the nanobubble solution downstream of the nanobubble generator, and the liquid reservoir.

20. The system of claim 1, wherein the nanobubble solution is configured to be used to treat a medical condition, the medical condition being at least one of cancer, open wound, urinary tract infection, eye infection, organ transplant, skin graft, fungal infection, bacterial infection, viral infection, kidney disease, diabetes, myocardial infarct, stroke, atherosclerotic lesion, thrombus, blood disease, hair loss, and vasospasm.

21. A nanobubble generation system for generating a medicinal solution, comprising:
    a reservoir configured to store a liquid;
    a source of medicinal gas;
    a nanobubble generator in fluid communication with the reservoir and the source of medicinal gas, the nanobubble generator configured to form a nanobubble solution of nanobubbles of the medicinal gas in the liquid;
    a return flow path configured to deliver the nanobubble solution exiting the nanobubble generator to the reservoir such that the nanobubble solution passes through the nanobubble generator and the reservoir a plurality of times; and
    a controller configured to modulate a concentration of nanobubbles in the nanobubble solution using one or more inputs, the one or more inputs comprising the plurality of times the nanobubble solution passes through the return flow path,
    wherein at least a portion of the nanobubble solution is configured to be used to one or more of prevent and treat a vasospasm in a blood vessel.

* * * * *